(12) United States Patent
Lee et al.

(10) Patent No.: US 9,655,871 B2
(45) Date of Patent: *May 23, 2017

(54) **COMPOSITION COMPRISING A PURIFIED EXTRACT ISOLATED FROM *PSEUDOLYSIMACHION ROTUNDUM* VAR. *SUBINTEGRUM* CONTAINING ABUNDANT AMOUNT OF ACTIVE INGREDIENT OR THE COMPOUNDS ISOLATED THEREFROM, AS AN ACTIVE INGREDIENT FOR TREATING A CHRONIC OBSTRUCTIVE PULMONARY DISEASE AND THE USE THEREOF**

(71) Applicants: YUNGJIN PHARMACEUTICAL CO., LTD, Seoul (KR); KOREA RESEARCH INSTITUTE OF BIOSCIENCE AND BIOTECHNOLOGY, Daejeon (KR)

(72) Inventors: Yongnam Lee, Suwon-si (KR); Ji-seok Yoo, Suwon-si (KR); Dae-hee Shin, Seoul (KR); Byung-hwan Ryoo, Seongnam-si (KR); Kyung Seop Ahn, Daejeon (KR); Sei Ryang Oh, Daejeon (KR); Hyeong Kyu Lee, Daejeon (KR); In Sik Shin, Daejeon (KR); Doo Young Kim, Daejeon (KR); Ok-Kyoung Kwon, Daejeon (KR); Hyuk Hwan Song, Daejeon (KR); Seung Hyung Kim, Daejeon (KR); SuUi Lee, Daejeon (KR)

(73) Assignees: YUNGJIN PHARMACEUTICAL CO., LTD., Seoul (KR); KOREA RESEARCH INSTITUTE OF BIOSCIENCE AND BIOTECHNOLOGY, Daejeon (KR)

(*) Notice: Subject to any disclaimer, the term of this patent is extended or adjusted under 35 U.S.C. 154(b) by 0 days.

This patent is subject to a terminal disclaimer.

(21) Appl. No.: 14/780,503

(22) PCT Filed: Apr. 9, 2014

(86) PCT No.: PCT/KR2014/003080
§ 371 (c)(1),
(2) Date: Sep. 25, 2015

(87) PCT Pub. No.: WO2014/168413
PCT Pub. Date: Oct. 16, 2014

(65) Prior Publication Data
US 2016/0051612 A1    Feb. 25, 2016

(30) Foreign Application Priority Data

Apr. 10, 2013 (KR) .................. 10-2013-0039458
Mar. 27, 2014 (KR) .................. 10-2014-0036245

(51) Int. Cl.
| A61K 31/192 | (2006.01) |
| A61K 31/7048 | (2006.01) |
| A61K 36/80 | (2006.01) |
| A61K 31/194 | (2006.01) |
| A23L 33/105 | (2016.01) |

(52) U.S. Cl.
CPC .......... *A61K 31/192* (2013.01); *A23L 33/105* (2016.08); *A61K 31/194* (2013.01); *A61K 31/7048* (2013.01); *A61K 36/80* (2013.01); *A61K 2236/00* (2013.01)

(58) Field of Classification Search
None
See application file for complete search history.

(56) References Cited

FOREIGN PATENT DOCUMENTS

| CN | 1714841 A | * | 1/2006 | .......... A61K 36/804 |
| KR | 10-2006-125499 | | 12/2006 | |
| KR | 10-860080 | | 9/2008 | |
| KR | 10-1476095 | | 12/2014 | |
| WO | 2006129964 A1 | | 12/2006 | |

OTHER PUBLICATIONS

Luo et al., CN 1714841 A, Jan. 2006, machine translation, Retreived on Jun. 29, 2016 from http://worldwide.espacenet.com.*
Barnes P.J. 20014, Mediators of chronic obstructive pulmonary disease, Pharmacol. Rev. 56:515-548.
Dong Soon Kim, Young Sam Kim, Ki-Suck Jung, Jung Hyun Chang, Chae-Man Lim, Jae Ho Lee, Soo-Taek Uh, Jae Jeong Shim, and Woo Jin Lew, Prevalence of Chronic Obstructive Pulmonary Disease in Korea, on behalf of the Korean Academy of Tuberculosis and Respiratory Diseases, Am J Respir Crit Care Med vol. 172. pp. 842-847, 2005.
Don D. Sin and S. F. Paul Man, Chronic Obstructive Pulmonary Disease as a Risk Factor for Cardiovascular Morbidity and Mortality, Proc Am Thorac Soc vol. 2. pp. 8-11, 2005.
A Sonia Buist, Mary Ann McBurnie, William M Vollmer, Suzanne Gillespie, Peter Burney, David M Mannino, Ana M B Menezes, Sean D Sullivan, Todd A Lee, Kevin B Weiss, Robert L Jensen, Guy B Marks, Amund Gulsvik, Ewa Nizankowska-Mogilnicka, International variation in the prevalence of COPD (The BOLD Study): a population-based prevalence study, Lancet, vol. 370;741-750, Sep. 1, 2007.
Barnes PJ (2000b) Mechanisms in COPD: differences from asthma. Chest 117(Suppl): 10S-14S.

(Continued)

*Primary Examiner* — Shaojia Anna Jiang
*Assistant Examiner* — Dale R Miller
(74) *Attorney, Agent, or Firm* — Kirk Hahn

(57) ABSTRACT

A composition comprising a purified extract isolated from *Pseudolysimachion rotundum* var. *subintegrum* containing abundant amount of active ingredient or the compounds isolated therefrom as an active ingredient for treating a chronic obstructive pulmonary disease and the use thereof. Inventive purified extract and compounds showed potent anti-COPD activity without beta-2-receptor agonistic response through various in vivo tests as well as in vitro test. Therefore, it can be used as the therapeutics or functional health food for treating and preventing chronic obstructive pulmonary disease (COPD).

4 Claims, 24 Drawing Sheets

(56) References Cited

OTHER PUBLICATIONS

Saetta M, Turato G, Maestrelli P, Mapp CE, and Fabbri LM (2001) Cellular and structural bases of chronic obstructive pulmonary disease. Am. J. Respir. Crit. Care Med. 163:1304-1309.

Saetta M, Di Stefano A, Turato G, Facchini FM, Corbino L, Mapp CE, Maestrelli P, Ciaccia A, and Fabbri LM (1998) CD8 T-lymphocytes in peripheral airways of smokers with chronic obstructive pulmonary disease. Am. J. Respir. Crit. Care Med. 157:822-826.

Di Stefano A, Capelli A, Lusuardi M, Balbo P, Vecchio C, Maestrelli P, Mapp CE, Fabbri LM, Donner CF, and Saetta M (1998) Severity of airflow limitation is associated with severity of airway inflammation in smokers. Am. J. Respir. Crit. Care Med. 158:1277-1285.

Fabbri L, Beghe B, Caramori G, Papi A, and Saetta M (1998) Similarities and discrepancies between exacerbations of asthma and chronic obstructive pulmonary disease. Thorax 53:803-808.

Fabbri LM, Romagnoli M, Corbetta L, Casoni G, Busljetic K, Turato G, Ligabue G, Ciaccia A, Saetta M, and Papi A (2003) Differences in airway inflammation in patients with fixed airflow obstruction due to asthma or chronic obstructive pulmonary disease. Am. J. Respir. Crit. Care Med. 167:418-424.

Hele Dj, Belvisi MG, 2003. Novel therapies for the treatment of inflammatory airway disease, Expert. Opino. Invest. Drug, 12:5-18.

J Craig Fox and Mary F Fitzgerald; The role of animal models in the pharmacological evaluation of emerging anti-inflammatory agents for the treatment of COPD, Current Opinion in Pharmacology 2009, 9:231-242.

Busse PJ, Zhang TF, Srivastava K, Schofield B, Li XM. 2007. Effect of ageing on pulmonary inflammation, airway hyperresponsiveness and T and B cell responses in antigen-sensitized and -challenged mice. Clinical & Experimental Allergy. 37(9):1392-403.

Smirnova MG, Birchall JP, Pearson JP. 2000. TNF-alpha in the regulation of MUC5AC secretion: some aspects of cytokine-induced mucin hypersecretion on the in vitro model. Cytokine, 12:1732-6.

Blidberg K, Palmberg L, Dahlen B, Lantz AS, Larsson K. 2012. Chemokine release by neutrophils in chronic obstructive pulmonary disease. Innate Immun. 18: 503-510.

International Search Report, PCT/KR2014/003080.

Oh, S.R., et al., Suppressive effect of verproside isolated from Pseudolysimachion longifolium on airway inflammation in a mouse model of allergic asthma, International Immunopharmacology, 2006, 6(6), 978-986.

Park, E.J., et al., Liquid chromatography-mass spectrometry for the simultaneous determination of the the catalpol-related iridoid glucosides, verproside, isovanilloycatalpol, catalposide and 6-O-veratroyl catalpol in rat plasma, Biomedical Chromatography, 2009, 23(9), 980-986.

Certificate of Patent, KR 10-1476095.

English translation of claims in Korean applications and chart showing claim correspondence with US application.

Document showing relationship between Korean Patent KR 10-1476095, Korean application KR 10-2013-0039458 and priority application KR 10-2012-0036245.

* cited by examiner

COMPOSITION COMPRISING A PURIFIED EXTRACT ISOLATED FROM *PSEUDOLYSIMACHION ROTUNDUM* VAR. *SUBINTEGRUM* CONTAINING ABUNDANT AMOUNT OF ACTIVE INGREDIENT OR THE COMPOUNDS ISOLATED THEREFROM, AS AN ACTIVE INGREDIENT FOR TREATING A CHRONIC OBSTRUCTIVE PULMONARY DISEASE AND THE USE THEREOF

This application is a U.S. National Phase under 35 U.S.C. §371 of International Application PCT/KR2014/003080, filed on Apr. 9, 2014, which claims priority to Korean Patent Application No. 10-2014-0036245, filed on Mar. 27, 2014 and Korean Patent Application No. 10-2013-0039458, filed on Apr. 10, 2013. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention relates to a composition comprising a purified extract isolated from *Pseudolysimachion rotundum* var. *subintegrum* containing abundant amount of active ingredient or the compounds isolated therefrom as an active ingredient for preventing or treating a chronic obstructive pulmonary disease and the use thereof.

BACKGROUND ART

Generally, chronic obstructive pulmonary disease (COPD) is one of pulmonary disease caused by abnormal inflammatory disease in lung resulting in the obstruction of respiratory tract. COPD gives rise to dyspnoea resulting from the hindrance from exhausting air flow and shows different characteristics for example, the poor reversibility of an airways limitation or airways obstruction, the progressive development according to elapse time etc, from the common characteristics of asthma and may be classified into a pulmonary emphysema and chronic obstructive bronchitis (Barnes P. J. 20014, Mediators of chronic obstructive pulmonary disease, *Pharmacol. Rev.* 56:515-548).

COPD has been reported as one of risk factor for cardiovascular morbidity and mortality and the fifth leading cause of death worldwide in 2001. The prevalence of chronic obstructive pulmonary disease based on Global Initiative for Chronic Obstructive Lung Disease (GOLD) criteria (a ratio of FEV1 to FVC of less than 0.7) was 17.2% (men, 25.8%; women, 9.6%) among Koreans older than 45 years (Dong Soon Kim, Young Sam Kim, Ki-Suck Jung, Jung Hyun Chang, Chae-Man Lim, Jae Ho Lee, Soo-Taek Uh, Jae Jeong Shim, and Woo Jin Lew, on behalf of the Korean Academy of Tuberculosis and Respiratory Diseases, Am J Respir Crit Care Med Vol 172. pp 842-847, 2005; Don D. Sin and S. F. Paul Man, Chronic Obstructive Pulmonary Disease as a Risk Factor for Cardiovascular Morbidity and Mortality, Proc Am Thorac Soc Vol 2. pp 8-11, 2005; A Sonia Buist, Mary Ann McBurnie, William M Vollmer, Suzanne Gillespie, Peter Burney, David M Mannino, Ana M B Menezes, Sean D Sullivan, Todd A Lee, Kevin B Weiss, Robert L Jensen, Guy B Marks, Amund Gulsvik, Ewa Nizankowska-Mogilnicka, International variation in the prevalence of COPD (The BOLD Study): a population-based prevalence study, Lancet, Vol 370; 741-750, Sep. 1, 2007).

Most patients with COPD have all three pathological mechanisms (chronic obstructive bronchitis, emphysema, and mucus plugging) as all are induced by smoking, but they may differ in the proportion of emphysema and obstructive bronchitis. In developed countries, cigarette smoking is by far the most common cause of COPD, but there are several other risk factors, including air pollution (particularly, indoor air pollution from burning fuels), poor diet, and occupational exposure. COPD is characterized by acceleration in the normal decline of lung function seen with age. The slowly progressive airflow limitation leads to disability and premature death and is quite different from the variable airway obstruction and symptoms in asthma, which rarely progresses in severity.

There have been reported that the pathophysiological action and syndrome of COPD are fundamentally different from those of asthma. Although COPD and asthma both involve inflammation in the respiratory tract, there are marked differences in the nature of the inflammatory process, with differences in inflammatory cells, mediators, response to inflammation, anatomical distribution, and response to anti-inflammatory therapy, for example, (a) in respect to inflammatory cells, mast cell, eosinophils, D4+ cell (Th2), macrophages etc mainly act on the occurrence of asthma whereas neutrophils, CD8+ (Tc) etc mainly act on the occurrence of COPD; (b) in respect to inflammatory mediators, leukotriens B, histamine, IL-4, IL-5, Il-13, eotaxin, RENTES, oxidative stress etc are mainly involved in the occurrence of asthma whereas TNF-alpha, IL-8, GRO-alpha etc are mainly involved in the occurrence of COPD; (c) in respect to inflammatory syndrome, asthma shows different inflammatory syndrome by acting on the overall pulmonary tract at early age, such as AHR (airway hyperresponsiveness), epithelial shedding, fibrosis, no parenchymal involvement, muscus secretion, relatively reversible airways obstruction, cough, sneezing, dyspnea etc from that of COPD, which occurs by acting on peripheral airways at adults and shows various phenomena such as, epithelial metaplasia, parenchymal destruction, relatively irreversible airways obstruction, chronic bronchitis, emphysema etc (Barnes P J (2000b) Mechanisms in COPD: differences from asthma. *Chest* 117(Suppl): 10S-14S.; Saetta M, Turato G, Maestrelli P, Mapp C E, and Fabbri L M (2001) Cellular and structural bases of chronic obstructive pulmonary disease. *Am. J. Respir. Crit. Care Med.* 163:1304-1309).

Histopathological studies on COPD show a predominant involvement of peripheral airways (bronchioles) and lung parenchyma, whereas asthma involves inflammation in all airways but without involvement of the lung parenchyma. There is obstruction of bronchioles, with fibrosis and infiltration with macrophages and T lymphocytes. There is destruction of lung parenchyma, as well as an increased number of macrophages and CD8(cytotoxic) T lymphocytes (Saetta M, Di Stefano A, Turato G, Facchini F M, Corbino L, Mapp C E, Maestrelli P, Ciaccia A, and Fabbri L M (1998) CD8T-lymphocytes in peripheral airways of smokers with chronic obstructive pulmonary disease. *Am. J. Respir. Crit. Care Med.* 157:822-826.). Bronchial biopsies show similar changes with an infiltration of macrophages and CD8 cells and an increased number of neutrophils in patients with severe COPD (Di Stefano A, Capelli A, Lusuardi M, Balbo P, Vecchio C, Maestrelli P, Mapp C E, Fabbri L M, Donner C F, and Saetta M (1998) Severity of airflow limitation is associated with severity of airway inflammation in smokers. *Am. J. Respir. Crit. Care Med.* 158:1277-1285.).

In contrast to asthma, eosinophils are not prominent except during exacerbations or when patients have concomitant asthma (Fabbri L, Beghe B, Caramori G, Papi A, and Saetta M (1998) Similarities and discrepancies between exacerbations of asthma and chronic obstructive pulmonary disease. *Thorax* 53:803-808; Fabbri L M, Romagnoli M, Corbetta L, Casoni G, Busljetic K, Turato G, Ligabue G, Ciaccia A, Saetta M, and Papi A (2003) Differences in airway inflammation in patients with fixed airflow obstruction due to asthma or chronic obstructive pulmonary disease. *Am. J. Respir. Crit. Care Med.* 167:418-424.).

Accordingly, the therapeutic approach of Chronic obstructive pulmonary disease (COPD) shall be different from that of asthma, however, the present therapy has been focused on treating non-specifically both of diseases. Therefore, there have been no anti-inflammatory therapies specifically approved for COPD and the available anti-inflammatory therapies were originally developed for asthma. The challenges facing research in COPD are multi-faceted; the mechanisms underlying the complex and heterogeneous pathology of this disease require unravelling; the role of inflammation in disease progression needs to be confirmed. (Hele Dj, Belvisi M G, 2003. Novel therapies for the treatment of inflammatory airway disease, Expert. Opino. Invest. Drug, 12:5-18; J Craig Fox and Mary F Fitzgerald; The role of animal models in the pharmacological evaluation of emerging anti-inflammatory agents for the treatment of COPD, Current Opinion in Pharmacology 2009, 9:231-242).

Improvements to the current therapy available to treat asthma in the form of longer acting beta-agonists, safer steroids and combination therapies are ongoing and for COPD anti-cholinergics provide symptomatic relief. Steroids have been utilised to treat exacerbations, but as yet, no treatment has been shown to impact significantly on the progressive decline in lung function in COPD or the development of asthma.

Accordingly, there have been much studied to develop new drugs with potential to successfully and specifically treat COPD till now.

The present inventors have been focused to develop potent treating agent derived from natural resources with safety and efficacy such as plant, animals etc having potent inhibiting activity from the reproduction of inflammatory cells and finally, have found that the extract of *Pseudolysimachion longifolium* showed potent anti-inflammatory, anti-allergy and anti-asthma activity (Korean Patent No. 10-860080) and various compounds isolated therefrom such as, verproside (6-O-3,4-dihydroxybenzoyl catalpol), picroside II (6-O-4-hydroxy-3-methoxybenzoyl catalpol), verminoside (6-O-3,4-Dihydroxy cinnamoyl catalpol), 6-O-veratroyl catalpol (6-O-3,4-Dimethoxy benzoyl catalpol), minecoside (6-O-3-hydroxy-4-methoxycinnamoyl catalpol), catalpol and the like, also showed potent anti-inflammatory, anti-allergy and anti-asthma activity (Korean Patent Publication No. 10-2006-125499).

*Pseudolysimachion rotundum* var *subintegrum*, is a perennial herb distributed in Korea, China, Japan, Ostrov Sakhalin, and Russia.

Based on the previous studies on the anti-inflammatory, anti-allergy and anti-asthma activity of the extract of *Pseudolysimachion longifolium* disclosed in Korean Patent No. 10-860080, the present inventors have tried to develop more efficient method for preparing more potent and more abundant ingredients showing anti-inflammatory, anti-allergy and anti-asthma activity isolated from the extract of *Pseudolysimachion rotundum* var *subintegrum*.

However, there has been not reported or disclosed about the efficient method for preparing more potent and more abundant ingredients or the compounds isolated from the extract of *Pseudolysimachion rotundum* var *subintegrum* showing potent and specific anti-COPD activity than those in the above cited literatures, the disclosures of which are incorporated herein by reference.

Accordingly, the present inventors have found the novel industrialized method for preparing purified extract containing more abundant active ingredients such as catalpol derivatives from the extract of *Pseudolysimachion rotundum* var *subintegrum* and the purified extract or the compounds isolated therefrom showed potent anti-COPD activity without beta-2-receptor agonistic response through various in vivo tests using by BALB/c male mice, for example, an inhibition test on the proliferation and activity of inflammatory immunocyte and neutrophil recruiting to lung caused by COPD occurrence; an inhibition test on the reproduction of chemokines involved in the breakdown of pneumocyte, such as MIP-2/CXCL-2, TNF-alpha, KC/CXCL-1 (Chemokines Gro-alpha) and CXCL-8 etc; the reducing effect on the release of IL-1 beta, IL-6, TNF-alpha and MMP-9 expression by decreasing NF-kappaB activation in animal test using by SPF (specific pathogen-free) Sprague-Dawley rat, as well as in vitro test, for example, an inhibition test on the expression of MUC5AC (oligomeric muscus/gel-forming), inducing effect on the IL-4-expression of Th2 cell in molecular expression profiling change test etc.

DISCLOSURE

Technical Problem

The present invention provides a pharmaceutical composition and a health food comprising the novel purified extract containing active ingredients such as catalpol derivatives from *Pseudolysimachion rotundum* var *subintegrum* or at least one compounds selected from the group consisiting of veratric acid, verproside, catalposide, picroside II, isovanilloyl catalpol and 6-O-veratroyl catalpol to treat and prevent chronic obstructive pulmonary disease (COPD).

The present invention also provides a use of the novel purified extract containing active ingredients such as catalpol derivatives from *Pseudolysimachion rotundum* var *subintegrum* or at least one compounds selected from the group consisting of veratric acid, verproside, catalposide, picroside II, isovanilloyl catalpol and 6-O-veratroyl catalpol to treat and prevent chronic obstructive pulmonary disease (COPD).

The present invention also provides a method of treating or preventing chronic obstructive pulmonary disease (COPD) in a mammal comprising administering to said mammal an effective amount of the novel purified extract containing active ingredients such as catalpol derivatives from *Pseudolysimachion rotundum* var *subintegrum* or at least one compounds selected from the group consisiting of veratric acid, verproside, catalposide, picroside II, isovanilloyl catalpol and 6-O-veratroyl catapol, together with a pharmaceutically acceptable carrier thereof.

Technical Solution

Accordingly, it is an object of the present invention to provide a pharmaceutical composition or a health functional food comprising the novel purified extract containing active ingredients such as catalpol derivatives from *Pseudolysima-*

*chion rotundum* var *subintegrum* or at least one compounds selected from the group consisting of veratric acid, verproside, catalposide, picroside II, isovanilloyl catalpol and 6-O-veratroyl catalpol to treat or prevent chronic obstructive pulmonary disease (COPD).

The term "catalpol derivatives" disclosed herein comprises verproside, catalposide, picroside II, isovanilloyl catalpol and 6-O-veratroyl catalpol etc.

The term "*Pseudolysimachion rotundum* var *subintegrum*" disclosed herein comprises the cultivated or naturally grown plant and commercially available plant, but not intended to limit thereto herein.

The term "novel purified extract" disclosed herein comprises (a) the purified extract fractionated with butanol (designated as "ATC1" hereinafter) and (b) the purified extract with the secondary fractionation (designated as "ATC2" hereinafter).

Specifically, the term "the purified extract fractionated with butanol (ATC1)" is characterized by containing 15-50% (w/w) verproside, 0.3-10% (w/w) veratric acid, 0.5-10% (w/w) catalposide, 0.3-10% (w/w) picroside II, 0.3-10% (w/w) isovanilloyl catalpol and 0.3-10% (w/w) 6-O-veratroyl catalpol based on the weight of total extract (100%) of *Pseudolysimachion rotundum* var *subintegrum*; preferably, 20-25% (w/w) verproside, 0.5-5% (w/w) veratric acid, 1-5% (w/w) catalposide, 0.5-5% (w/w) picroside II, 0.5-5% (w/w) isovanilloyl catalpol and 1-5% (w/w) 6-O-veratroyl catalpol based on the weight of total extract (100%) of *Pseudolysimachion rotundum* var *subintegrum*; and/or characterized by containing 12.3-47% (w/w) catalpol derivative in total extract (100%) of *Pseudolysimachion rotundum* var *subintegrum* and having the relative mixed ratio (w/w) between the weight of each catalpol derivative, of 15.0-18.0 parts (w/w) verproside, 2.10-2.60 parts (w/w) catalposide, 1 part (w/w) picroside II, 1.00-1.30 parts (w/w) isovanilloyl catalpol and 2.00-2.30 parts (w/w) 6-O-veratroyl catalpol; preferably, 16.0-17.0 parts (w/w) verproside, 2.20-2.50 parts (w/w) catalposide, 1 part (w/w) picroside II, 1.10-1.20 parts (w/w) isovanilloyl catalpol and 2.10-2.20 parts (w/w) 6-O-veratroyl catalpol; more preferably, 16.20-16.99 parts (w/w) verproside, 2.40-2.45 parts (w/w) catalposide, 1 part (w/w) picroside II, 1.10-1.19 parts (w/w) isovanilloyl catalpol and 2.10-2.19 parts (w/w) 6-O-veratroyl catalpol.

More specifically, the term "the purified extract fractionated with butanol (ATC1)" is characterized by being prepared by the process of; adding at least one extracting solvent selected from water, C1-C4 lower alcohol such as methanol, ethanol, butanol etc or the mixtures thereof, preferably, mixture of water and ethanol, more preferably, 30-80% (w/w) ethanol in water to dried *Pseudolysimachion rotundum* var *subintegrum* at the 1st step; subjecting to at least one extraction method selected from reflux extraction with hot water, cold water extraction, ultra-sonication or conventional extraction, preferably cold water extraction followed by reflux extraction at the temperature ranging from 10 to 100° C., preferably from 20 to 90° C., for the period ranging from 30 mins to 72 hours, preferably, 6 to 48 hours, more preferably, cold water extraction at the temperature ranging from 10 to 60° C., preferably from 20 to 50° C., for the period ranging from 30 mins to 72 hours, preferably, 6 to 48 hours and then reflux extraction at the temperature ranging from 40 to 120° C., preferably from 60 to 90° C., for the period ranging from 30 mins to 72 hours, preferably, 6 to 48 hours, repeatedly, to afford the 1st extract at 2nd step; suspending the 1st extract in about 0.5-10 fold volume (v/v), preferably, about 1-5 fold volume (v/v) of water to afford suspended extract at 3rd step; and adding about 0.5-20 fold volume (v/v), preferably, about 1-10 fold volume (v/v) of butanol, fractionating into water layer and butanol layer and collecting the butanol layer to afford the purified extract fractionated with butanol (ATC1) containing 15-50% (w/w) verproside, 0.3-10% (w/w) veratric acid, 0.5-10% (w/w) catalposide, 0.3-10% (w/w) picroside II, 0.3-10% (w/w) isovanilloyl catalpol and 0.3-10% (w/w) 6-O-veratroyl catalpol based on the weight of total extract (100%) of *Pseudolysimachion rotundum* var *subintegrum* to treat and prevent chronic obstructive pulmonary disease (COPD).

Accordingly, in an another embodiment of the present invention, the present invention also provides a method for preparing the purified extract fractionated with butanol (ATC1) isolated from *Pseudolysimachion rotundum* var *subintegrum* comprising the steps of; adding at least one extracting solvent selected from water, C1-C4 lower alcohol such as methanol, ethanol, butanol etc or the mixtures thereof, preferably, mixture of water and ethanol, more preferably, 30-80% (w/w) ethanol in water to dried *Pseudolysimachion rotundum* var *subintegrum* at the 1st step; subjecting to at least one extraction method selected from reflux extraction with hot water, cold water extraction, ultra-sonication or conventional extraction, preferably cold water extraction followed by reflux extraction at the temperature ranging from 10 to 100° C., preferably from 20 to 90° C., for the period ranging from 30 mins to 72 hours, preferably, 6 to 48 hours, more preferably, cold water extraction at the temperature ranging from 10 to 60° C., preferably from 20 to 50° C., for the period ranging from 30 mins to 72 hours, preferably, 6 to 48 hours and then reflux extraction at the temperature ranging from 40 to 120° C., preferably from 60 to 90° C., for the period ranging from 30 mins to 72 hours, preferably, 6 to 48 hours, repeatedly, to afford the 1st extract at 2nd step; suspending the 1st extract in about 0.5-10 fold volume (v/v), preferably, about 1-5 fold volume (v/v) of water to afford suspended extract at 3rd step; and adding about 0.5-20 fold volume (v/v), preferably, about 1-10 fold volume (v/v) of butanol, fractionating into water layer and butanol layer and collecting the butanol layer to afford the purified extract fractionated with butanol (ATC1) containing 15-50% (w/w) verproside, 0.3-10% (w/w) veratric acid, 0.5-10% (w/w) catalposide, 0.3-10% (w/w) picroside II, 0.3-10% (w/w) isovanilloyl catalpol and 0.3-10% (w/w) 6-O-veratroyl catalpol based on the weight of total extract (100%) of *Pseudolysimachion rotundum* var *subintegrum* to treat and prevent chronic obstructive pulmonary disease (COPD).

Specifically, the term "the purified extract with the secondary fractionation (ATC2)" is characterized by containing 30-60% (w/w) verproside, 0.5-10% (w/w) veratric acid, 2-20% (w/w) catalposide, 1-10% (w/w) picroside II, 1-10% (w/w) isovanilloyl catalpol and 2-20% (w/w) 6-O-veratroyl catalpol based on the weight of total extract (100%) of *Pseudolysimachion rotundum* var *subintegrum*; preferably, 40-50% (w/w) verproside, 1-5% (w/w) veratric acid, 3-10% (w/w) catalposide, 2-5% (w/w) picroside II, 2-8% (w/w) isovanilloyl catalpol and 3-8% (w/w) 6-O-veratroyl catalpol based on the weight of total extract (100%) of *Pseudolysimachion rotundum* var *subintegrum*; and/or characterized by containing 36.5-91% (w/w) catalpol derivative in total extract (100%) of *Pseudolysimachion rotundum* var *subintegrum* and having the relative mixed ratio (w/w) between the weight of each catalpol derivative, of 13.0-16.0 parts (w/w) verproside, 2.20-2.50 parts (w/w) catalposide, 1 part (w/w) picroside II, 1.10-1.40 parts (w/w) isovanilloyl catalpol and 2.00-2.20 parts (w/w) 6-O-veratroyl catalpol; preferably, 14.0-15.0 parts (w/w) verproside, 2.30-2.45 parts (w/w) catalposide, 1 part (w/w) picroside II, 1.20-1.35 parts (w/w) isovanilloyl catalpol and 2.00-2.10 parts (w/w) 6-O-veratroyl catalpol; more preferably, 14.50-14.99 parts (w/w) verproside, 2.35-2.43 parts (w/w) catalposide, 1 part (w/w) picroside II, 1.25-1.34 parts (w/w) isovanilloyl catalpol and 2.01-2.09 parts (w/w) 6-O-veratroyl catalpol.

More specifically, the term "the purified extract with the secondary fractionation (ATC2)" is characterized by being prepared by the process of adding at least one extracting solvent selected from water, C1-C4 lower alcohol such as methanol, ethanol, butanol etc or the mixtures thereof, preferably, mixture of water and ethanol, more preferably, 30-80 (w/w) ethanol in water to dried *Pseudolysimachion rotundum* var *subintegrum* at the 1st step; subjecting to at least one extraction method selected from reflux extraction with hot water, cold water extraction, ultra-sonication or conventional extraction, preferably cold water extraction followed by reflux extraction at the temperature ranging from 10 to 100° C., preferably from 20 to 90° C., for the period ranging from 30 mins to 72 hours, preferably, 6 to 48 hours, more preferably, cold water extraction at the temperature ranging from 10 to 60° C., preferably from 20 to 50° C., for the period ranging from 30 mins to 72 hours, preferably, 6 to 48 hours and then reflux extraction at the temperature ranging from 40 to 120° C., preferably from 60 to 90° C., for the period ranging from 30 mins to 72 hours, preferably, 6 to 48 hours, repeatedly, to afford the 1st extract at 2nd step; suspending the 1st extract in about 0.5-10 fold volume (v/v), preferably, about 1-5 fold volume (v/v) of water to afford suspended extract at 3rd step; adding about 0.5-20 fold volume (v/v), preferably, about 1-10 fold volume (v/v) of butanol, fractionating into water layer and butanol layer and collecting the butanol layer to afford the purified extract fractionated with butanol (ATC1) at the 3rd step; and subjecting the purified extract fractionated with butanol (ATC1) to at least one purification process selected from the group consisting of reverse phase partition chromatography, normal phase partition chromatography, ion exchange chromatography, and size exclusion chromatography to afford the purified extract with the secondary fractionation (ATC2) containing 30-60% (w/w) verproside, 0.5-10% (w/w) veratric acid, 2-20% (w/w) catalposide, 1-10% (w/w) picroside II, 1-10% (w/w) isovanilloyl catalpol and 2-20% (w/w) 6-O-veratroyl catalpol based on the weight of total extract (100%) of *Pseudolysimachion rotundum* var *subintegrum* to treat or prevent chronic obstructive pulmonary disease (COPD).

Accordingly, in an another embodiment of the present invention, the present invention also provides a method for preparing the purified extract with the secondary fractionation (ATC2) isolated from *Pseudolysimachion rotundum* var *subintegrum* comprising the steps of; adding at least one extracting solvent selected from water, C1-C4 lower alcohol such as methanol, ethanol, butanol etc or the mixtures thereof, preferably, mixture of water and ethanol, more preferably, 30-80% (w/w) ethanol in water to dried *Pseudolysimachion rotundum* var *subintegrum* at the 1st step; subjecting to at least one extraction method selected from reflux extraction with hot water, cold water extraction, ultra-sonication or conventional extraction, preferably cold water extraction followed by reflux extraction at the temperature ranging from 10 to 100° C., preferably from 20 to 90° C., for the period ranging from 30 mins to 72 hours, preferably, 6 to 48 hours, more preferably, cold water extraction at the temperature ranging from 10 to 60° C., preferably from 20 to 50° C., for the period ranging from 30 mins to 72 hours, preferably, 6 to 48 hours and then reflux extraction at the temperature ranging from 40 to 120° C., preferably from 60 to 90° C., for the period ranging from 30 mins to 72 hours, preferably, 6 to 48 hours, repeatedly, to afford the 1st extract at 2nd step; suspending the 1st extract in about 0.5-10 fold volume (v/v), preferably, about 1-5 fold volume (v/v) of water to afford suspended extract at 3rd step; adding about 0.5-20 fold volume (v/v), preferably, about 1-10 fold volume (v/v) of butanol, fractionating into water layer and butanol layer and collecting the butanol layer to afford the purified extract fractionated with butanol (ATC1) at the 3rd step; and subjecting the purified extract fractionated with butanol (ATC1) to at least one further purification process selected from the group consisting of reverse phase partition chromatography, normal phase partition chromatography, ion exchange chromatography, and size exclusion chromatography to afford the purified extract with the secondary fractionation (ATC2) containing 30-60% (w/w) verproside, 0.5-10% (w/w) veratric acid, 2-20% (w/w) catalposide, 1-10% (w/w) picroside II, 1-10% (w/w) isovanilloyl catalpol and 2-20% (w/w) 6-O-veratroyl catalpol based on the weight of total extract (100%) of *Pseudolysimachion rotundum* var *subintegrum* to treat or prevent chronic obstructive pulmonary disease (COPD).

Specifically, the term "further purification process" is selected from (i) reverse phase partition chromatography, (ii) normal phase partition chromatography, (iii) ion exchange chromatography or (iv) size exclusion chromatography, preferably, reverse phase partition chromatography or any chromatography using by any resin as a stationary phase which can retain non-polar substance while eluting polar substance, for example, Sephadex resin such as Sephadex, Sephadex LH20, Sephadex G-25, Sephadex G-10, Sepharose, Superdex, methylacrylate resin, carboxymethyl cellulose, sulphopropyl cellulose, carboxymethyl Sephadex, sulphopropyl Sephadex, carboxymethyl Sepharose, sulphopropyl Sepharose and the like; reverse polymer resin using by Stylene-divinylbenzen co-polymer such as Polymer X, HP20, PRP-h1 Polymer and the like or Methacrylate support resin etc; normal Silica gel such as BPC (Bonded phase chromatography) product, Silica product procured from YMC Co. Ltd, Silica product procured from DAISO Co. Ltd, Silica product procured from ASAHI Co. Ltd, Silica product procured from COSMOSYL Co. Ltd and the like; ODS product used for HPLC filler such as ODS product procured from YMC Co. Ltd, ODS product procured from DAISO Co. Ltd, ODS product procured from ASAHI Co. Ltd, ODS product procured from CHEMCO Co. Ltd, ODS product procured from Merck Co. Ltd ODS product procured from COSMOSYL Co. Ltd ODS product procured from FUJI Co. Ltd and the like.

In a preferred embodiment adopting (i) reverse phase partition chromatography as a further purification process of the present invention, the "stationary phase in the above-described reverse phase partition chromatography" may be any stationary phases such as reverse phase substance as a stationary phase which can retain non-polar substance while eluting polar substance, preferably, Silica gel based stationary phase, polymer based stationary phase such as polystyrene etc and the like, more preferably, Silica gel derivatives such as C2, C4, C6, C8, C10, C12, 14, C16, C18 and the like; or a polymer based stationary phase such as PS-2, Oasis HLB and the like, more and more preferably, reverse phase Silica gel (C18(IV)-D), ODS-A/ODS-AQ product from YMC Co. Ltd., SP-C-ODS product from CHEMCO Co.

Ltd., SP-ODS-RPS product from DAISO Co. Ltd., 5C18 product from COSMOSYL Co. Ltd., Chromatorex product from FUJI Co. Ltd., etc.

In a preferred embodiment adopting (i) reverse phase partition chromatography as a further purification process of the present invention, the "mobile phase in the above-described (i) reverse phase partition chromatography" may be at least one solvent selected from water, acetonitrile, lower alcohol such as methanol, ethanol, butanol etc, tetrahydrofuran (THF) or the mixture thereof, preferably, water, lower alcohol such as methanol, ethanol, butanol etc, or the mixture thereof, more preferably, the mixture solvent of water and methanol, more and more preferably, the mixture solvent of water and methanol with starting from 90:10 (v/v) to 60:40 (v/v) to elute polar substance.

In a preferred embodiment adopting (ii) normal phase partition chromatography as a further purification process of the present invention, the "stationary phase in the above-described normal phase partition chromatography" may be any stationary phases such as normal phase substance as a stationary phase which can retain polar substance while eluting non-polar substance, preferably, Silica gel, Fluorosyl, or alumina based stationary phase, CN, Diol, or NH2 moiety polymer based stationary phase and the like, more preferably, Silica gel, Fluorosyl, or alumina based stationary phase, etc.

In a preferred embodiment adopting (ii) normal phase partition chromatography as a further purification process of the present invention, the "mobile phase in the above-described (ii) normal phase partition chromatography" may be at least one solvent selected from hexane, heptane, ethylacetate, ethanol, diethylether, 2-propanol or the mixture thereof, preferably, hexane, heptane, ethylacetate or the mixture thereof to elute non-polar substance.

In a preferred embodiment adopting (iii) ion exchange chromatography as a further purification process of the present invention, the "stationary phase in the above-described (iii) ion exchange chromatography" may be any high molecular stationary phases as a stationary phase which have charged cross-linking moiety, preferably, cation exchange resin, anion exchange resin, or synthetic adsorbent, and the like, more preferably, strongly acidic cation exchange resin such as AG 50W-x8, Amberlite IR-120, Dowex 60W-x8, SKIB etc; weakly acidic cation exchange resin such as Amberlite IRA-67, Dowex 3-x4A etc; strongly basic cation exchange resin such as DIAION SKIB, DIAION PK216, DIAION CR20, DIAION UBK555 (Mitsubishi Chemical Co.), TRILITE SPC 160H, TRILITE SPC 180H, TRILITE SPC 400JH (Samyang Co. Ltd.), AMBERLITE 200C Na, AMBERLITE CG50, AMBERLITE CR1310 Na, AMBERJET 200H, AMBERLYST 131 WET, ALBERLYST 232 WET (ROHM and HAAS Co. Ltd.), Lewatit VP OC 1800, Lewatit VP OC 1812, Lewatit MDS1368 Na, Lewaitit K1221 (Bayer Co. Ltd.), PUROLITE PCR833CA, PUROLITE C145 (Purolite Co. Ltd.), MFG210, MFG 250 (Finex Co. Ltd.) etc; strongly basic anion exchange resin such as SA11A, SA20A, SA21A etc; or CaptoQ (GE Healthcare Co. Ltd.), or the resin having similar property thereto such as Toyopearl QEA (Tosoh Co. Ltd.), Q Sepharose FF (GE Healthcare Co. Ltd.), Fractogel EMD, Fractogel TMAE, Fractogel HICAP (Merck KGaA Co. Ltd or Darmstadt Co. Ltd.); more and more preferably, SA21A; adsorbent such as SP207, HP20SS, HP20 etc, more preferably, HP 20.

In a preferred embodiment adopting (iv) size exclusion chromatography as a further purification process of the present invention, the "stationary phase in the above-described (iv) size exclusion chromatography" may be any gel type stationary phases as a stationary phase which can separate by the size of sample, preferably, dextran-based gel such as sephadex (for example, sephadex G-25), polyacrylamide-based gel such as Sephacryl (for example, Sephacryl-S400), Agarose-based gel such as Superose or Sepharose (for example, Sepharose CL-4B) or the combinations thereof such as Superdex 200 combination Dextran (For example, Sephadex™), or cross-linked Agarose gel (Superose™) and the like, however it shall be not limited thereto herein. The "mobile phase in the above-described (iv) size exclusion chromatography" may be buffer solution selected from the group consisting of sodium acetate buffer, sodium phosphate buffer, ammonium acetate buffer, MES (2-(N-morpholino)ethanesulphonic acid), Bis-Tris[2-Bis(2-hydroxyethyl)amino-2-(hydroxymethyl)-1,3-propandiol],
ADA [N-(2-acetamido)iminodiacetate), PIPES [piperaxine-N,N'-Bis(2-ethanesulophonic acid)], BES [N.N'-Bis(2-hydroxyethyl)-2-aminoethansulphonic acid), MOPS [3-(N-morpholino)propansulphonic acid)], TES (N-Tris (hydroxymethyl)methyl-2-aminoethanesulphonic acid], HEPES [N-2-hydroxyethyl-piperazine-N'-2-ethanesulphonic acid), and the like; preferably, sodium acetate buffer, sodium phosphate buffer, or ammonium acetate buffer.

In a preferred embodiment of the present invention, the present invention can also perform (v) Gel permeation chromatography or Gel filtration chromatography in addition to (i) reverse phase partition chromatography, (ii) normal phase partition chromatography, (iii) ion exchange chromatography, (iv) size exclusion chromatography or the combination thereof, as a further purification process disclosed herein.

The present invention also provides novel purified extract such as (a) the purified extract fractionated with butanol (designated as "ATC1" hereinafter) or (b) the purified extract with the secondary fractionation (designated as "ATC2" hereinafter) prepared by the above-described preparation methods.

The present invention also provides novel purified extract fractionated with butanol (ATC1) from the extract of *Pseudolysimachion rotundum* var *subintegrum*, prepared by the above-described preparation methods, which contains 12.3-47% (w/w) catalpol derivative in total extract (100%) of *Pseudolysimachion rotundum* var *subintegrum* wherein said catalposide derivatives consist of 15-50% (w/w) verproside, 0.3-10% (w/w) veratric acid, 0.5-10% (w/w) catalposide, 0.3-10% (w/w) picroside II, 0.3-10% (w/w) isovanilloyl catalpol and 0.3-10% (w/w) 6-O-veratroyl catalpol, preferably, 20-25% (w/w) verproside, 0.5-5% (w/w) veratric acid, 1-5% (w/w) catalposide, 0.5-5% (w/w) picroside II, 0.5-5% (w/w) isovanilloyl catalpol and 1-5% (w/w) 6-O-veratroyl catalpol based on the weight of total extract (100%) of *Pseudolysimachion rotundum* var *subintegrum*.

The present invention also provides novel purified extract fractionated with butanol (ATC1) from the extract of *Pseudolysimachion rotundum* var *subintegrum*, prepared by the above-described preparation methods, which shows the relative mixed ratio (w/w) between the weight of each catalposide derivative of 15.0-18.0 (w/w) verproside, 2.10-2.60 (w/w) catalposide, 1 (w/w) picroside II, 1.00-1.30 (w/w) isovanilloyl catalpol and 2.00-2.30 (w/w) 6-O-veratroyl catalpol; preferably, 16.0-17.0 (w/w) verproside, 2.20-2.50 (w/w) catalposide, 1 (w/w) picroside II, 1.10-1.20 (w/w) isovanilloyl catalpol and 2.10-2.20 (w/w) 6-O-veratroyl catalpol; more preferably, 16.20-16.99 (w/w) verproside, 2.40-2.45 (w/w) catalposide, 1 (w/w) picroside II, 1.10-1.19 (w/w) isovanilloyl catalpol and 2.10-2.19 (w/w) 6-O-veratroyl catalpol.

The present invention also provides novel purified extract with the secondary fractionation (ATC2) from the extract of *Pseudolysimachion rotundum* var *subintegrum*, prepared by the above-described preparation methods, which contains 36.5-91% (w/w) catalpol derivative in total extract (100%) of *Pseudolysimachion rotundum* var *subintegrum*, wherein said catalpol derivative consist of 30-60% (w/w) verproside, 0.5-10% (w/w) veratric acid, 2-20% (w/w) catalposide, 1-10% (w/w) picroside II, 1-10% (w/w) isovanilloyl catalpol and 2-20% (w/w) 6-O-veratroyl catalpol based on the weight of total extract (100%) of *Pseudolysimachion rotundum* var *subintegrum*; preferably, 40-50% (w/w) verproside, 1-5% (w/w) veratric acid, 3-10% (w/w) catalposide, 2-5% (w/w) picroside II, 2-8% (w/w) isovanilloyl catalpol and 3-8% (w/w) 6-O-veratroyl catalpol based on the weight of total extract (100%) of *Pseudolysimachion rotundum* var *subintegrum*.

The present invention also provides novel purified extract with the secondary fractionation (ATC2) from the extract of *Pseudolysimachion rotundum* var *subintegrum*, prepared by the above-described preparation methods, which show the relative mixed ratio (w/w) between the weight of each catalpol derivative, of 13.0-16.0 (w/w) verproside, 2.20-2.50 (w/w) catalposide, 1 (w/w) picroside II, 1.10-1.40 (w/w) isovanilloyl catalpol and 2.00-2.20 (w/w) 6-O-veratroyl catalpol; preferably, 14.0-15.0 (w/w) verproside, 2.30-2.45 (w/w) catalposide, 1 (w/w) picroside II, 1.20-1.35 (w/w) isovanilloyl catalpol and 2.00-2.10 (w/w) 6-O-veratroyl catalpol; more preferably, 14.50-14.99 (w/w) verproside, 2.35-2.43 (w/w) catalposide, 1 (w/w) picroside II, 1.15-1.24 (w/w) isovanilloyl catalpol and 2.01-2.09 (w/w) 6-O-veratroyl catalpol.

The term "purified extract" disclosed herein may be used as a dried form prepared by the vacuum evaporation method, freeze dry method or hot-air drying method etc.

The term "prevent" disclosed herein comprises any act to inhibit or postpone the occurrence of certain disease or disorder disclosed herein by way of administrating the inventive composition; and the term "treat" disclosed herein comprises any act to alleviate or favorably changing the symptom associated with certain disease or disorder disclosed herein by way of administrating the inventive composition.

The present inventors have found that the novel industrialized method for preparing purified extract can provide more abundant active ingredients, i.e., 36.5% to 91.0% (w/w) such as catalpol derivatives from the extract of *Pseudolysimachion rotundum* var *subintegrum* comparing with the crude extract prepared by the conventional method disclosed in the prior art wherein the content of catalpol derivatives in only 8.49% (w/w) through various HPLC analyses, for example, the inventive purified extract (ATC1) contains 17.60% (w/w) verproside, 0.72% (w/w) veratric acid, 2.62% (w/w) catalposide, 1.08% (w/w) picroside II, 1.26% (w/w) isovanilloyl catalpol and 2.36% (w/w) 6-O-veratroyl catalpol (See Example 2) and the inventive purified extract (ATC2) contains 43.83% (w/w) verproside, 1.80% (w/w) veratric acid, 7.07% (w/w) catalposide, 2.93% (w/w) picroside II, 3.85% (w/w) isovanilloyl catalpol and 6.15% (w/w) 6-O-veratroyl catalpol while the crude extract (CX) prepared by the conventional method disclosed in the prior art contains only 5.9% (w/w) verproside, 0.21% (w/w) veratric acid, 0.82% (w/w) catalposide, 0.40% (w/w) picroside II, 0.42% (w/w) isovanilloyl catalpol and 0.74% (w/w) 6-O-veratroyl catalpol based on the weight of total extract (100%) of *Pseudolysimachion rotundum* var *subintegrum*; crude extract; as well as the purified extract or the compounds isolated therefrom showed potent anti-COPD activity without beta-2-receptor agonistic response through various in vivo tests using by BALB/c male mice, for example, an inhibition test on the proliferation and activity of inflammatory immunocyte and neutrophil recruiting to lung caused by COPD occurrence; an inhibition test on the reproduction of chemokines involved in the breakdown of pneumocyte, such as MIP-2/CXCL-2, TNF-alpha, KC/CXCL-1 (Chemokines Gro-alpha) and CXCL-8 etc; the reducing effect on the release of IL-1 beta, IL-6, TNF-alpha and MMP-9 expression by decreasing NF-kappaB activation in animal test using by SPF (specific pathogen-free) Sprague-Dawley rat, as well as in vitro test, for example, an inhibition test on the expression of MUC5AC (oligomeric muscus/gel-forming), inducing effect on the IL-4-expression of Th2 cell in molecular expression profiling change test etc.

The present inventors have also found that the maximized combined weight ratio between veratric acid, verproside, catalposide, picroside II, isovanilloyl catalpol and 6-0-veratroyl catalpol to treat and prevent chronic obstructive pulmonary disease (COPD), i.e., verproside (ATC1-68.6%; ATC2-66.8%. calculated content range based on the total weight of the compounds: 45-90 w/w %), veratric acid (ATC1-2.8%; ATC2-2.7%. calculated content range based on the total weight of the compounds: 1.5-4.0 w/w %), catalposide (ATC1-10.2%; ATC2-10.8%. calculated content range based on the total weight of the compounds: 7.0-14.0 w/w %), picroside II (ATC1-4.2%; ATC2-4.5%. calculated content range based on the total weight of the compounds: 3.0-6.0 w/w %), isovanilloyl catalpol (ATC1-4.9%; ATC2-5.8%. calculated content range based on the total weight of the compounds: 3.0-8.0 w/w %) and 6-O-veratroyl catalpol (ATC1-9.2%; ATC2-9.4%. calculated content range based on the total weight of the compounds: 6.0-12.0 w/w %).

Accordingly, in accordance with the other aspect of the present invention, present invention provide a pharmaceutical composition or a health functional food comprising the combined compounds with mixed weight ratio of 40-93% verproside, 1.0-10% veratric acid, 2.0-25% catalposide, 1.0-15% picroside II, 1.0-15% isovanilloyl catalpol and 2.0-25% 6-O-veratroyl catalpol, preferably, 45-90% verproside, 1.0-7.0% veratric acid, 3.0-15% catalposide, 2.0-10% picroside II, 2.0-10% isovanilloyl catalpol and 2.0-15% 6-O-veratroyl catalpol to treat or prevent chronic obstructive pulmonary disease (COPD).

Present invention provide a pharmaceutical composition or a health functional food comprising the combined compounds with mixed weight ratio of 40-93% verproside, 1.0-10% veratric acid, 2.0-25% catalposide, 1.0-15% picroside II, 1.0-15% isovanilloyl catalpol and 2.0-25% 6-O-veratroyl catalpol, preferably, 45-90% verproside, 1.0-7.0% veratric acid, 3.0-15% catalposide, 2.0-10% picroside II, 2.0-10% isovanilloyl catalpol and 2.0-15% 6-O-veratroyl catalpol and the pharmaceutically acceptable carriers or excipients, for the treatment or prevention of chronic obstructive pulmonary disease (COPD).

Accordingly, in accordance with the other aspect of the present invention, present invention provide a pharmaceutical composition or a health functional food comprising the novel purified extract containing active ingredients prepared by the above-described methods or at least one compounds selected from the group consisting of veratric acid, verproside, catalposide, picroside II, isovanilloyl catalpol and 6-O-veratroyl catalpol to treat or prevent chronic obstructive pulmonary disease (COPD).

Present invention provide a pharmaceutical composition comprising the novel purified extract containing active ingredients prepared by the above-described methods or at least one compounds selected from the group consisting of veratric acid, verproside, catalposide, picroside II, isovanilloyl catalpol and 6-O-veratroyl catalpol and the pharmaceutically acceptable carriers or excipients, for the treatment or prevention of chronic obstructive pulmonary disease (COPD).

In accordance with another aspect of the present invention, there is also provided a use of the novel purified extract prepared by the above-described methods or at least one compounds selected from the group consisting of veratric acid, verproside, catalposide, picroside II, isovanilloyl catalpol and 6-O-veratroyl catalpol for manufacture of medicines employed for treating or preventing chronic obstructive pulmonary disease (COPD).

The term "pharmaceutically acceptable carriers or excipients" defined herein comprises "pharmaceutical additives, the inactive ingredients used to make up a medication. They include dyes, flavors, binders, emollients, fillers, lubricants, preservatives, and many more classifications. Common excipients include cornstarch, lactose, talc, magnesium stearate, sucrose, gelatin, calcium stearate, silicon dioxide, shellac and glaze, which has been well-known in the art (See, Home-page of Food and Drug Administration: www.fda.gov or drug information online: www.drugs.com) or previous literature (for example, Rowe, Raymond C et al., Handbook of Pharmaceutical Excipients, Pharmaceutical Press, 7th Edition, 2012)

In accordance with another aspect of the present invention, there is also provided a method of treating or preventing chronic obstructive pulmonary disease (COPD) in mammals, wherein the method comprises administering a therapeutically effective amount of the novel purified extract prepared by the above-described methods or at least one compounds selected from the group consisting of veratric acid, verproside, catalposide, picroside II, isovanilloyl catalpol and 6-O-veratroyl catalpol into the mammal suffering from chronic obstructive pulmonary disease (COPD).

In accordance with another aspect of the present invention, there is also provided a method of treating or preventing chronic obstructive pulmonary disease (COPD) in mammals, wherein the method comprises administering a composition comprising therapeutically effective amount of the novel purified extract prepared by the above-described methods or at least one compounds selected from the group consisting of veratric acid, verproside, catalposide, picroside II, isovanilloyl catalpol and 6-O-veratroyl catalpol and the pharmaceutically acceptable carriers or excipients, into the mammal suffering from chronic obstructive pulmonary disease (COPD).

In accordance with another aspect of the present invention, there is also provided a method of treating or preventing chronic obstructive pulmonary disease (COPD) in mammals, wherein the method comprises administering a therapeutically effective amount of the combined compounds with mixed weight ratio of 40-93% verproside, 1.0-10% veratric acid, 2.0-25% catalposide, 1.0-15% picroside II, 1.0-15% isovanilloyl catalpol and 2.0-25% 6-O-veratroyl catalpol, preferably, 45-90% verproside, 1.0-7.0% veratric acid, 3.0-15% catalposide, 2.0-10% picroside II, 2.0-10% isovanilloyl catalpol and 2.0-15% 6-O-veratroyl catalpol, into the mammal suffering from chronic obstructive pulmonary disease (COPD).

In accordance with another aspect of the present invention, there is also provided a method of treating or preventing chronic obstructive pulmonary disease (COPD) in mammals, wherein the method comprises administering a composition comprising a therapeutically effective amount of the combined compounds with mixed weight ratio of 40-93% verproside, 1.0-10% veratric acid, 2.0-25% catalposide, 1.0-15% picroside II, 1.0-15% isovanilloyl catalpol and 2.0-25% 6-O-veratroyl catalpol, preferably, 45-90% verproside, 1.0-7.0% veratric acid, 3.0-15% catalposide, 2.0-10% picroside II, 2.0-10% isovanilloyl catalpol and 2.0-15% 6-O-veratroyl catalpol and the pharmaceutically acceptable carriers or excipients, into the mammal suffering from chronic obstructive pulmonary disease (COPD).

In accordance with another aspect of the present invention, there is also provided a use of a composition comprising novel purified extract prepared by the above-described methods or at least one compounds selected from the group consisting of veratric acid, verproside, catalposide, picroside II, isovanilloyl catalpol and 6-O-veratroyl catalpol and the pharmaceutically acceptable carriers or excipients, for manufacture of medicines employed for treating or preventing chronic obstructive pulmonary disease (COPD).

In accordance with another aspect of the present invention, there is also provided a use of a composition comprising the combined compounds with mixed weight ratio of 40-93% verproside, 1.0-10% veratric acid, 2.0-25% catalposide, 1.0-15% picroside II, 1.0-15% isovanilloyl catalpol and 2.0-25% 6-O-veratroyl catalpol, preferably, 45-90% verproside, 1.0-7.0% veratric acid, 3.0-15% catalposide, 2.0-10% picroside II, 2.0-10% isovanilloyl catalpol and 2.0-15% 6-O-veratroyl catalpol and the pharmaceutically acceptable carriers or excipients, for manufacture of medicines employed for treating or preventing chronic obstructive pulmonary disease (COPD).

The inventive composition for treating and preventing chronic obstructive pulmonary disease (COPD) may comprises above extracts or compounds as 0.1~99%, preferably, 0.1~50% by weight based on the total weight of the composition.

The composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, *acacia* rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

For example, the compositions of the present invention can be dissolved in oils, propylene glycol or other solvents that are commonly used to produce an injection. Suitable examples of the carriers include physiological saline, polyethylene glycol, ethanol, vegetable oils, isopropyl myristate, etc., but are not limited to them. For topical administration, the extract of the present invention can be formulated in the form of ointments and creams.

Pharmaceutical formulations containing present composition may be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), or injectable preparation (solution, suspension, emulsion).

The composition of the present invention in pharmaceutical dosage forms may be used in the form of their pharmaceutically acceptable salts, and also may be used alone or in appropriate association, as well as in combination with other pharmaceutically active compounds.

The desirable dose of the inventive extract or compound varies depending on the condition and the weight of the subject, severity, drug form, route and period of administration, and may be chosen by those skilled in the art. However, in order to obtain desirable effects, it is generally recommended to administer at the amount ranging from 0.0001 to 1000 mg/kg, preferably, 0.001 to 100 mg/kg by weight/day of the inventive extract of the present invention. The dose may be administered in single or divided into several times per day.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intracutaneous, intrathecal, epidural or intracerebroventricular injection.

The inventive extract of the present invention also can be used as a main component or additive and aiding agent in the preparation of various functional health food and health care food.

Accordingly, it is the other object of the present invention to provide a health functional food comprising a therapeutically effective amount of the novel purified extract containing active ingredients prepared by the above-described methods or at least one compounds selected from the group consisting of veratric acid, verproside, catalposide, picroside II, isovanilloyl catalpol and 6-O-veratroyl catalpol for the prevention or alleviation of chronic obstructive pulmonary disease (COPD).

Accordingly, it is the other object of the present invention to provide a health functional food comprising the combined compounds with mixed weight ratio of 40-93% verproside, 1.0-10% veratric acid, 2.0-25% catalposide, 1.0-15% picroside II, 1.0-15% isovanilloyl catalpol and 2.0-25% 6-O-veratroyl catalpol, preferably, 45-90% verproside, 1.0-7.0% veratric acid, 3.0-15% catalposide, 2.0-10% picroside II, 2.0-10% isovanilloyl catalpol and 2.0-15% 6-O-veratroyl catalpol for the prevention or alleviation of chronic obstructive pulmonary disease (COPD).

The term "a functional health food" defined herein" the functional food having enhanced functionality such as physical functionality or physiological functionality by adding the extract of the present invention to conventional food to prevent or improve the purposed diseases in human or mammal.

It is the other object of the present invention to provide a health care food comprising a therapeutically effective amount of the novel purified extract containing abundant active ingredients prepared by the above-described methods or at least one compounds selected from the group consisting of veratric acid, verproside, catalposide, picroside II, isovanilloyl catalpol and 6-O-veratroyl catalpol together with a sitologically acceptable additive for the prevention or alleviation of chronic obstructive pulmonary disease (COPD).

The term "a health care food" defined herein "the food containing the extract or compound(s) of the present invention showing no specific intended effect but general intended effect in a small amount of quantity as a form of additive or in a whole amount of quantity as a form of powder, granule, capsule, pill, tablet etc.

The term "a sitologically acceptable additive" defined herein comprises "any substance the intended use which results or may reasonably be expected to result-directly or indirectly-in its becoming a component or otherwise affecting the characteristics of any food", and can be classified into three groups according to its origin, i.e., (1) chemically synthetic additive such as ketones, glycin, potassium citrate, nicotinic acid, etc; (2) natural additive such as persimmon dye, licorice extract, crystalline cellulose, gua dum etc; (3) the mixed additive therewith such as sodium L-glutamate, preservatives, tar dye etc, or various categories according to its function in the food, for example, thickening agent, maturing agent, bleaching agent, sequestrant, humectant, anti-caking agent, clarifying agents, curing agent, emulsifier, stabilizer, thickener, bases and acid, foaming agents, nutrients, coloring agent, flavoring agent, sweetner, preservative agent, anti-oxidant, etc, which has been well-known in the art or previous literature (See, "Codex General Standard for Food Additives" (GSFA, Codex STAN 192-1995) in Homepage of GSFA Online: www.codexalimentarius.net/gsfaonline/index.html).

If a substance is added to a food for a specific purpose in that food, it is referred to as a direct additive and indirect food additives are those that become part of the food in trace amounts due to its packaging, storage or other handling.

The term "health care foods or health functional foods" disclosed herein can be contained in food, health beverage, dietary supplement etc, and may be formulated into a form of pharmaceutically dosing form such as a powder, granule, tablet, suspension, emulsion, syrup, chewing tablet, capsule, beverage etc; or the food form, for example, bread, rice cake, dry fruit, candy, chocolate, chewing gum, ice cream, milk such as low-fat milk, lactose-hydrolyzed milk, goat-milk, processed milk, milk product such as fermented milk, butter, concentrated milk, milk cream, butter oil, natural cheese, processed cheese, dry milk, milk serum etc, processed meat product such as hamburger, ham, sausage, bacon etc, processed egg product, fish meat product such as fish cake etc, noodle products such as instant noodles, dried noodles, wet noodles, fried noodles, non-fried noodles, gelatinized dry noodles, cooked noodles, frozen noodles, Pasta etc, tea product such as tea bag, leached tea etc, health drinks such as fruit drinks, vegetable drinks, carbonated soft drinks, soymilk drinks, lactic beverage mixed beverage, etc, seasoning food such as soy sauce, soybean paste, red pepper paste, chunjang (a kind of fermented soybean product colored by caramel), cheonggukjang (natural fermented soybean by *B. subtillis*), mixed paste, vinegar, sauce, ketchup, curry, dressing etc, margarine, shortening, pizza etc, but not intended herein to limit thereto, for preventing or improving of purposed disease.

Also, above described extract can be added to food or beverage for prevention and improvement of purposed disorder. The amount of above described extract or a compound(s) in food or beverage as a functional health food or health care food may generally range from about 0.01 to 100 w/w % of total weight of food for functional health food composition. In particular, although the preferable amount of the extract of the present invention in the functional health food, health care food or special nutrient food may be varied in accordance to the intended purpose of each food, it is preferably used in general to use as an additive in the amount of the extract or a compound(s) of the present invention ranging from about 0.01 to 5% in food such as noodles and the like, from 40 to 100% in health care food on the ratio of 100% of the food composition.

Providing that the health beverage composition of present invention contains above described extract or a compound(s) as an essential component in the indicated ratio, there is no particular limitation on the other liquid component, wherein the other component can be various deodorant or natural carbohydrate etc such as conventional beverage. Examples of aforementioned natural carbohydrate are monosaccharide such as glucose, fructose etc; disaccharide such as maltose, sucrose etc; conventional sugar such as dextrin, cyclodextrin; and sugar alcohol such as xylitol, and erythritol etc. As the other deodorant than aforementioned ones, natural deodorant such as taumatin, stevia extract such as levaudiosideA, glycyrrhizin et al., and synthetic deodorant such as saccharin, aspartam et al., may be useful favorably. The amount of above described natural carbohydrate is generally ranges from about 1 to 20 g, preferably 5 to 12 g in the ratio of 100 ml of present beverage composition.

The other components than aforementioned composition are various nutrients, a vitamin, a mineral or an electrolyte, synthetic flavoring agent, a coloring agent and improving agent in case of cheese, chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. The other component than aforementioned ones may be fruit juice for preparing natural fruit juice, fruit juice beverage and vegetable beverage, wherein the component can be used independently or in combination. The ratio of the components is not so important but is generally range from about 0 to 20 w/w % per 100 w/w % present composition. Examples of addable food comprising aforementioned extract or compound therein are various food, beverage, gum, vitamin complex, health improving food and the like.

Inventive extract or a compound(s) of the present invention has no toxicity and adverse effect therefore; they can be used with safe.

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

Advantageous Effects

As described in the present invention, inventive purified extract containing abundant active ingredients such as catalpol derivatives from the extract of *Pseudolysimachion rotundum* var *subintegrum* or at least one compounds selected from the group consisting of veratric acid, verproside, catalposide, picroside II, isovanilloyl catalpol and 6-O-veratroyl catalpol showed potent anti-COPD activity without beta-2-receptor agonistic response through various in vivo tests using by BALB/c male mice, for example, an inhibition test on the proliferation and activity of inflammatory immunocytes and neutrophils recruiting to lung caused by COPD occurrence; an inhibition test on the reproduction of chemokines involved in the destruction of pneumocyte, such as MIP-2/CXCL-2, TNF-alpha, KC/CXCL-1 (Chemokines Gro-alpha) and CXCL-8 etc; the reducing effect on the release of IL-1 beta, IL-6, TNF-alpha and MMP-9 expression by decreasing NF-kappaB activation in animal test using by SPF (specific pathogen-free) Sprague-Dawley rat, as well as in vitro test, for example, an inhibition test on the expression of MUC5AC (oligomeric muscus/gel-forming), inducing effect on the IL-4-expression of Th2 cell in molecular expression profiling change test etc. Therefore, it can be used as the therapeutics or functional health food for treating and preventing chronic obstructive pulmonary disease (COPD).

DESCRIPTION OF DRAWINGS

Best Mode

The above and other objects, features and other advantages of the present invention will more clearly understood from the following detailed description taken in conjunction with the accompanying drawings, in which.

BEST MODE FOR CARRYING OUT THE INVENTION

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

EXAMPLES

The following Reference Example, Examples and Experimental Examples are intended to further illustrate the present invention without limiting its scope.

Comparative Example 1

Preparation of the Crude Extract of *Pseudolysimachion rotundum* Var *Subintegrum*

1-1. Preparation of Crude Extract (ATE)

1 kg of dried *Pseudolysimachion rotundum* var *subintegrum* (cultivated at 244, Soi-myeon Eumseong-gun Chungcheongbuk-do in Korea according to GAP) cut into small pieces and mixed with 10 L of 40% ethanol. The mixture was stirred at room temperature for 24 hours and extracted with reflux extraction at 78° C. for 12 hours to collect the filtrate, three times. The extract was filtered with filter paper to remove the debris. The collected filtrate was concentrated by rotary evaporator (EYELA, N-2100, Japan) at 55~65° C. under reduced pressure and dried with freezing dryer to obtain 202 g of dried crude extract (designated as 'ACE" hereinafter) for used as a comparative example.

1-2. Component Analysis

Figure 1:
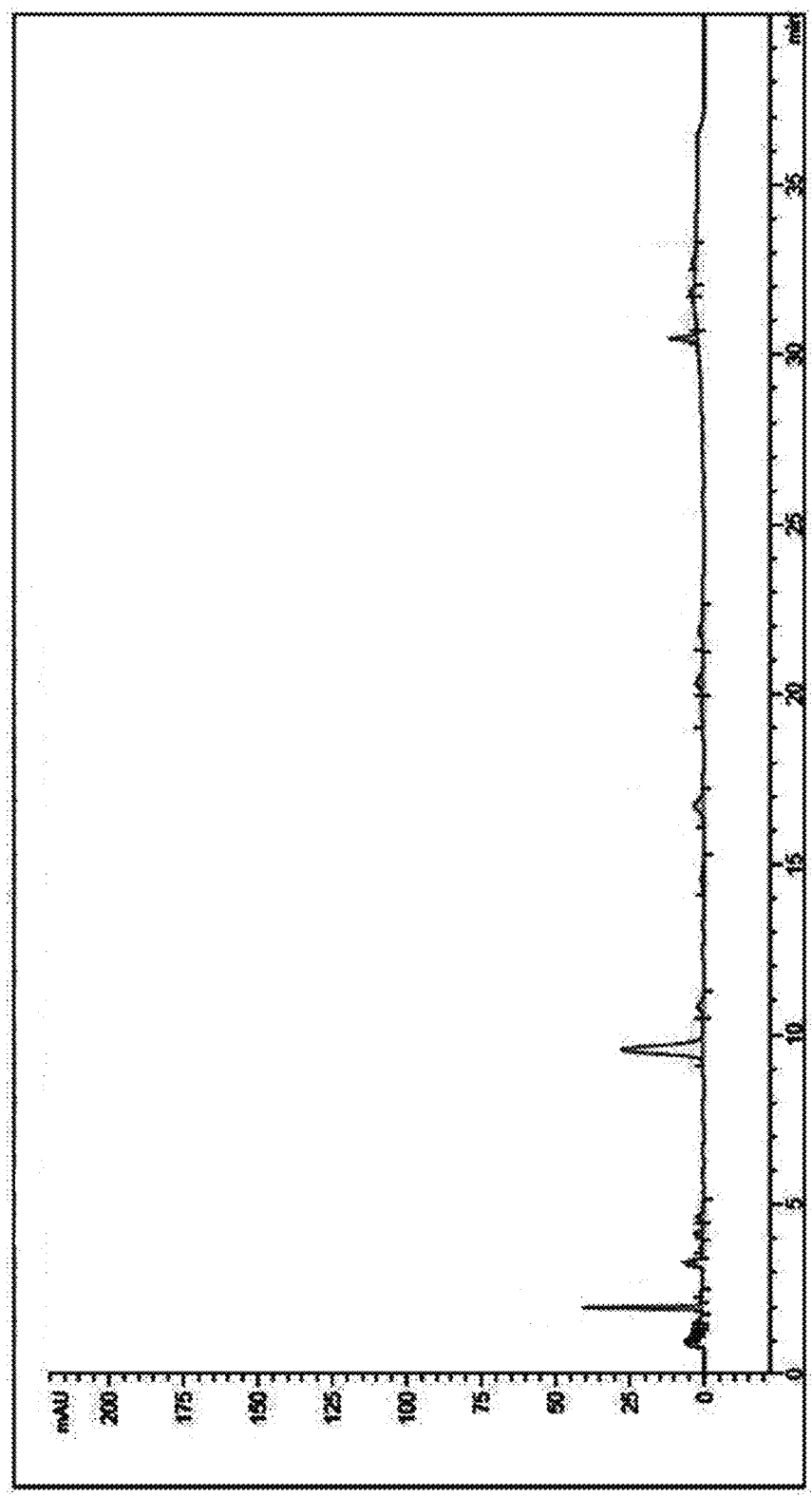
FIG. 1 shows HPLC analysis of the crude extract of *Pseudolysimachion rotundum* var *subintegrum* prepared in comparative Example 1.

The component analysis was performed using by HPLC (Agilent 1260 model, USA) according to the condition in Table 1 and the result was shown in FIG. 1.

As can be seem in FIG. 1, it has been confirmed that each ingredient was detected at 9.548 mins (Verproside), 10.817 mins (Veratric acid), 16.728 mins (Catalposide), 20.346 min (Picroside II), 21.853 mins (Isovanilloyl catalpol), and 30.462 mins (6-O-veratroyl catalpol) respectively.

The content of each ingredient (%) in the sample was calculated based on the HPLC pattern (retention time) according to math formulae 1.

$$\text{content of each ingredient} = \text{conc. of standard (mg/ml)/conc. of test sample (mg/ml)} \times At/As \times \text{purity of standard (\%)} \quad [\text{Math formulae 1}]$$

wherein "At" denotes the ingredient area in test sample and "As" denotes that in standard provided that the sampled volume of test sample and standard is identical to each other.

TABLE 1

| HPLC condition | |
|---|---|
| HPLC condition | |
| Pump | Agilent 1260 Series, 1260 quart pump |
| Detector | Agilent 1260 Series, 1260 DAD |
| Column | Agilent Eclipse XOB C18, 4.6 × 50 cm, 5 μm |
| Flow rate | 1.5 ml/min |
| UV Absorbance | 266 nm |

| Mobile phase Mobile phase A: phosphate buffer (pH = 3.5) Mobile phase B: methanol | | |
|---|---|---|
| Time | Mobile phase A (%) | Mobile phase B (%) |
| 0~5 | 80 | 20 |
| 5~20 | 75 | 25 |
| 20~25 | 75 | 25 |
| 25~30 | 55 | 45 |
| 30~35 | 55 | 45 |
| 35~36 | 80 | 20 |
| 36~40 | 80 | 20 |

| Injection volume | 10 μl | |

At the result, it has been confirmed that the crude extract of *Pseudolysimachion rotundum* var *subintegrum* contains only 8.49% (w/w) catalposide derivatives, i.e., 5.9% (w/w) verproside, 0.21% (w/w) veratric acid, 0.82% (w/w) catalposide, 0.40% (w/w) picroside II, 0.42% (w/w) isovanillyl catalpol, and 0.74% (w/w) 6-O-veratroyl catalpol, respectively, as can be seen in Table 2.

TABLE 2

| HPLC result (crude extract: ACE) | | |
|---|---|---|
| | Comparative Example 1 | |
| Active ingredient | Retention Time (mins) | Content (w/w %) |
| Verproside | 9.548 | 5.90 |
| Veratric acid | 10.817 | 0.21 |
| Catalposide | 16.728 | 0.82 |
| Picroside II | 20.346 | 0.40 |
| Isovanilloyl catalpol | 21.853 | 0.42 |
| 6-O-veratroyl catalpol | 30.462 | 0.74 |
| Total | | 8.49 |

Example 1

Preparation of the Purified Extract (ATC1) of *Pseudolysimachion rotundum* Var *Subintegrum*

The crude extract (ACE) of *Pseudolysimachion rotundum* var *subintegrum* prepared by the conventional method according to Comparative Example 1, was suspended in 2 L of distilled water and the suspension was added with 2 L of butanol to fractionate into butanol-soluble fraction and water-soluble fraction. The butanol soluble fraction was collected, concentrated under reduced pressure and dried to afford 82 g of the inventive purified extract fractionated with butanol (ATC1) used as a test example.

Figure 2:
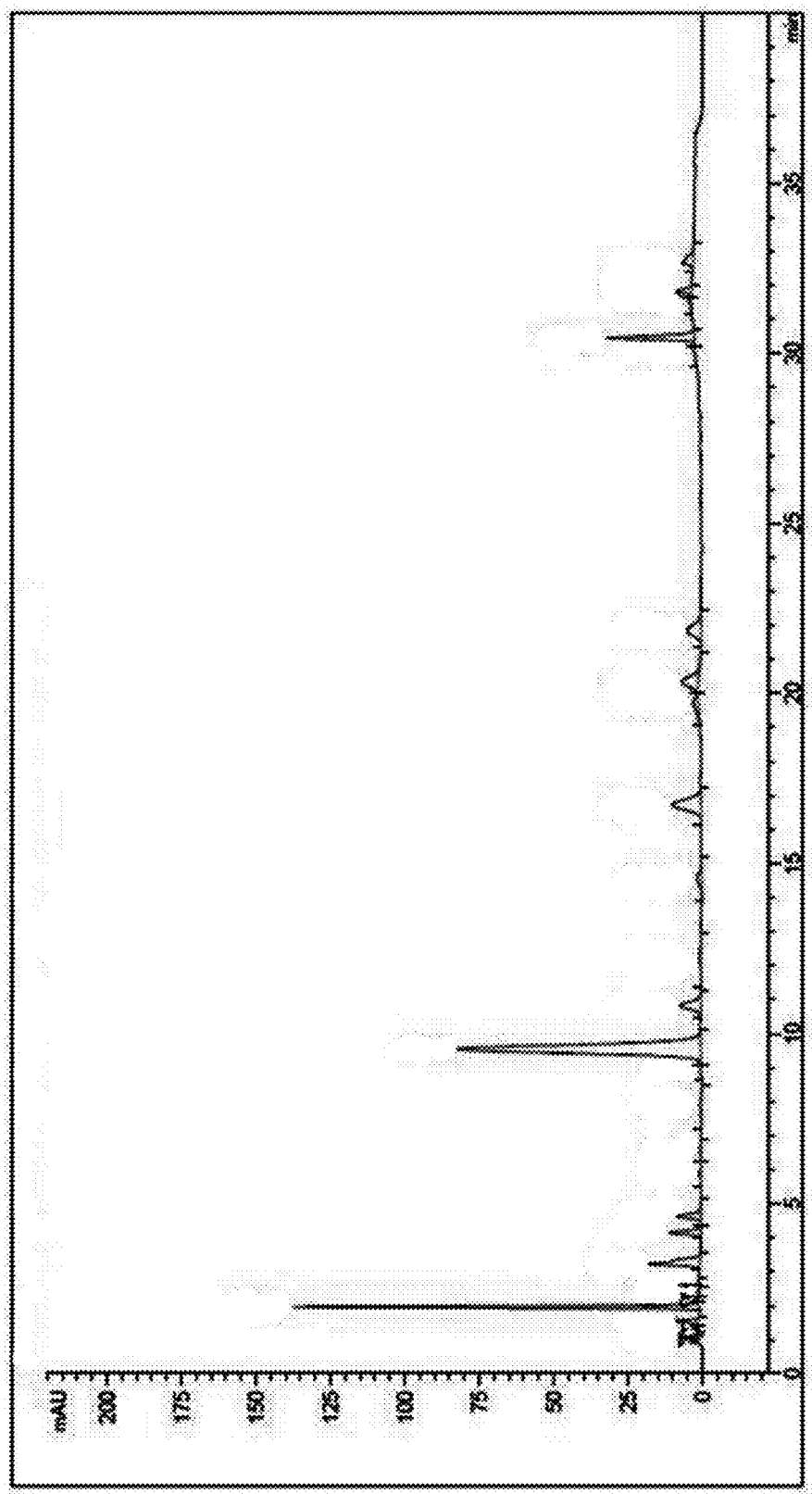
FIG. 2 shows HPLC analysis of the inventive purified extract (ATC1) of *Pseudolysimachion rotundum* var *subintegrum* prepared in Example 1.

The component analysis was performed using by HPLC (Agilent 1260 model, USA) according to the condition in Table 1 and the result was shown in FIG. 2.

As can be seem in FIG. 2, it has been confirmed that each ingredient was detected at 9.545 mins (Verproside), 10.821 mins (Veratric acid), 16.727 mins (Catalposide), 20.345 min (Picroside II), 21.853 mins (Isovanilloyl catalpol), and 30.462 mins (6-O-veratroyl catalpol) respectively.

The content of each ingredient (%) in the sample was calculated based on the HPLC pattern (retention time) according to math formulae 1.

At the result, it has been confirmed that the inventive purified extract fractionated with butanol (ATC1) of *Pseudolysimachion rotundum* var *subintegrum* contains 25.64% (w/w) catalposide derivatives, i.e., 17.60% (w/w) verproside, 0.72% (w/w) veratric acid, 2.62% (w/w) catalposide, 1.08% (w/w) picroside II, 1.26% (w/w) isovanillyl catalpol, and 2.36% (w/w) 6-O-veratroyl catalpol, respectively, as can be seen in Table 3.

TABLE 3

HPLC result (purified extract: ATC1)

Example 1

| Active ingredient | Retention Time (mins) | Content (w/w %) |
|---|---|---|
| Verproside | 9.545 | 17.60 |
| Veratric acid | 10.821 | 0.72 |
| Catalposide | 16.727 | 2.62 |
| Picroside II | 20.345 | 1.08 |
| Isovanilloyl catalpol | 21.853 | 1.26 |
| 6-O-veratroyl catalpol | 30.462 | 2.36 |
| Total | | 25.64 |

Example 2

Preparation of the Purified Extract (ATC2) of *Pseudolysimachion rotundum* var *subintegrum*

The inventive purified extract fractionated with butanol (ATC1) of *Pseudolysimachion rotundum* var *subintegrum* according to Example 1, was dissolved in 75 ml of mixed solvent (distilled water:methaol=1:0.003) and 75 g of the solution was loaded on reverse phase column chromatography (C18 (IV)-D-75-120 nm, AGC Si-Tech Co. Ltd., Japan, 450 g) with eluting the suspension using by eluting solvent (distilled water:methanol=90:10→60:40). 8.4 L of the eluted solution running at the initial eluting solvent system (distilled water:methanol=90:10) was collected and concentrated under reduced pressure. 5.6 L of the eluted solution running at the late eluting solvent system (distilled water:methanol=60:40) was collected, concentrated under reduced pressure and dried to afford 33 g of the inventive purified extract with the secondary fractionation (ATC2) used as a test example.

Figure 3:
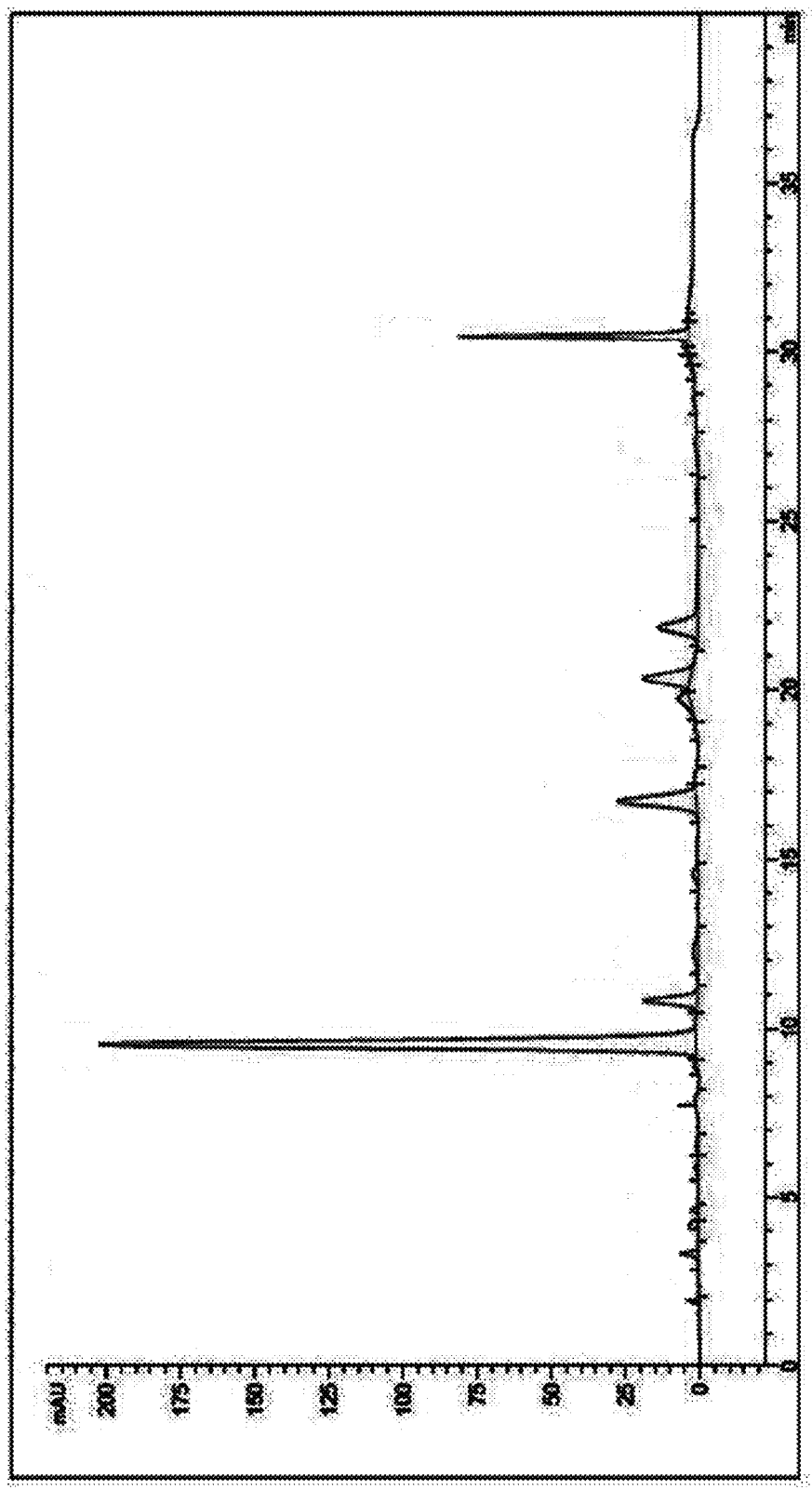
FIG. 3 shows HPLC analysis of the inventive purified extract (ATC2) of *Pseudolysimachion rotundum* var *subintegrum* prepared in Example 2.

The component analysis was performed using by HPLC (Agilent 1260 model, USA) according to the condition in Table 1 and the result was shown in FIG. 3.

As can be seem in FIG. 3, it has been confirmed that each ingredient was detected at 9.525 mins (Verproside), 10.818 mins (Veratric acid), 16.721 mins (Catalposide), 20.346 min (Picroside II), 21.857 mins (Isovanilloyl catalpol), and 30.462 mins (6-O-veratroyl catalpol) respectively.

The content of each ingredient (%) in the sample was calculated based on the HPLC pattern (retention time) according to math formulae 1.

At the result, it has been confirmed that the inventive purified extract with the secondary fractionation (ATC2) of *Pseudolysimachion rotundum* var *subintegrum* contains 65.63% (w/w) catalpol derivatives, i.e., 43.83% (w/w) verproside, 1.80% (w/w) veratric acid, 7.07% (w/w) catalposide, 2.93% (w/w) picroside II, 3.85% (w/w) isovanillyl catalpol, and 6.15% (w/w) 6-O-veratroyl catalpol, respectively, as can be seen in Table 4.

TABLE 4

HPLC result (purified extract: ATC2)

Example 2

| Active ingredient | Retention Time (mins) | Content (w/w %) |
|---|---|---|
| Verproside | 9.524 | 43.83 |
| Veratric acid | 10.818 | 1.80 |
| Catalposide | 16.721 | 7.07 |
| Picroside II | 20.346 | 2.93 |
| Isovanilloyl catalpol | 21.857 | 3.85 |
| 6-O-veratroyl catalpol | 30.462 | 6.15 |
| Total | | 65.63 |

Example 3

Preparation of Inventive Compounds from *Pseudolysimachion rotundum* Var *Subintegrum*

The inventive compounds, i.e., verproside, veratric acid, catalposide, picroside II, isovanilloyl catalpol, and 6-O-veratroyl catalpol having following physico-chemical properties, were purified from the extract of *Pseudolysimachion rotundum* var *subintegrum* according to isolating method disclosed in Korean Patent Publication No. 10-2006-125499, and the physico-chemical properties of each compound were compared with those in the already published literatures for the identification of each chemical structure.

1. Verproside
(=6-O-(3,4-dihydroxybenzoyl)catalpol)

$^1$H NMR (400 MHz, DMSO-$d_6$) δ: 2.47 (1H, dd, J=8.0, 9.2 Hz, H-9), 2.59 (1H, dddd, J=1.6, 4.0, 8.0, 8.0, H-5), 3.00 (1H, m, H-G4), 3.05 (1H, m, H-G2), 3.14 (1H, m, H-G5), 3.18 (1H, m, H-G3), 3.42, 3.71 (2H, m, H-G6). 3.67 (1H, s, H-7), 3.71, 3.91 (2H, d, J=13.2 Hz, each, H-10), 4.61 (1H, d, J=7.6 Hz, H-G1), 4.94 (1H, dd, J=4.0, 6.0 Hz, H-4), 5.03 (1H, d, J=8.0 Hz, H-6), 5.09 (1H, d, J=9.2 Hz, H-1), 6.41 (1H, dd, J=1.6. 6.0 Hz, H-3), 6.82 (1H, d, J=8.0 Hz, H-5'), 7.35 (1H, dd, J=2.0, 8.0 Hz, H-6'), 7.39 (1H, d, J=2.0 Hz, H-2').

$^{13}$C-NMR (100 MHz, DMSO-$d_6$) δ: 93.0 (C-1), 141.1 (C-3), 101.8 (C-4), 35.2 (C-5), 79.5 (C-6), 58.2 (C-7), 65.8 (C-8), 41.8 (C-9), 120.0 (C-1'), 116.4 (C-2'), 145.1 (C-3'), 150.8 (C-4'), 115.4 (C-5'), 122.6 (C-6'), 165.6 (C-7'), 97.9 (C-G1), 73.4 (C-G2), 76.4 (C-G3), 70.3 (C-G4), 77.5 (C-G5), 61.4 (C-G6).

2. Picroside II (=6-O-(4-hydroxy-3-methoxybenzoly)catalpol)

$^1$H-NMR (400 MHz, DMSO-d$_6$) δ: 2.47 (1H, dd, J=8.0, 9.6 Hz, H-9), 2.58 (1H, dddd, J=1.2, 6.0, 8.0, 8.4 Hz, H-5), 3.00 (1H, m, H-G4), 3.05 (1H, m, H-G2), 3.14 (1H, m, H-G5), 3.18 (1H, m, H-G3), 3.42, 3.71 (2H, m, H-G6), 3.67 (1H, br s, H-7), 3.72, 3.92 (2H, d, J=13.2, each, H-10), 4.62 (1H, d, J=7.6 Hz, H-G1), 4.99 (1H, dd, J=4.4, 6.0 Hz, H-4), 5.06 (1H, d, J=8.4 Hz, H-6), 5.11 (1H, d, J=9.6 Hz, H-1), 6.42 (1H, dd, J=1.2. 6.0 Hz, H-3), 6.89 (1H, d, J=8.4 Hz, H-5'), 7.46 (1H, d, J=2.0 Hz, H-2$^1$), 7.52 (1H, dd, J=2.0, 8.4 Hz, H-6'), 3.83 (3H, s, 3'-O—CH3).

$^{13}$C-NMR (100 MHz, DMSO-d$_6$) δ: 93.0 (C-1), 141.1 (C-3), 101.8 (C-4), 35.2 (C-5), 79.7 (C-6), 58.2 (C-7), 65.8 (C-8), 41.8 (C-9), 58.5 (C-10), 120.0 (C-1'), 112.7 (C-2'), 147.5 (C-3'), 152.0 (C-4'), 115.3 (C-5'), 123.8 (C-6'), 165.6 (C-7'), 97.9 (C-G1), 73.4 (C-G2), 76.4 (C-G3), 70.3 (C-G4), 77.5 (C-G5), 61.4 (C-G6), 55.7 (3'-OCH3).

3. Catalposide (=6-O-(4-hydroxybenzolyl)catalpol)

$_1$H-NMR (400 MHz, DMSO-d$_6$) δ: 2.47 (1H, dd, J=8.0, 9.6 Hz, H-9), 2.56 (1H, dddd, J=1.2, 4.0, 8.0, 8.0 Hz, H-5), 3.00 (1H, m, H-G4), 3.05 (1H, m, H-G2), 3.14 (1H, m, H-G5), 3.18 (1H, m, H-G3), 3.43, 3.72 (2H, m, H-G6), 3.69 (1H, br s, H-7), 3.72, 3.92 (2H, d, J=13.2 Hz, each, H-10), 4.62 (1H, d, J=8.0 Hz, H-G1), 4.96 (1H, dd, J=4.0, 6.0 Hz, H-4), 5.05 (1H, dd, J=1, 2, 8.0 Hz, H-6), 5.11 (1H, d, J=9.6 Hz, H-1), 6.42 (1H, dd, J=1.2. 6.0 Hz, H-3), 6.86 (2H, d, J=8.0 Hz, H-3', -5'), 7.85 (2H, d, J=2.0 Hz, H-2', -6').

$^{13}$C-NMR (100 MHz, DMSO-d$_6$) δ: 92.9 (C-1), 141.1 (C-3), 101.8 (C-4), 35.1 (C-5), 79.6 (C-6), 58.2 (C-7), 65.8 (C-8), 41.8 (C-9), 119.6 (C-1'), 131.7 (C-2', 6'), 115.5 (C-3', 5'), 162.6 (C-4'), 165.5 (C-7'), 97.8 (C-G1), 73.4 (C-G2), 76.4 (C-G3), 70.3 (C-G4), 77.5 (C-G5), 61.4 (C-G6).

4. Isovanilloyl catalpol (=6-O-(3-hydroxy-4-methoxybenzoyl)catalpol)

$^1$H-NMR (400 MHz, DMSO-d$_6$) δ: 2.47 (1H, m, H-9), 2.55 (1H, m H-5), 3.00 (1H, m, H-G4), 3.05 (1H, m, H-G2), 3.14 (1H, m, H-G5), 3.18 (1H, m, H-G3), 3.43, 3.70 (2H, m, H-G6), 3.70 (1H, br s, H-7), 3.72, 3.92 (2H, d, J=13.2, each, H-10), 4.62 (1H, d, J=8.0 Hz, H-G1), 4.95 (1H, dd, J=4.4, 6.0 Hz, H-4), 5.06 (1H, d, J=8.0 Hz, H-6), 5.11 (1H, d, J=9.2 Hz, H-1), 6.42 (1H, d, J=6.0 Hz, H-3), 7.04 (1H, d, J=8.4 Hz, H-5'), 7.42 (1H, br s, H-2'), 7.48 (1H, d, J=8.4 Hz, H-6'), 3.84 (3H, s, 4'-O—CH3).

$^{13}$C-NMR (100 MHz, DMSO-d$_6$) δ: 93.0 (C-1), 141.0 (C-3), 101.6 (C-4), 35.2 (C-5), 79.7 (C-6), 58.2 (C-7), 65.8 (C-8), 41.8 (C-9), 58.4 (C-10), 121.7 (C-1'), 115.7 (C-2'), 146.3 (C-3'), 152.1 (C-4'), 111.4 (C-5'), 121.3 (C-6'), 165.3 (C-7'), 97.8 (C-G1), 73.4 (C-G2), 76.4 (C-G3), 70.3 (C-G4), 77.4 (C-G5), 61.4 (C-G6), 55.7 (4'-OCH3).

5. 6-O-veratroyl catalpol (=6-O-(3,4-di methoxybenzoly)catalpol)

$^1$H-NMR (400 MHz, DMSO-d$_6$) δ: 2.47 (1H, dd, J=8.0, 9.6 Hz, H-9), 2.59 (1H, dddd, J=1.6, 4.8, 8.0, 8.0 Hz, H-5), 3.00 (1H, m, H-G4), 3.05 (1H, m, H-G2), 3.14 (1H, m, H-G5), 3.18 (1H, m, H-G3), 3.42, 3.71 (2H, m, H-G6), 3.70 (1H, br s, H-7), 3.72, 3.90 (2H, d, J=13.2 Hz, each, H-10), 4.61 (1H, d, J=7.6 Hz, H-G1), 4.97 (1H, dd, J=4.8, 6.0 Hz, H-4), 5.08 (1H, d, J=8.8 Hz, H-6), 5.10 (1H, d, J=9.6 Hz, H-1), 6.42 (1H, dd, J=1.6. 6.0 Hz, H-3), 7.09 (1H, d, J=8.4 Hz, H-5'), 7.46 (1H, d, J=2.0 Hz, H-2'), 7.64 (1H, dd, J=2.0, 8.4 Hz, H-6'), 3.81, 3.84 (6H, s each, 3', 4'-OCH3).

$^{13}$C-NMR (100 MHz, DMSO-d$_6$) δ: 92.9 (C-1), 141.1 (C-3), 101.8 (C-4), 35.2 (C-5), 79.9 (C-6), 58.2 (C-7), 65.9 (C-8), 41.8 (C-9), 58.4 (C-10), 121.3 (C-1'), 111.8 (C-2'), 148.5 (C-3'), 153.2 (C-4'), 111.2 (C-5'), 123.5 (C-6'), 165.5 (C-7'), 97.8 (C-G1), 73.4 (C-G2), 76.4 (C-G3), 70.3 (C-G4), 77.5 (C-G5), 61.4 (C-G6), 55.6, 55.7 (3', 4'-OCH$_3$).

Experimental Example 1

Establishment of ADBR2 GPCR-Targeting Cell-Based Assay System

In order to develop ADBR2 GPCR-targeting cell-based assay system, following test was performed.

1-1. Development of ADBR2 GPCR Expressing Cell Line

ADBR2 (beta-2 adrenergic receptor) GPCR (G-protein coupled receptor, Sinco Biological Inc., HF10378-M) was cloned to pIRESpuro vector (Clontech, Mountain View, Calif.), transformed into U2OS (ATCC, HTB-96, human osteosarcoma cell line) and treated with growth medium supplemented with DEME (HyClone), 10% FBS (HyClone, SH30071.03) and 1% antibiotic (Gibco, 15140) to select single colony.

Figure 4:
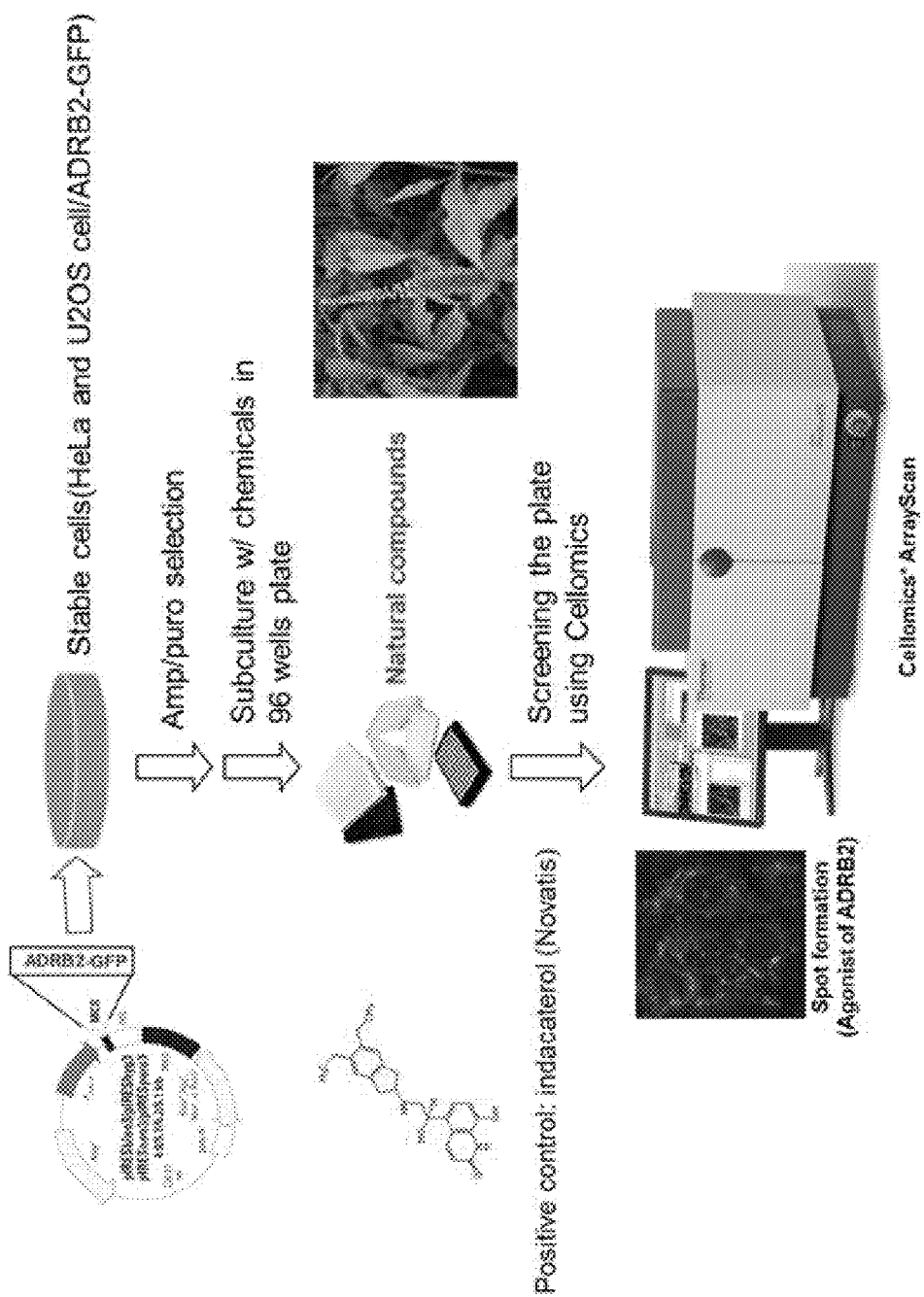
FIG. 4 shows the schematic procedure to establish ADRB2 GPCR-expressing cell line model.

The selected stable colonies were inoculated into 96 well-plates and test samples, i.e., Indacaterol (positive control, Zhiyu biotechnology, China) and 24 hrs after the inoculation, ATC2 extract prepared in Example were treated thereto. The cell was fixed with formalin solution for 5 mins, washed with a sterilized water and confirm the spot formation using by spot detector software (ThermoFisher, U.S.A) as depicted in FIG. 4.

1-2. Evaluation on the Efficacy of Positive Control 10 micromole already well-known ADBR2 agonists, i.e., isopreterenol, salmeterol, formoterol, salbutamol and indacaterol (Zhiyu biotechnology, China) were treated to the selected U2OS cells stably expressing ADBR2 GPCR and the spot formation by the treatment was determined by using spot detector software in Cellomics apparatus (ThermoFisher, U.S.A).

Figure 5:
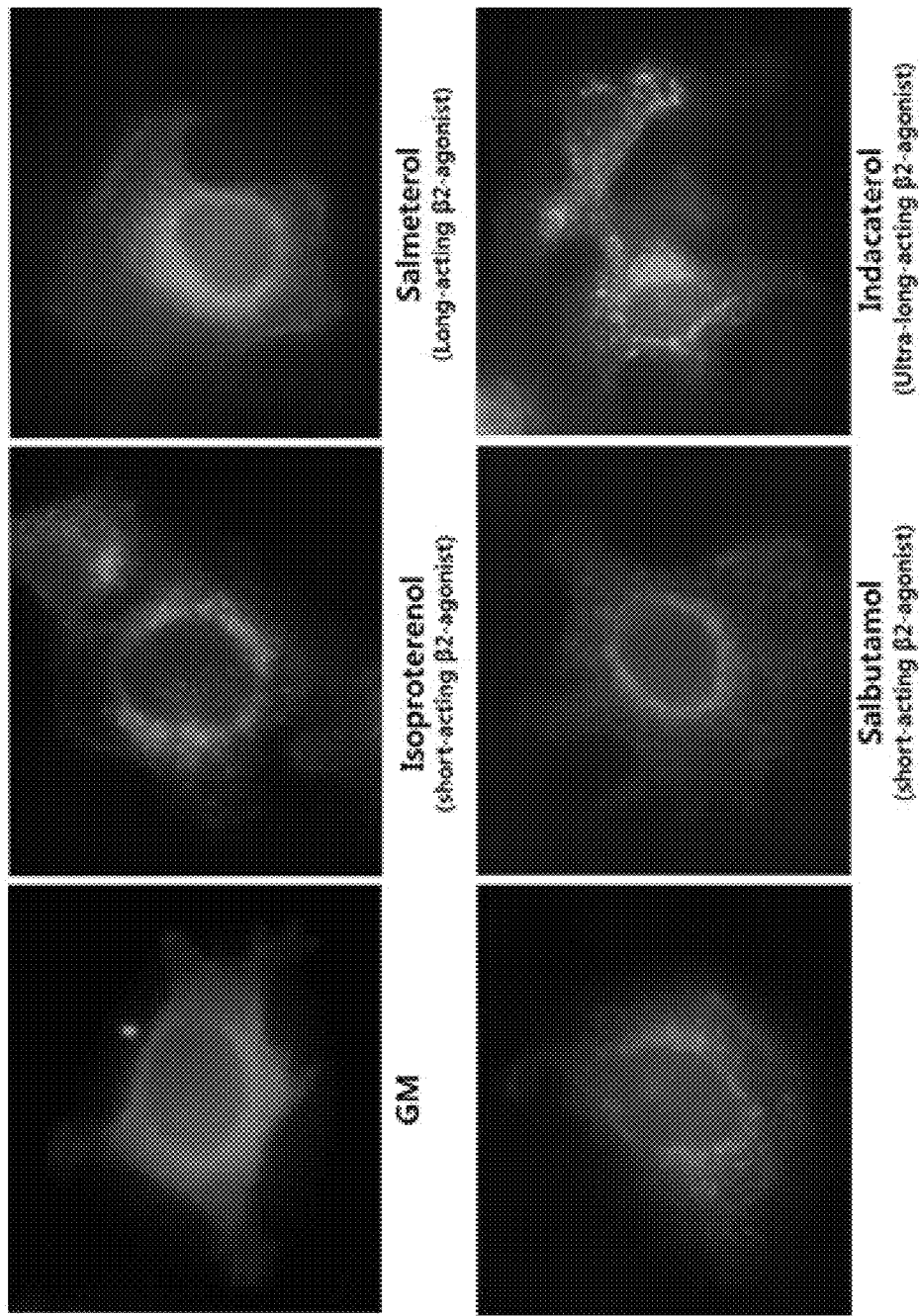
FIG. 5 shows the spot formation in U2OS cell treated with already known ADRB agonist.

As can be seen in FIG. 5, it has confirmed that all the groups treated with already well-known ADBR2 agonists (isopreterenol, salmeterol, formoterol, salbutamol and indacaterol), especially, indacaterol, showed apparent spot formation and the beta 2-agonist such as indacaterol form apparant spot by acting as a ADRB2 agonist (beta 2-receptor) whereas ATC2 at 40 mg/ml did not form spot formation.

1-3. Evaluation on the Efficacy of Test Samples

40 μg/ml of ATC2 as well as the inventive compounds, i.e., 20 micromole verproside, veratric acid, catalposide, picroside II, isovanilloyl catalpol, and 6-O-veratroyl catalpol, respectively, were treated to the selected U2OS cells stably expressing ADBR2 GPCR and the spot formation by the treatment was determined by using spot detector software in Cellomics apparatus (ThermoFisher, U.S.A).

Figure 6:
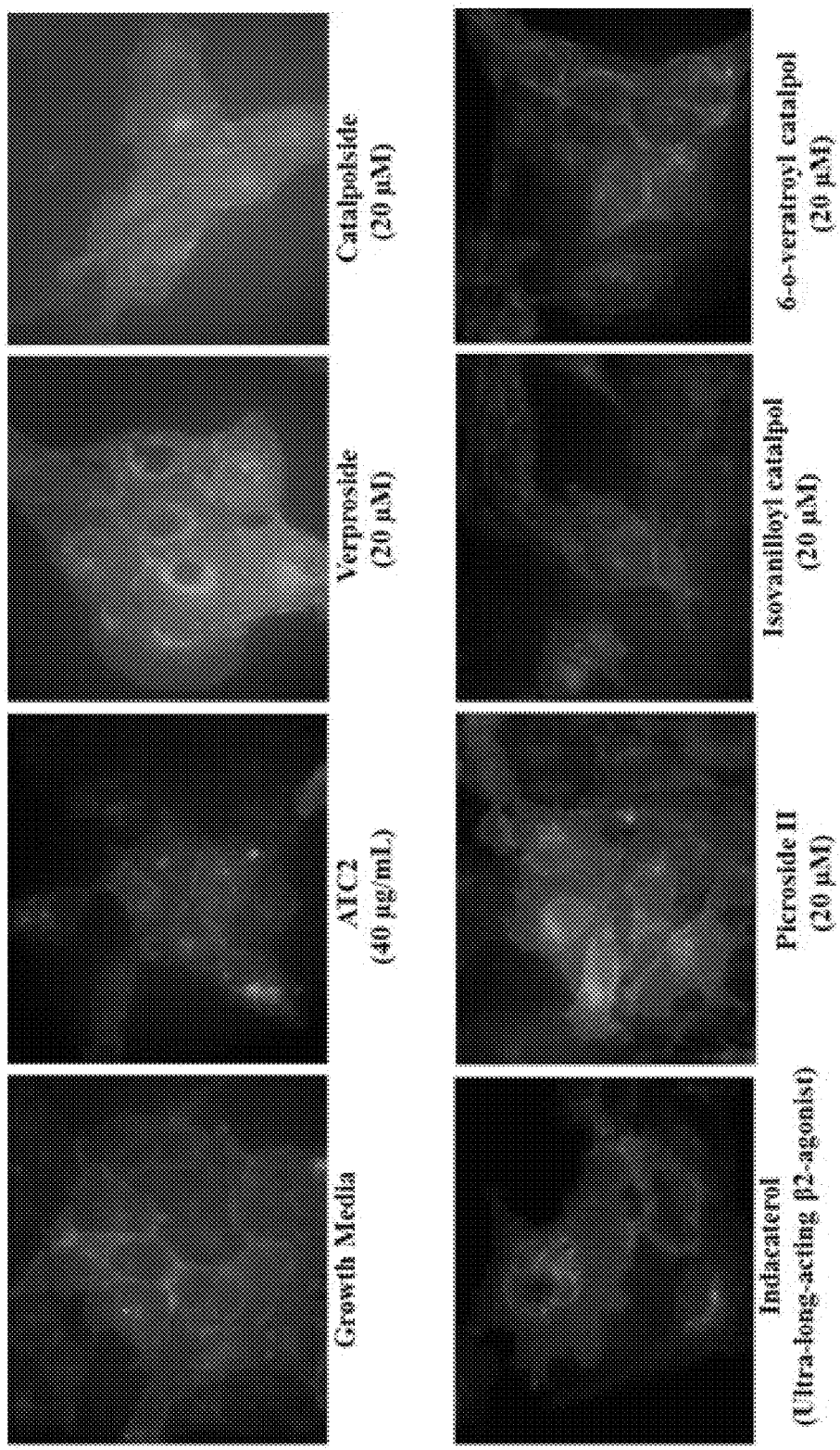
FIG. 6 shows the spot formation in U2OS cell treated with the inventive purified extract and compounds.

As can be seen in FIG. 6, it has confirmed that all the groups treated with ATC2 as well as the inventive compounds, I.e., 20 micromole verproside, veratric acid, catalposide, picroside II, isovanilloyl catalpol, and 6-O-veratroyl catalpol, did not show spot formation, which means the presence of ADRB2-GFP on the receptor. According to the result, it has been confirmed that ATC extract and the inventive compounds did not act as a ADBR2 agonist.

Accordingly, it has also confirmed that inventive extract and inventive compounds directly targeting MUC5AC, a main therapeutic target, and preventing from MUC5AC expression, could solve the existing problems of conventional treatment such as the treatment by beta 2 agonist, for example, adrenergic reaction to beta 2 receptor such as hypokalemia, cramp, anxiety, tachycardia, ventricular premature beats etc and the adverse response in case of oral administration such as arrhythmia, epilepsy etc caused by irregular change in blood drug concentration.

Experimental Example 2

Establishment of Mucin 5AC-Targeting Cell-Based Assay System

There have been reported that Mucin5A/C is an important taget to develop COPD treating agent (Busse P J, Zhang T F, Srivastava K, Schofield B, Li X M. 2007. Effect of ageing on pulmonary inflammation, airway hyperresponsiveness and T and B cell responses in antigen-sensitized and -challenged mice. Clinical & Experimental Allergy. 37(9):1392-403, Smirnova M G, Birchall J P, Pearson J P. 2000. TNF-alpha in the regulation of MUC5AC secretion: some aspects of cytokine-induced mucin hypersecretion on the in vitro model. Cytokine, 12:1732-6).

Accordingly, the present inventors developed novel high throughput screening test by introducing high content screening system which can quantitatively determine the expression of target protein in animal cell level and in order to screening the inhibiting agent of Mucin 5AC expression, following test was performed by modifying the target activator method published on Cellomics BioApplication.

2-1. Digitization of Mucin 5A/C Expression Using by HSC

A549 cell line (ATCC, CCL-185), a epithelial cell line isolated from human lung cancer tissue was seeded on 96 well plates (5,000 cells/well) and 24 hrs after the seeding, 20 ng/ml of bFGF, 100 ng/ml of EGF, 20 micromole IGF, 5 ng/ml of TGF-beta1, 30 nanomole acrolein, 5 nanomole PMA, 1 microgram/ml, LPS and 20 ng/ml of IL-1 beta were treated therewith. The expression of Mucin 5A/C was digitized by target activator program in Cellomics apparatus.

Figure 7:
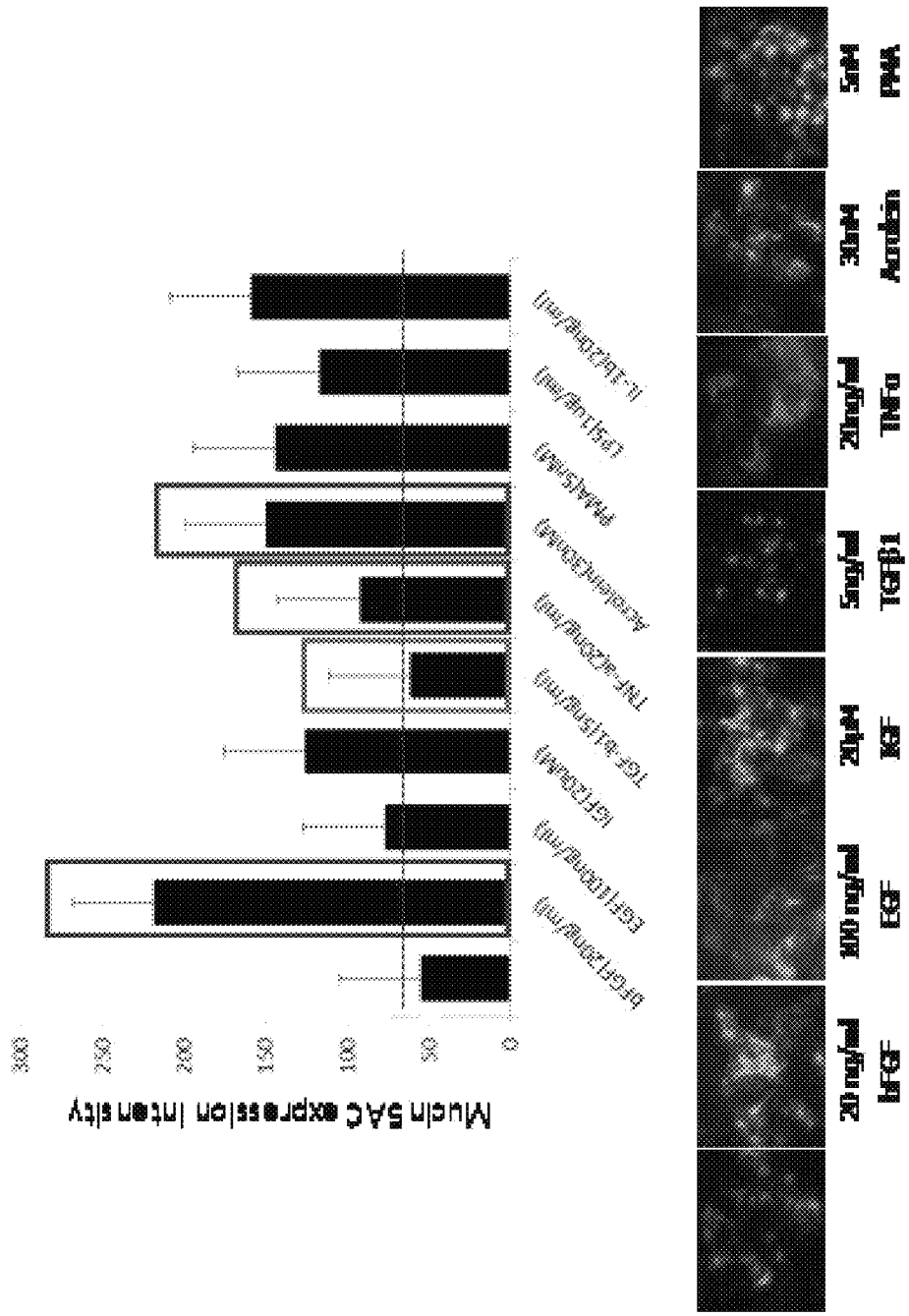
FIG. 7 shows the digitalized result of the expression of MUC5AC using by HSC.

As can be seen in FIG. 7, it has been confirmed that all the tested substances excepting TGF-beta1 increased the expression of MUC5A/C.

2-2. Digitization of Inhibiting Effect of TGF-Beta1 on Mucin 5A/C Expression

Various concentrations of TGF-beta 1 (PeproTech, #100-21), i.e., 1, 5 and 10 ng/ml TGF-beta 1 were treated with A549 cell line (ATCC, CCL-185), and the expression of Mucin 5A/C was digitized by target activator program in Cellomics apparatus.

Figure 8:
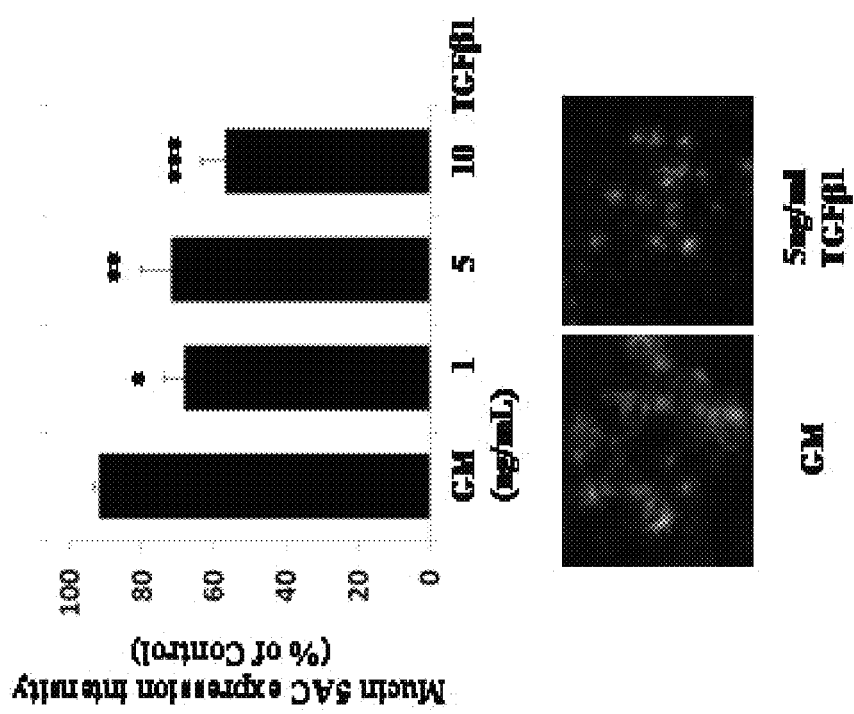
FIG. 8 represents the change of MUC5AC expression in A549 cell treated with TO Fb1.

As can be seen in FIG. 8, it has been confirmed that TGF-beta1 more inhibited the expression of MUC5A/C than control medium (GM, DMEM, 10% FBS, 1% antibiotics).

2-3. Digitization of Inhibiting Effect of TNF-Alpha on Mucin 5A/C Expression

Various concentrations of ATC2 extract were treated with A549 cell line for 2 hours and then 20 g/ml TNF-alpha (Sigma, H8916) was treated therewith for 24 hours. The expression of Mucin 5A/C was digitized by target activator program in Cellomics apparatus.

Figure 9:
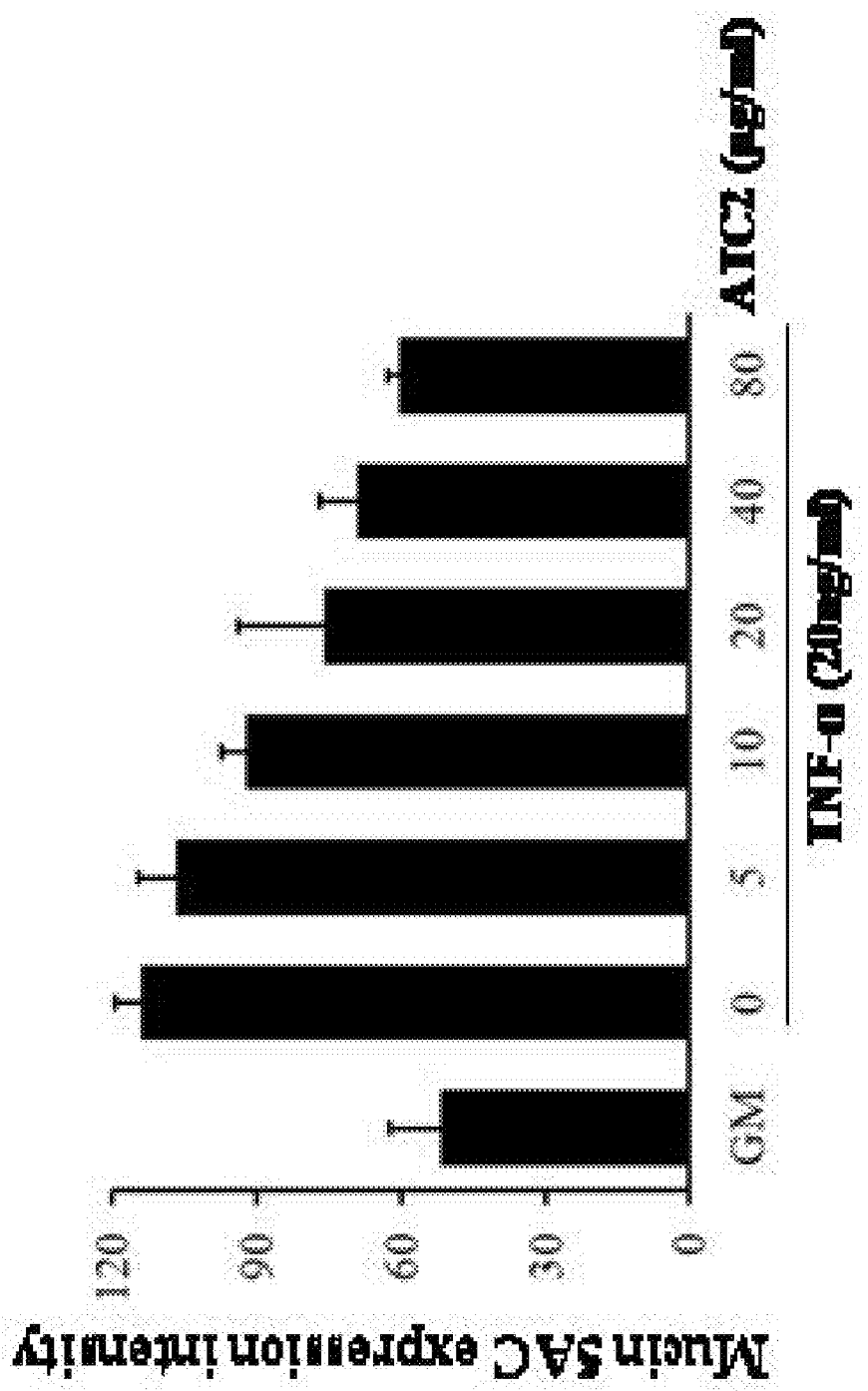
FIG. 9 represents the change of MUC5AC expression in A549 cell which was pre-treated with the inventive purified extract or compounds and then treated with TNF-α.

As can be seen in FIG. 9, it has been confirmed that the expression of MUC5A/C was effectively inhibited with the treatment of TNF-alpha which increases MUC5AC expression in a dose dependent manner in case that ATC2 was pre-treated.

2-4. Inhibiting Effect of Inventive Test Samples on Mucin 5A/C Expression

The diluted A549 cell line (ATCC, CCL-185) with DMEM medium supplemented with 5% phenol red and FBS (Fetal Bovine Serum) was seeded in 6 well plates (4×10$^5$ cells/well) to adhere thereto for a night, and 20 and 40 microgram/ml of ATC2 extract were treated with A549 cell line for 1 hours. 30 nM acrolein was treated therewith to induce Mucin 5A/C expression. The medium was removed the cell, washed with PBS solution and homogenized with Trizol (Invitrogen, CA, USA) for the isolation of ribonucleic acids from the cells for 5 mins. the cells were collected, transferred to centrifugal separator, completely mixed with chloroform for 15 seconds, left alone for 3 mins and centrifuged for 15 mins at the speed of 14,000 rpm. The supernatant containing ribonucleic acid was transferred to new tube and mixed with isopropylalcohol for 10 mins. The solution was centrifuged to discard the supernatant and 75% ethanol was added to the precipitate. The precipitate was centrifuged for 5 mins at the speed of 10,000 rpm and the supernatant was discarded. The precipitated ribonucleic acid was dried at room temperature for 20 mins. The dried ribonucleic acid was suspended in distilled water treated with DEPC (Diethylpyrocarbonate, W2004, www.biosesang.com, Korea). After the quantification of ribonucleic acid, the complementary DNA was synthesized using by 1 microgram of RNA and RT-kit (Omniscript RT kit, Qiagen, USA) and the synthetic cDNA was used as a template. Mucin5A/C primer (Forward; 5-CGA CAA CTA CTT CTG CGG TGC-3, Reverse: 5-GCA CTC ATC CTT CCT GTC GTT-3) was mixed therewith, denatured for 5 mins at 94° C. using by PCR mix (DreamTaq™ PCR Master Mix, Fermentas, USA), reacted for 40 cycles, i.e., 30 seconds at 94° C., 30 seconds at 58° C., 45 seconds at 72° C. and performed to PCR for 5 mins at 72° C. in order to enzyme inactivation. GAPDH (Glyceraldehyde-3-phosphate dehydrogenase, Bioneer Corporation, www.bioneer.co.kr, Korea) was used as an internal standard.

Figure 10:
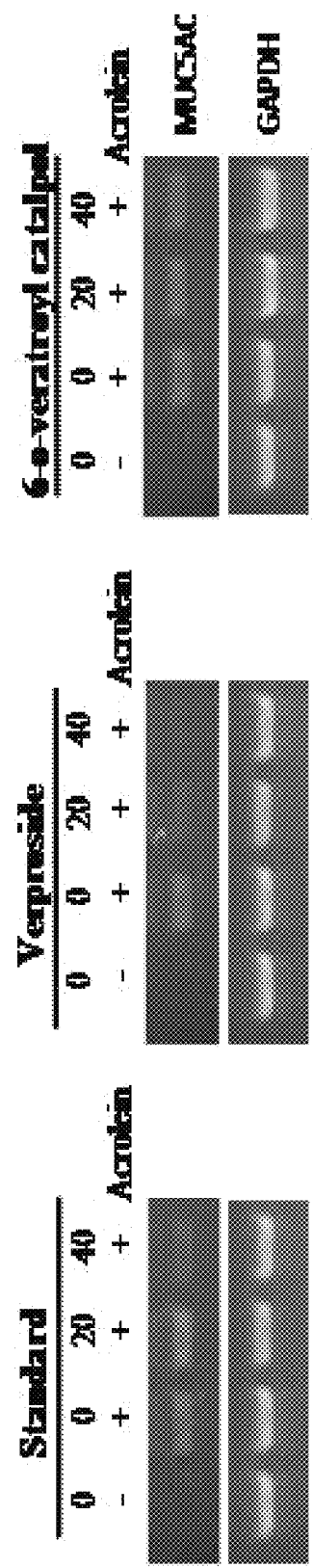
FIG. 10 represents the change of MUC5AC expression in A549 cell treated with acrolein, the inventive purified extract or compounds.

As can be seen in FIG. 10, it has been confirmed that the expression of MUC5A/C was increased by acrolein treatment while it was inhibited with the treatment of inventive extract (ARC2) or inventive compounds such as verproside or 6-O-veratroyl catalpol in a dose dependent manner.

Experimental Example 3

Inhibition Effect on Mouse Th2 Cell Differentiation 3-1. Establishment of Mouse Th2 Cell Differentiation aCD4$^+$ T cells (CD4$^+$CD62L$^+$) was isolated from the lymph nodes and spleens of C57BL6 mice using by MACS (Miltenyi Biotec, Order no. 130-090-976) and the collected CD4$^+$ T cells were cultured on the coated plates with anti-CD3 (1 µg/ml, BD pharmingen) and anti-CD28 (0.5 µg/ml, BD pharmingen).

The differentiation of TH2 cells were induced by RPMI medium supplemented with anti-IFN-gamma and rmIL-4 (Hyclone) and the degree of differentiation was determined by FACS (Flow cytometry, Becton-Dickinson, FACSCalibur).

Figure 11:
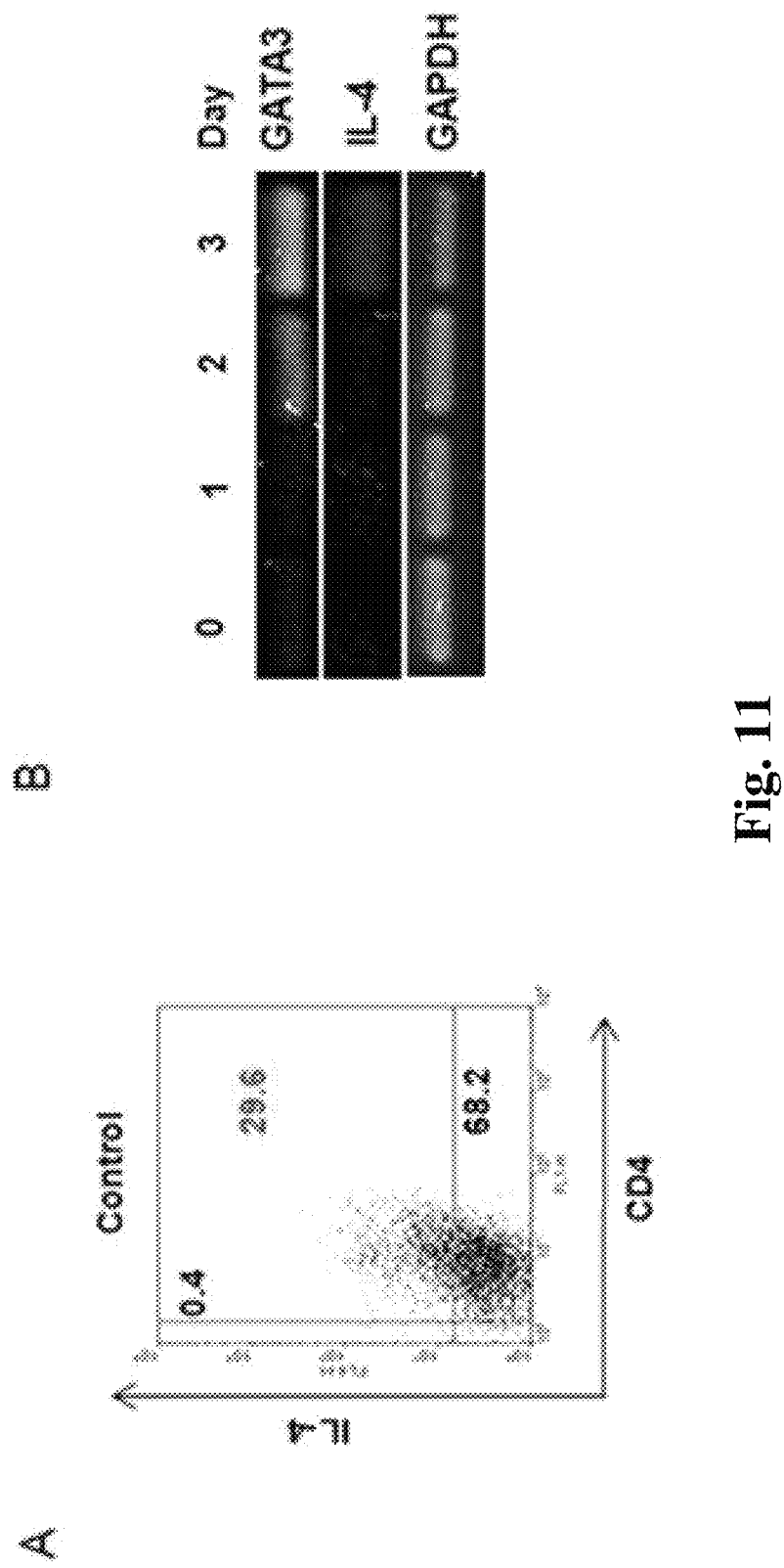
FIG. 11 presents the effect of the inventive purified extract or compounds on the induction of Th2 differentiation from Naive CD4$^+$ T cells (CD4$^+$CD62L+)

As can be seen in FIG. 11, it has been confirmed that the established condition of test was utilized since the degree of differentiation of this condition was determined as 29.6%, similarly to that of conventionally available condition using by the marketed medium for inducing the differentiation of TH2 cells (38%, Merck Milipore, FCIM025162) and the differentiation of TH2 cells was induced at 3rd days after the induction of differentiation by reconfirming the induction of marker expression through RT-PCR (S1000 Thermal cycler, Bio-Rad) experiment using by Th2 differentiation markers (IL-4 and GATA3) to determine their mRNA expression.

3-2. Effect on Mouse Th2 Cell Differentiation

Naive CD4$^+$ T cells (CD4$^+$CD62L$^+$Miltenyi Biotec, 130-093-227) was isolated from the lymph nodes and spleens of C57BL6 mice using by MACS (Miltenyi Biotec, Order no. 130-090-976) and 5, 10, 20 and 40 microgram/ml of ATC2 were treated therewith when the cell was induced to be differentiated into Th2 cell. The degree of Th2 differentiation was determined by the expression of IL-4 differentiation maker.

Figure 12:
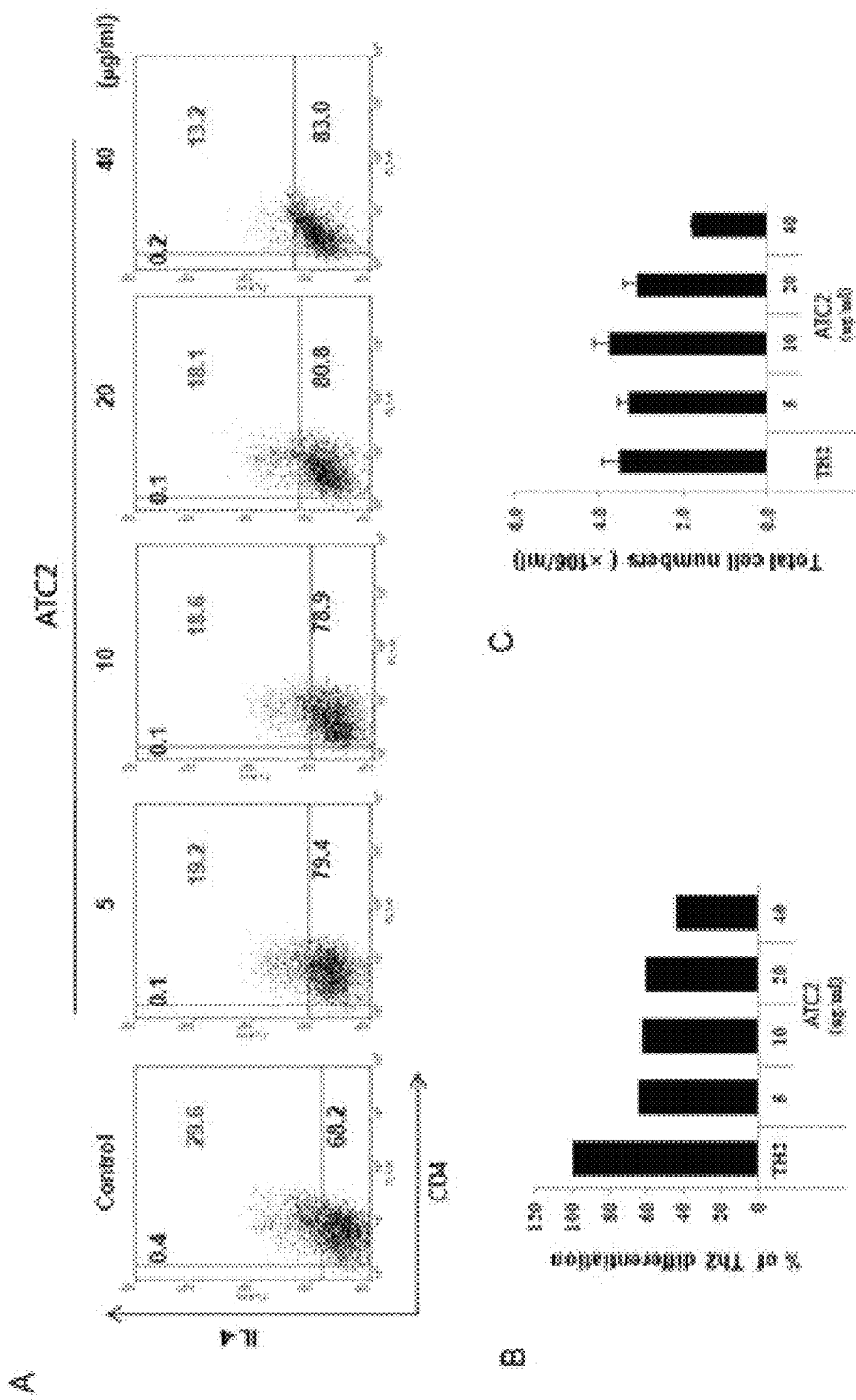
FIG. 12 presents the effect of the inventive purified extract or compounds on the differentiation of Mouse Th2.

As can be seen in FIG. 12, it has been confirmed that the degree of Th2 differentiation in the test group treated with various concentrations of ATC2 has been reduced in a dose dependant manner, 19.2% in case of 5 microgram/ml of ATC2 while that in the control group was 29.6%. However the total number of cells in the test group treated with 20 and 40 microgram/ml of ATC2 were reduced and therefore it has been actually confirmed that less than 10 microgram/ml of ATC2 showed effective inhibitory concentration from Th2 differentiation without affecting on the total number of cells.

Accordingly, it has been confirmed that less than 10 microgram/ml of ATC2 is suitable concentration in the test.

3-3. Effect on the Spectral Change in the Molecular Expression Involved in Th2 Cell Differentiation Naive CD4$^+$ T cells (CD4$^+$CD62L$^+$Miltenyi Biotec, 130-093-227) was isolated from the lymph nodes and spleens of C57BL6 mice using by MACS (Miltenyi Biotec, Order no. 130-090-976) and 2.5, 5, and 10 microgram/ml of ATC2 were treated therewith when the cell was induced to be differentiated into Th2 cell. The degree of Th2 differentiation was determined by the expression of IL-4 differentiation maker.

Figure 13:
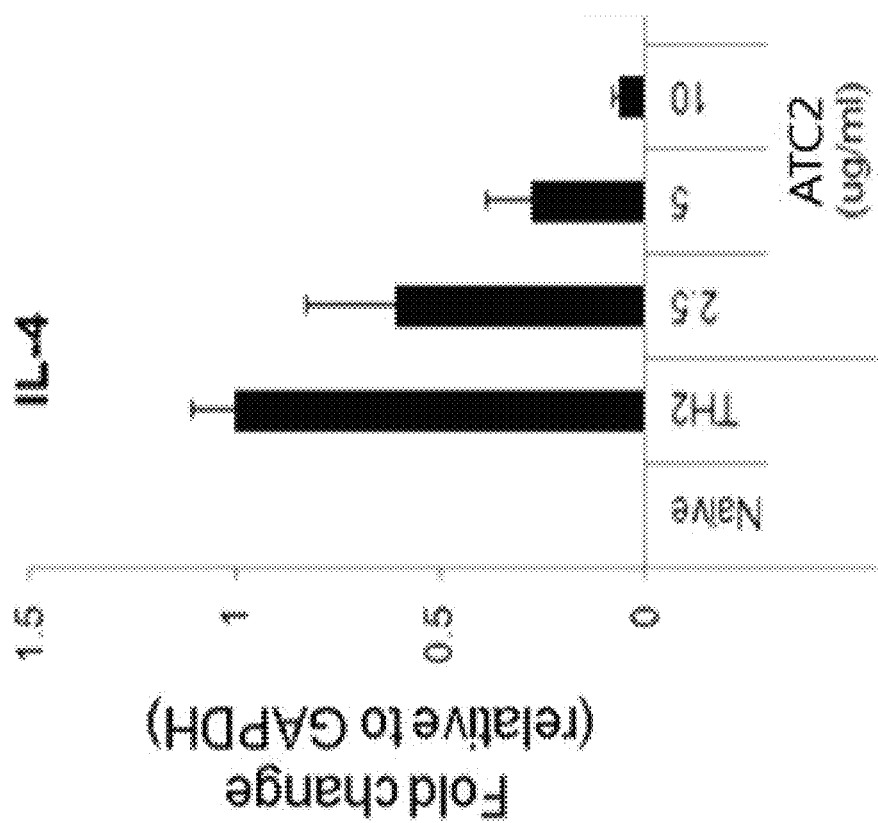
FIG. 13 presents the effect of the inventive purified extract or compounds on the IL-4 expression, a differentiation marker of mouse Th2 cell.

As can be seen in FIG. 13, it has been confirmed that Il-4 expression was induced in only Th2 cell comparing with naive cell and the expression of IL-4 differentiation maker were sharply reduced to about 60% in the group treated with 2.5 microgram/ml of ATC2, about 30% in the group treated with 5 microgram/ml of ATC2, and about 5% in the group treated with 10 microgram/ml of ATC2.

Oxidative stress caused by cigarette smoking or air pollution, give rises to destroying an alveolar maintenance, increasing apoptosis and inflammatory response, inducing the unbalance of protease/anti-protease, and intensifying the inflammation through aging and autoimmune response, thereby resulting in the occurrence of COPD disease after a lapse of 30-50 years. COPD showed particular characteristics for, example, obstruction of air-trapping and emphysema or specific inflammation in lung such as the increased level of macrophage, neutrophil, T-lymphocyte, CD 8 cell, chemokines etc.

The present test analyzed the effective concentration of test samples (ATC2, Verproside, Roflumilast) in COPD induced mice by the intratracheal instillation (i.t.) of LPS and CS.

At the result, it has been confirmed that more than 15 mg/kg of ATC2, 15 mg/kg of verproside and 15 mg/kg of Roflumilast, showed similar inhibition on the number of total immunocyte, neutrophil, and T lymphocyte etc in BALF. More than 15 mg/kg of ATC2, 15 mg/kg of verproside and Roflumilast 15 mg/kg of Roflumilast, showed similar inhibition on the reproduced level of TNF-a, KC/CXCL-1, and MIP-2, a mediator destroying lung alveoli.

Through those result, it has been confirmed that more than 15 mg/kg of ATC2, 15 mg/kg of verproside and 15 mg/kg of Roflumilast, showed potent anti-COPD activity by way of inhibiting the proliferation and activation of neutrophils recruiting to lung caused by the occurrence of COPD.

Experimental Example 4

Animal Model Test (Mice)

In order to determine the anti-COPD effect of inventive extract or compounds on the number of total immunocyte, neutrophil, and T lymphocyte etc in BALF, and the reproduced level of TNF-a, KC/CXCL-1, and MIP-2, following test was performed by using COPD induced mice.

4-1. Experiment Animal

Specific pathogen-free male BALB/c mice (about 18-20 g), aged 8 weeks, which were routinely screened serologically for relevant respiratory pathogens, were purchased from ORIENT Co. (www.orient.co.kr, Seoul, Korea) and bred allowing to access freely to feed and water in breeding room controlling the temperature of 22±2° C., and humidity of 55±15% at the light-dark cycle for 12 hours and acclimated with the experimental environment for 1 week.

4-2. Drug and Administration (1) Test Sample 4 kinds of test samples, i.e., ATC2 (30 mg/kg), Verproside (30 mg/kg), Indacaterol (30 mg/kg), Roflumilast (30 mg/kg) were dissolved in 0.5% CMC (carboxmethylcellulose sodium) and uses as test samples.

(2) Administration 30 mg/kg of each ATC2, Verproside, Indacaterol, and Roflumilast were mixed with 100 μl of the LPS+CS mixture {LPS (100 μg/ml)+standard cigarette extract (Cigarette smoking (CS), 4 mg/ml)=1:1} and orally administrated to the mice, 1 hour before prior the intratracheal instillation (i.t.).

(3) Preparation of Standard Cigarette Extract (Cigarette Smoking; CS)

test material: 60 pieces of standard cigarette CM7 (Coresta Monitering Cigarette 7, Heinr Borgwaldt, Germany) and isopropanol, ethanol (Merck, Germany), n-heptadecane (Sigma-Aldrich, USA) were used as test materials and Automatic smoking machine (ISO 3308 standardized product, automatic smoking machine, model No.: RM20, Heinr Borgwaldt) were used in the experiment.

4-3. Collection of Mainstream Smoke (1) Collection of Mainstream Smoke

Mainstream smoke of standard cigarette CM7 (Coresta Monitering Cigarette 7, Heinr Borgwaldt, Germany) was collected according to the procedure disclosed in KS H ISO (International Organization for Standardization) 3402 standard (Tobacco and tobacco products—Atmosphere for conditioning and testing) and Korean guideline (Determination guideline for the harmful component in Cigarette type smoking desire suppressor, October, 2012, KFDA) and performed in smoking room (temp.: 22±2° C., relative humidity: 60±5%).

The cigarette was combusted according to the smoking procedure ISO standard, i.e., smoked volume (35.0±0.3 ml), smoking interval (60±0.5 sec), smoking time (2.00±0.02 sec) and length of cigarette butt (tipping paper+3 mm, overwrap+3 mm) using by Automatic smoking machine (ISO 3308 standardized product, automatic smoking machine, model No.: RM20/CS, Heinr Borgwaldt, Germany) pursuant to ISO3308 standard (Routine analytical cigarette—Smoking machine—Definition and standard conditions) and TPM (Total Particulate Matter) of cigarette was collected using by 92 mm cambridge filter (ISO3308 standardized product, RM20, Heinr Borgwaldt, Germany) pursuant to ISO3308 standard (KS H ISO3308, 2000).

(2) Weight of Total Particulate Matter (TPM)

The weight of cigarette holder containing pre-combusted cambridge filter was determined according to ISO4387 standard and then the weight of cigarette holder (RM20/CS, Heinr Borgwaldt, Germany) containing cigarette smoke collected by cambridge filter (RM20, Heinr Borgwaldt, Germany) after combustion to calculate TPM content (KS H ISO 4387, 2000; Cigarettes—Determination of total and nicotine-free dry particulate matter using a routine analytical smoking machine) and the Korean guideline (Determination guideline for the harmful component in Cigarette type smoking desire suppressor, October, 2012, KFDA).

At the result, it has been confirmed that the content of TPM in case that standard cigarette has been combusted three times, was determined as 16.0621 mg (19 pieces), 15.9135 mg (20 pieces), 15.5380 mg/cig (20 pieces) respectively. The tested total number of standard cigarette was 59 pieces and TPM was 47.5136 mg.

(3) Extraction of Cigarette TPM

The cambridge filter containing RPM was isolated from cigarette holder and poured to 100 ml erlenmeyer flask. 50 ml of isopropanol 50 ml was added thereto, mixed thoroughly, left alone at room temperature for over 8 hours to extract. After extraction, the solution was filtered, concentrated under vaccuo and transferred to scintillation vial (WHEATON, 03-340-25N, USA) to concentrate under nitrogen gas.

The content of cigarette TPM in mainstream smoke was calculated according to following empirical formulae 1.

$$TPM(mg/cig) = \frac{W_{FHA} - W_{FHB}}{N} \quad \text{Empirical formulae 1}$$

calculation of TPM content wherein TPM denotes Total Particulate Matter;

$W_{FHA}$ denotes the weight of Filter Holder after smoking;

$W_{FHB}$ denotes the weight of Filter Holder before smoking;

N denotes the number of smoked cigarette (vig.)/Trap.

4-4. Test Procedure (1) COPD Animal Model 8 weeks aged BALB/c male mice was anaesthetized with 7% chloral hydrate and 100 μl of LPS+CS mixture {LPS (100 μg/ml)+standard cigarette extract (Cigarette smoking (CS), 4 mg/ml)=1:1} was inhaled to mice (i.t.) for three weeks once a week to prepare COPD animal model. Briefly, 100 μl of LPS+CS mixture was evenly inhaled to nose and mouth of fastened mice (i.t). The tested groups were divided into six groups, i.e., (i) normal group with no treatment (Intact), (ii) control group treated with LPS+CS mixture (COP D-control), (iii) test sample group treated with ATC2 (30 mg/kg, p.o) 1 hr prior to LPS+CS treatment (COP D-ATC2), (iv) test sample group treated with Verproside (30 mg/kg, p.o) 1 hr prior to LPS+CS treatment (COPD-Verproside), (v) test sample group treated with Indacaterol (30 mg/kg, p.o) 1 hr prior to LPS+CS treatment (COPD-Indacaterol), and (vi) test sample group treated with Roflumilast (30 mg/kg, p.o) 1 hr prior to LPS+CS treatment (COP D-Roflumilast). After the end of experiment, the blood, BALF, and pneumonocyte of each mice were isolated and collected to test.

(2) Isolation of PBMCs from Blood and Determination of Cell Number

After the end of experiment, 800~1000 μl of blood was collected from the mice injected with 40 μl of 30 I.U heparin (APU8AF, JW Pharmaceutical, Korea) and then anaesthetized with ethyl ether according to cardiac puncture. 500 μl of collected blood was added to 9.5 ml of ACK solution (A1049201. Invitrogen, USA) and left alone for 5 mins to dissolve erythrocyte. The blood was centrifuged for 5 mins at the speed of 1200 rpm to isolate PBMCs (Peripheral Blood Mononuclear Cell) and stained with 0.04% trypan blue (15250061, Invitrogen, USA) to count the total cell number/ml.

(3) Isolation of BALF (BAL Fluid) and Determination of Total Cell Number

After blood collection, 1 ml of FBS-free/DMEM medium contained in injector was injected to the trachea of autopsied mice, and the mice was fixed with string to circulate the blood three times and isolate the cell from BALF. The blood was isolated, treated with AK solution at 37° C., for 5 mins to dissolve erythrocyte, washed with FBS-free/DMEM medium and stained with 0.04% trypan blue to count total cell number.

(4) Isolation of Lung Cell (Pneumocyte) and Determination of Total Cell Number

Lung was delivered from the mice of which BALF was not isolated and the lung tissue was cut into slices. The slices were added to 3 ml of DMEM medium (LM001-05, Welgene, KOREA) without fetal bovine serum (FBS) and 1 mg/ml of collagenase IV (C5138, Sigma-Aldrich, USA) was added to the medium. The medium was incubated with shaking incubator (KMC480S, VISION SCI, Korea) at 37° C., for 30 mins and the tissue was digested more than four times to isolate pneumocyte. The isolated pneumocyte was washed with medium and allowed to pass through cell strainer (352350, FALCON, USA) to remove the undigested tissues other than cells or impurities. The cell was treated with ACK solution at 37° C., for 5 mins to dissolve erythrocyte, washed again with the medium, and stained with 0.04% trypan blue (15250061, Invitrogen, USA) to count total cell number.

(5) FACS Analysis

The isolated PBMCs, BAL (Bronchoalveolar lavage), and pneumocyte were adjusted to $5 \times 10^5$ cells and performed to immunofluorescence staining at 4° C. PE-anti-CD3e (553064, BD Pharmingen, USA), FITC-anti-CD8 (553031, BD Pharmingen, USA), PE-anti-CD4 (553047, BD Pharmingen, USA), PE-anti-Gr-1 (553128, BD Pharmingen, USA), and FITC-anti-neutrophil (ab55453, Abcam, UK) were added thereto, respectively, and reacted for 30 mins in ice. After the reaction, the cells were washed with phosphate buffered physiological saline solution more than three times and the cell frequency (%) of $CD3^+CD4^+$ & $CD3^+CD8^+$, and $Gr-1^+Neutrophil^+$ was determined using by Cell Quest program (643274, BD Biosciences, USA) of the flow cytometer (FACSCalibur, Becton, Dickinson, USA) and the absolute total number in each tissue was calculated by applying total cells.

(6) ELISA Analysis

The level of IL-1β, IL-6, TNF-a, IL-17, MCP-1, and GRO-a (BioSource, USA) in BALF isolated from mice was determined by enzyme-linked immuno-sorbent assay. Respective antibodies against L-1β, IL-6, TNF-a, IL-17, MCP-1, and GRO-a were diluted with a coating buffer solution (291195, R&D System, USA), coated on a microwell and left alone for overnight at 4° C. Each well was washed three times with washing buffer solution and 100 μl of 10-fold diluted serum was added thereto. The solution was left alone at room temperature for 1 hour, washed twice with washing buffer solution (Tween-20, Sigma-Aldrich, USA), added with 100 μl of antibody Avidin-HRP conjugated (DY998, R&D System, USA), left alone for 1 hour at room temperature and washed again. 100 μl of TMB substrate (555214, BD, USA) was added thereto. The solution was left alone for 30 mins in shadow and added with 50 μl of stop solution (DY994, R&D system, USA) to determine the absorbance using by ELISA leader at 450 nm (340PC384, Molecular Devices, USA).

(7) Determination of mRNA Gene Expression in Lung Tissue (7-1) RNA Isolation from Lung Tissue The lung tissue of mice was delivered and crushed into pieces to be dissolved solved by adding 500 ml of RNAzol$^B$ (CS-105B, Tel-Test, USA). 50 ml of chloroform ($CHCl_3$) was added the mixed floating solution and mixed again for 15 seconds. The solution was left alone for 15 mins in ice, centrifuged at 13,000 rpm to recover about 200 ml of the supernatant and 200 ml of 2-propanol 200 ml was added to equal volume of the supernatant. The mixture was left alone for 15 mins in ice, centrifuged again at 13,000 rpm, washed with 80% EtOH, and dried for 3 mins with vacuum pump (ULVAC, USA) to extract RNA. The extracted RNA was dissolved in 20 ml of distilled water treated with diethyl pyrocarbonate (DEPC, IBS-BW1004, Intron, Korea), and inactivated with heating block (2050, Lab-Line, India) at 75° C. to use in the synthesis of first strand cDNA.

(7-2) Reverse Transcription-Polymerase Chain Reaction

Reverse transcription reaction was performed by the procedure as follows: 2 μg of prepared total RNA in heating block was reacted at 37° C. for 30 mins by adding DNase I (10 U/ml) 2 U/tube, denatured at 75° C. for 10 mins, added with 2.5 ml of 10 mM dNTPs mix (4026, 4027, 4028, 4029, TaKaRA, Japan), 1 ml of random sequence hexanucleotides (25 pmole/25 ml (11034731001, Roche, Germany), 1 ml of RNase inhibitor (2313A, TaKaRa, Japan, 20 U/ml) as RNA inhibitor, 1 ml of 100 mM DTT (P1171, Progmega, USA), 4.5 ml of 5×RT buffer (M531A, Promega, USA), and 250 mM Tris-HCl (pH 8.3, 375 mM KCl, 15 mM $MgCl_2$), added again with 1 ml of M-MLV RT (200 U/ml, M1705, Promega, USA) and the final volume of solution was adjusted to 20 ml by adding distilled water treated with DEPC (diethyl pyrocarbonate). 20 ml of the reaction mixture was mixed thoroughly, centrifuged at 2,000 rpm for 5 second, reacted at 37° C. for 60 mins in heating block to synthesize first-strand cDNA, left alone at 95° C. for 5 mins to inactivate M-MLV RT and the synthesized cDNA was used in polymerase chain reaction (PCR).

(7-3) Real Time Quantitative RT-PCR

The synthesized cDNA was used in Real time quantitative PCR (Galli S J. Allergy, Curr. Biol., 10:R93-95, 2006) using by Applied Biosystems 7500 Real-Time PCR system (Applied Biosystems, USA). CATGTTCCAGTATGACTCCACTCACG (VIC, product provided with Applied Biosystems Co. Ltd.) was used as the probe for TGF-β1, MUC5AC, and mouse glyceraldehyde-3-phosphate dehydrogenase (G3PDH), and Sper-Taqman PCR Master mix (4369016, ABI) was used in the experiment to react to the extent that the final concentration had reached to 200 nM. Real time quantitative PCR was performed as follows: pre-denaturation: at 50° C. for 2 min, at 94° C. for 10 min, and 40 cycles at 95° C. for 0.15 min, at 60° C. for 1 min. G3PDH (4351309, ABI, USA) was used as an internal standard in RME treatment group and control group and RQ (relative quantitative) was calculated according to following empirical formulae 2. (See Table 5)

$$\text{target group Quantitative PCR} y = x(1+e)n \quad \text{Empirical formulae 2}$$

x=starting quantity, y=yield, n=number of cycles, e=efficiency

TABLE 5

Nucleotide sequence of Mouse real-time PCR Oligonucleotide

| Gene | Primer | Sequence |
|---|---|---|
| TGF-β1 | Forward | 5' tggagcaacatgtggaactc 3' |
|  | Reverse | 5' ctgccgtacaactccagtga 3' |
| MUC5AC | Forward | 5' AGAATATCTTTCAGGACCCCTGCT 3' |
|  | Reverse | 5' ACACCAGTGCTGAGCATACTTTT 3' |

(8) Histopathological Examination

Delivered lung was promptly fixed with 10% formaldehyde solution (F0161, SAMCHUN, Korea), and cut into slices. The slices were washed with running water for 8 hrs, embedded with epoxy, cut into slices with microtome (SM2000R, LEICA, Germany), stained with Hematoxylin & Eosin, and Masson-Trichrome stain for collagen deposition staining. To observe the goblet cells, the cells were stained with PAS (Periodic Acid-Schiff) staining to observe by 400× optical microscope (333246, NIKON, Japan).

4-5. Statistics

All the result obtained from various experiments was recorded as mean±standard error, and the verification of significance was determined using by b Student's T-test. The above data was analyzed according to one-way ANOVA test to determine the statistically significant variance between respective group for each determined final point and the statistic significance between each group was determined according to nonparametric Mann-Whitney test and Dunnett's multiple comparison test (IBM SPSS statistics version 19.0 statistic software, Inc, IBM, USA). The difference between each control (COPD-control) was obvious and therefore, it is not shown in figures and tables. The results (presented as mean±standard error of mean) was expressed as P values: $<0.05$ (*), $<0.01$ (), or $<0.001$ (*) as statistically significant.

Figure 14A:
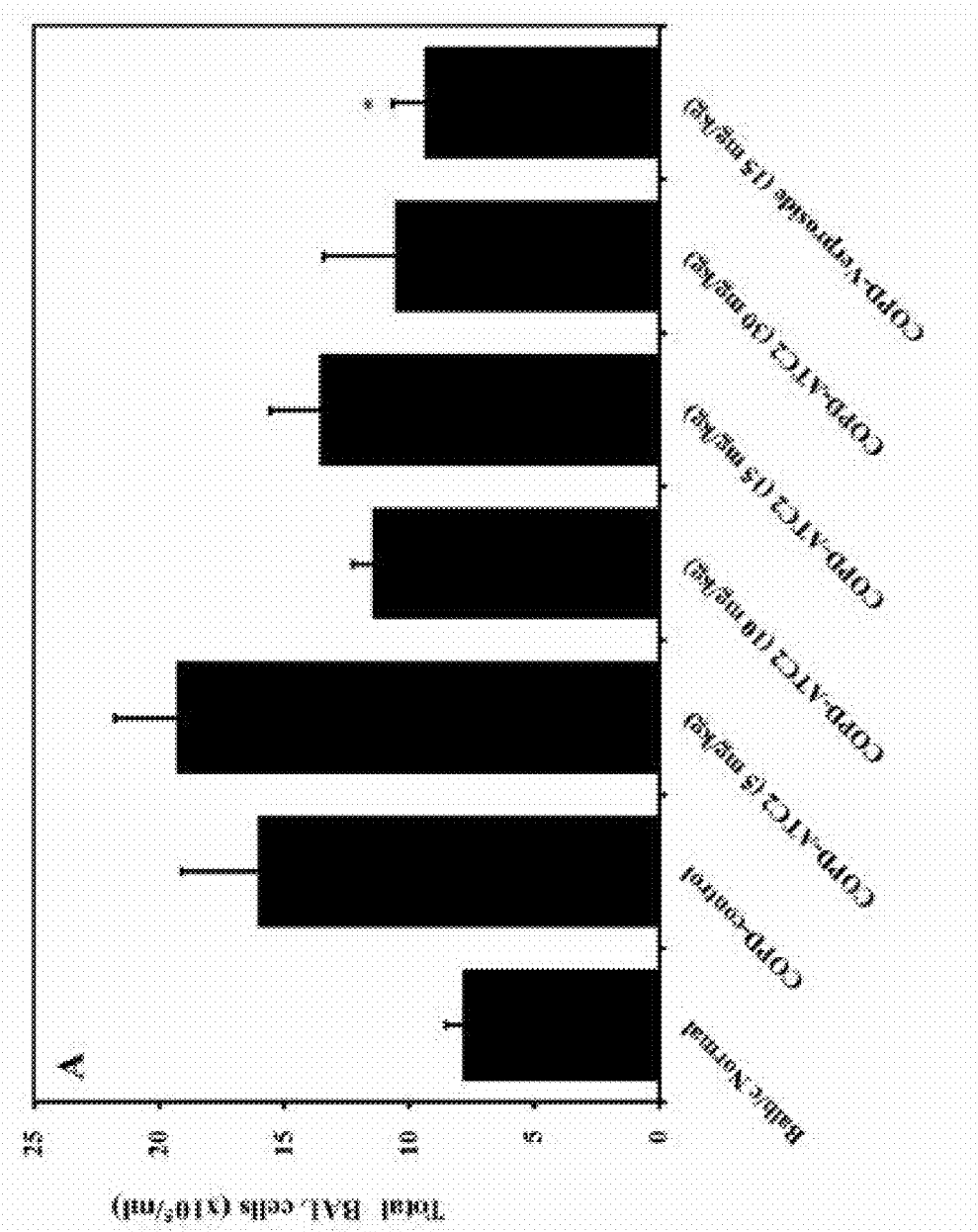
FIG. 14 presents the effect of the inventive purified extract or compounds on the number of total immunocytes, neutrophils and the level of T lymphocyte after the LPS inhalation (i.t) to Balb/c mice and challenge of cigarette smoke.
Figure 14B:
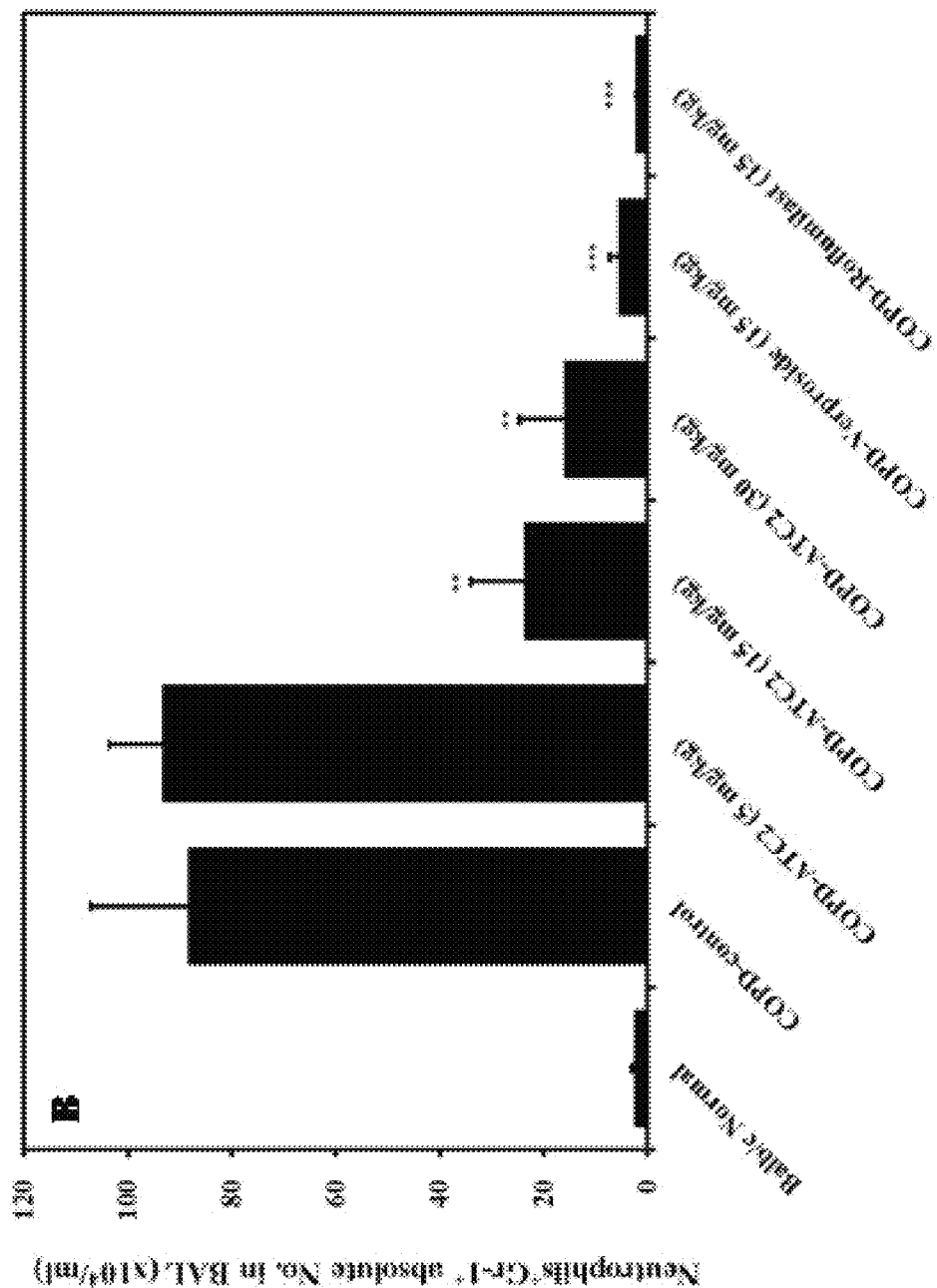

4-6. Test Result (1) Effect on the Number of Total Immunocyte, Neutrophils, and T-Lymphocyte in BALF The cell number of total immunocyte, the total absolute cell number of Nerutrophils$^+$Gr-1$^+$ cell, and the total absolute cell number of CD4$^+$ & CD8$^+$ T cell in control group (COPD-control) were sharply increased compared with those in normal group (Balb/c normal group). The number of total immunocyte in the test group treated with more than 15 mg/kg of ATC2 (5, 10, 15, 30 mg/kg) was reduced compared with control group and those in the test group treated with verproside (15 mg/kg) and Roflumilast (15 mg/kg) ($p<0.05$) was sharply reduced compared with control group (FIG. 14). The total absolute cell number of Nerutrophils$^+$Gr-1$^+$ cell (total absolute No.) in the test group treated with more than 15 mg/kg ($p<0.001$) and 30 mg/kg ($p<0.001$) of ATC2 (5, 10, 15, 30 mg/kg) was reduced by more than 73.2% and 81.9% respectively compared with control group and those in the test group treated with verproside (15 mg/kg) ($p<0.001$) and Roflumilast (15 mg/kg) ($p<0.001$) was reduced by more than 93.9% and 97.5%, respectively, compared with control group (FIG. 14). The total absolute cell number of CD4$^+$ T cell (total absolute No.) in the test group treated with 15 mg/kg (p<0.01) and 30 mg/kg (p<0.001) of ATC2 (5, 10, 15, 30 mg/kg) was reduced by more than 47.7% and 19.7% respectively, compared with control group and those in the test group treated with verproside (15 mg/kg) and Roflumilast (15 mg/kg) (p<0.001) was reduced by more than 32.9% and 73.2%, respectively, compared with control group (FIG. 14c). The total absolute cell number of CD8$^+$ T cell (total absolute No.) in the test group treated with ATC2 (5, 10, 15, 30 mg/kg) and verproside (15 mg/kg) was not significantly different comparing with that in control group while that in the test group treated with Roflumilast (15 mg/kg) (p<0.001) was reduced by more than 67.2% comparing with that in control group (FIG. 14).

At the result, it has been confirmed that the groups treated with more than 15 mg/kg of ATC2 (5, 10, 15, 30 mg/kg), Verproside (15 mg/kg), and Roflumilast (15 mg/kg) showed potent inhibitory effect on the proliferation and activation of inflammatory immunocytes and neutrophils recruiting to lung, resulting in potent anti-COPD activity.

(2) Effect on the Number of Neutrophils in BALF

Figure 15:
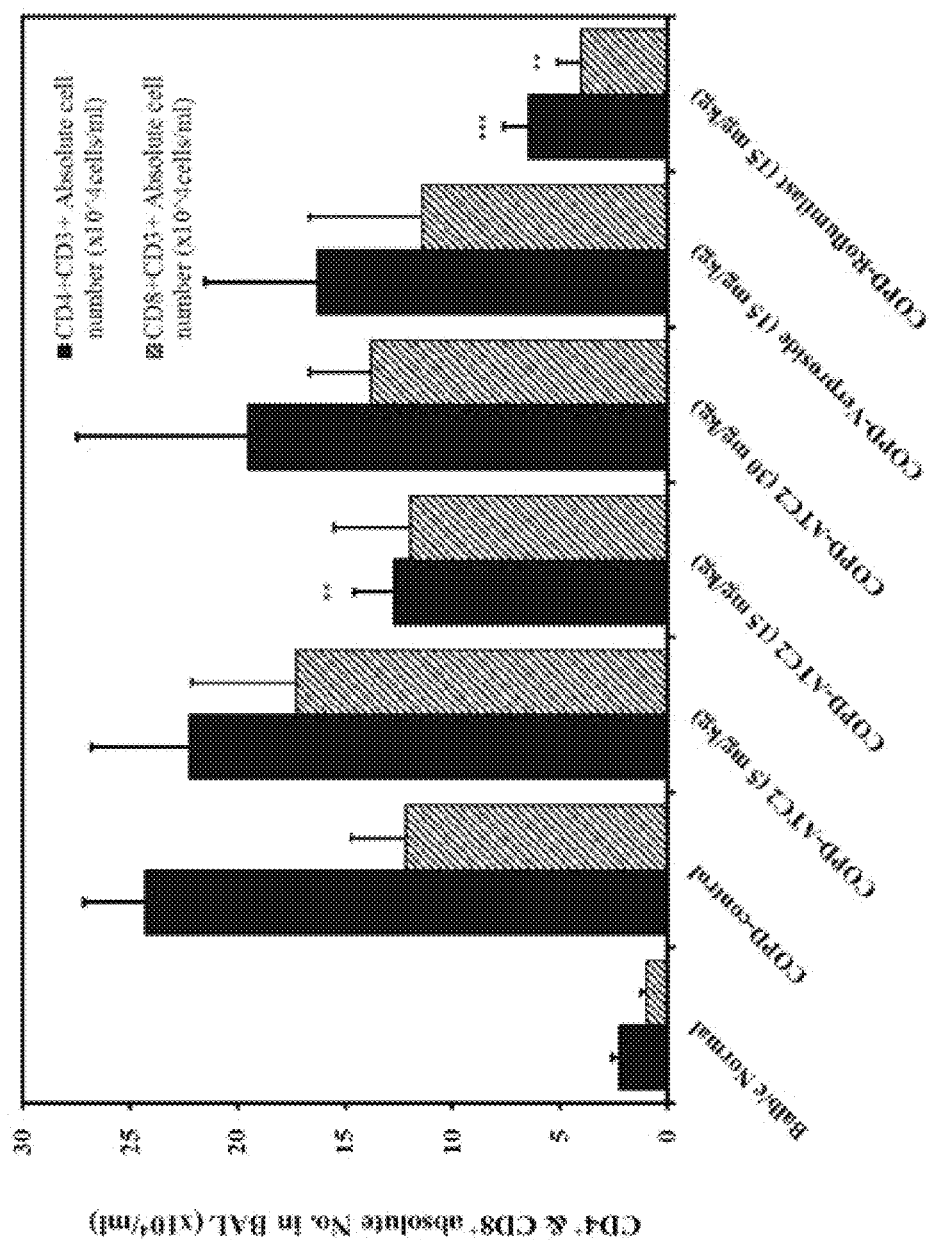
FIG. 15 presents the effect of the inventive purified extract or compounds on the number of CD4$^+$& CD8$^+$ T cells in BALF (A: total cell number ($\times 10^5$)/BALF (ml); B: number of neutrophils ($\times 10^4$)/BALF (ml); C: absolute number of CD4$^+$ & CD8$^+$ T cell ($\times 10^4$)/BALF (ml), data was expressed as mean cell number±SEM ($P<0.05$, $P<0.01$, $P<0.001$ versus LPS+CS; n=10)

The number of Diff-Qick stained neutrophils in the control group (COPD-control) using by cytospin in mice BALF was sharply increased by about 184 folds compared with that in normal group (Balb/c normal group) (FIG. 15). As can be seen in FIG. 15, The number of neutrophils in the groups treated with 15 mg/kg (p<0.001) and 30 mg/kg (p<0.001) of ATC2 (5, 10, 15, 30 mg/kg), were reduced by more than 89.1% and 72.4%, respectively, compared with control group and those in the groups treated with verproside (15 mg/kg)(p<0.001) and Roflumilast (15 mg/kg) (p<0.001) were reduced by more than 94.2% and 99.0%, respectively, compared with control group.

At the result, it has been confirmed that the groups treated with more than 15 mg/kg of ATC2 (5, 10, 15, 30 mg/kg), Verproside (15 mg/kg), and Roflumilast (15 mg/kg) showed potent inhibitory effect on the proliferation of neutrophils recruiting to lung, resulting in potent anti-COPD activity.

(3) Effect on the Reproduction of CXCL-1, TNF-α, and MIP-2 in BALF

Various chemokines MIP-2/CXCL-2, TNF-α and protease etc released from produced from the inflammatory macrophage in lung tissue destroy an alveolar layer, and KC/CXCL-1 (Chemokines Gro-α) and CXCL-8 stimulate neutrophil, release protease and thereby destroy alveolae again, resulting in COPD (Blidberg K, Palmberg L, Dahlen B, Lantz A S, Larsson K. 2012. Chemokine release by neutrophils in chronic obstructive pulmonary disease. Innate Immun. 18: 503-510).

Figure 16A:
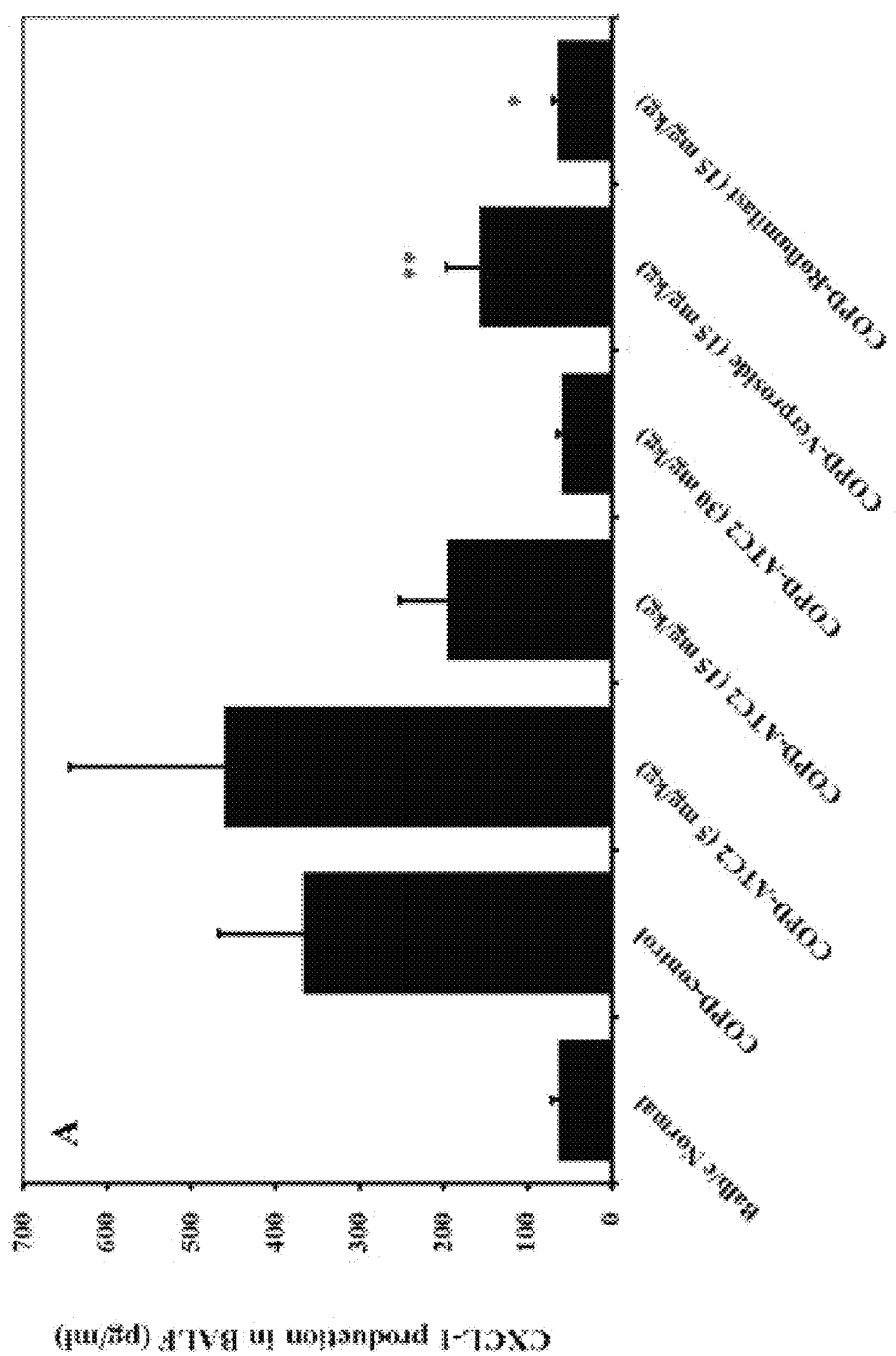
FIG. 16 presents the effect of the inventive purified extract or compounds on the level of CXCL-1, TNF-α, and MIP-2 after the LPS inhalation (i.t) to Balb/c mice and challenge of cigarette smoke.
Figure 16B:
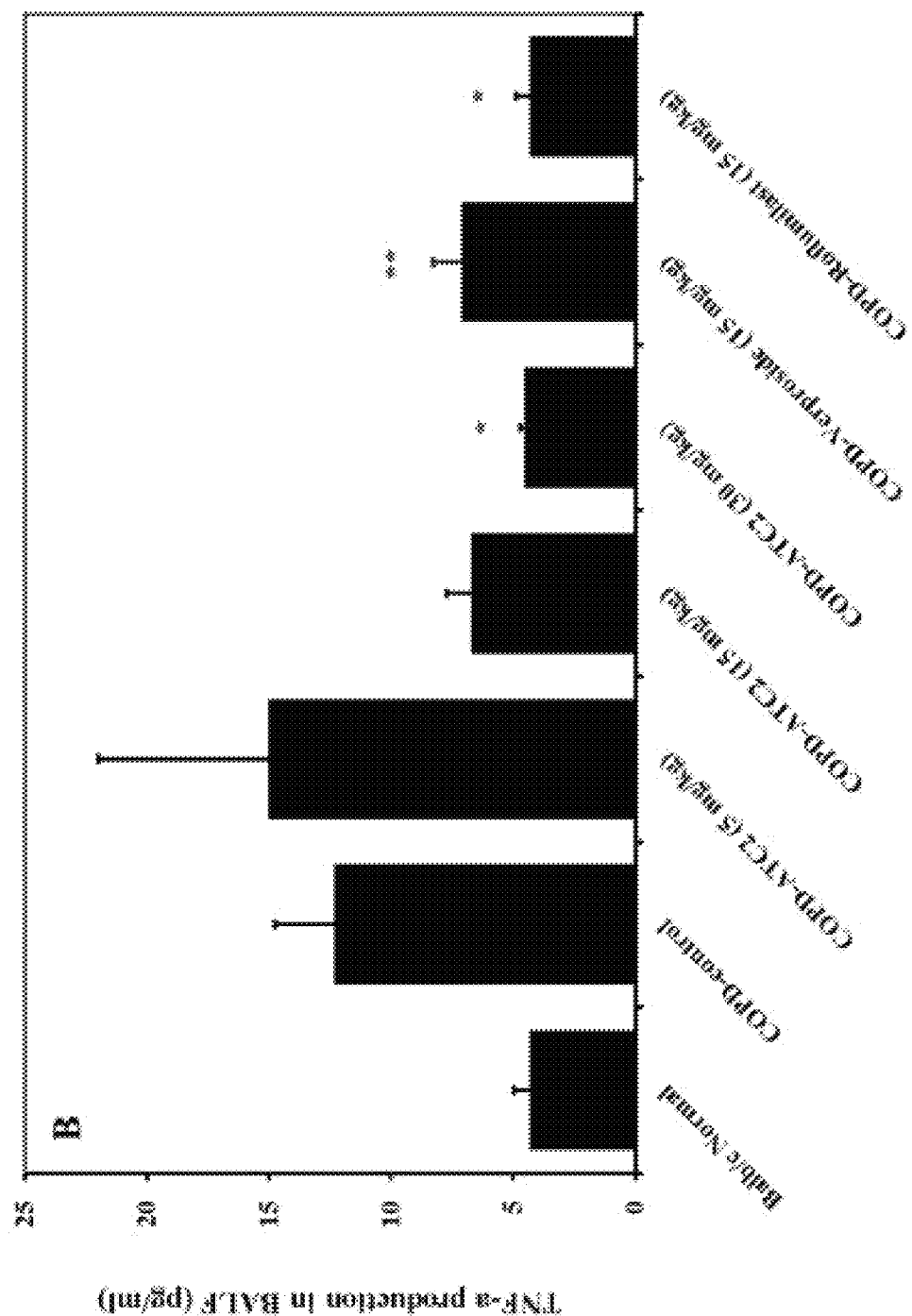
Figure 16C:
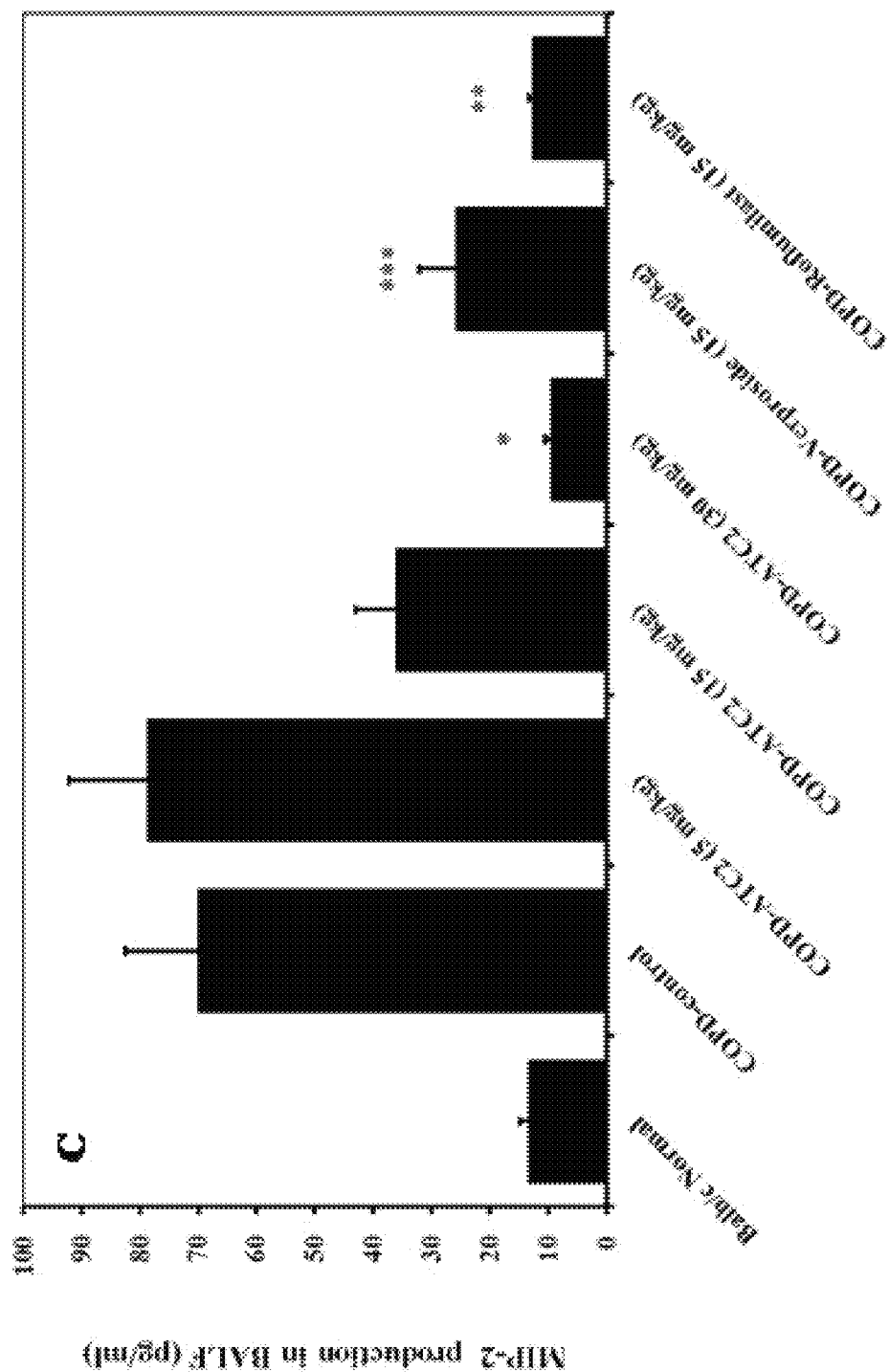

As can be seen in FIG. 16A showing the reproduction of chemokine KC/CXCL-1 (Chemokines Gro-α) of BALF in mice determined by ELISA method, the reproduction of chemokine KC/CXCL-1 (Chemokines Gro-α) in the control group has been sharply increased by about 5.9 folds compared with that in the control group (Balb/c normal group). The reproduction of chemokine KC/CXCL-1 (Chemokines Gro-α) in the group groups treated with 15 mg/kg and 30 mg/kg (p<0.01) of ATC2 (5, 10, 15, 30 mg/kg), were reduced by more than 46.8% and 83.9%, respectively, compared with control group and those in the group treated with verproside (15 mg/kg)(p<0.05) and Roflumilast (15 mg/kg) (p<0.01) were reduced by more than 57.4% and 82.7%, respectively, compared with control group. As can be seen in FIG. 16B showing the reproduction of TNF-α of BALF in mice determined by ELISA method, the reproduction of TNF-α in the control group has been sharply increased by about 2.8 folds compared with that in the control group (Balb/c normal group). The reproduction of TNF-α in the group groups treated with 15 mg/kg (p<0.05) and 30 mg/kg (p<0.01) of ATC2 (5, 10, 15, 30 mg/kg), were reduced by more than 45.5% and 63.4%, respectively, compared with control group and those in the group treated with verproside (15 mg/kg)(p<0.05) and Roflumilast (15 mg/kg) (p<0.01) were reduced by more than 42.2% and 65.0%, respectively, compared with control group. oup. As can be seen in FIG. 16C showing the reproduction of chemokines MIP-2/CXCL-2 of BALF in mice determined by ELISA method, the reproduction of chemokines MIP-2/CXCL-2 in the control group has been sharply increased by about 5.2 folds compared with that in the control group (Balb/c normal group). The reproduction of chemokines MIP-2/CXCL-2 in the group groups treated with 15 mg/kg (p<0.05) and 30 mg/kg (p<0.001) of ATC2 (5, 10, 15, 30 mg/kg), were reduced by more than 48.4% and 86.4%, respectively, compared with control group and those in the group treated with verproside (15 mg/kg)(p<0.01) and Roflumilast (15 mg/kg) (p<0.001) were reduced by more than 63.0% and 81.9%, respectively, compared with control group.

At the result, it has been confirmed that the groups treated with more than 15 mg/kg of ATC2 (5, 10, 15, 30 mg/kg), Verproside (15 mg/kg), and Roflumilast (15 mg/kg) showed potent inhibitory effect on the reproduction of chemokines MIP-2/CXCL-2, TNF-α, KC/CXCL-1 (Chemokines Gro-α) and CXCL-8 etc involved in the destruction of lung cell, resulting in potent anti-COPD activity.

Experimental Example 5

Animal Model Test (Rat)

In order to determine the anti-COPD effect of inventive extract or compounds on the number of total immunocyte, neutrophil, etc in BALF, the reproduced level of cytokines such as IL-1 beta, IL-6, TNF-a, the activation of MMP-9, the expression of proinflammatory proteins such as MMP-9, NF-kB, and the inflammatory response in lung tissue, following test was performed by using COPD induced mice.

5-1. Experiment Animal

Specific pathogen-free male Sprague-Dawley eat (about 180-200 g), aged 6 weeks, which were routinely screened serologically for relevant respiratory pathogens, were purchased from ORIENT Co. (www.orient.co.kr, Seoul, Korea) and bred allowing to access freely to feed (antibiotic free, Samyang Oil & Feed Corp., Korea) and water in breeding room controlling the temperature of 22±2° C., and humidity of 55±15% at the light-dark cycle for 12 hours and acclimated with the experimental environment for 1 week.

5-2. Drug and Administration (1) Test Sample 3 kinds of test samples, i.e., ATC2 (30 mg/kg), Verproside (30 mg/kg), Daxas (main ingredient: Roflumilast, 1 mg/kg) were dissolved in PBS and uses as test samples.

(2) Administration

ATC2, Verproside, Daxas were orally administrated to the mice at the dose of 4 mg/kg, 1 hour before prior the intratracheal instillation (i.t.).

5-3. Preparation of COPD Rat Model (1) Standard Cigarette

3R4F Kentucky Reference Cigarettes (University of California, USA) was used as a standard cigarette for generating a cigarette smoke. The cigarette containing 9.4 mg of tar, 11 mg of TPM (total particle matter) and 12 mg of carbon monooxide per piece, was used after harmonizing with the temperature of 22±1° C. and humidity of 60±2% after opening for 48~72 hrs.

(2) Procedure

The exposure of cigarette smoke was performed by using a cigarette smoke generator (CH Technology Corp. USA). In a detail, 1 hour after the orally administration of test samples using by Head/nose-only exposure unit (TSE System, German) according to nose-only method, the cigarette smoke was exposed by inhalation for 3 days every hour. 8 puffs (volume 35 ml, duration 2 sec, interval 1 time/min) per one piece of standard cigarette was performed in the experiment. The tested groups were divided into five groups, i.e., (i) normal group with no treatment (normal control, NC), (ii) control group exposed with cigarette smoke (COPD), (iii) test sample group treated with Daxas (1 mg/kg, p.o) 1 hr prior to cigarette smoke exposure (DA), (iv) test sample group treated with ATC2 (30 mg/ml, p.o) 1 hr prior to cigarette smoke exposure (YPL), and (v) test sample group treated with Verproside (30 mg/ml, p.o) 1 hr prior to cigarette smoke exposure (Ver). After the end of experiment, the blood, BALF, and pneumonocyte of each rat were isolated and collected to test.

5-4. BALF Isolation and Determination of the Number of Immunocytes

After finishing the experiment, rats were anesthetized with Zoletil50 (3VX9, Virbac, France, p.o) and the blood was delivered through caudal veins. In order to isolate BALF from lung, the bronchus of right lung was ligated with suture and then performed to tracheotomy. IV-use catheter (16 GA, 3S-Cath, Dukwoo, Korea) was put into the bronchus, and both of bronchus and catheter (16 GA, 3S-Cath, Dukwoo, Korea) were fixed with suture. The injector containing 5 ml of DPBS (Dubecco's phosphate-buffered saline, 14190-250, Invitrogen, USA) was connected thereto and DPBS was forced to circulate three times to isolate BALF. The light lung ligated with suture was isolated, fixed with 10% neutral formalin solution, and the remaining lung tissue was reserved in refrigerator at −70° C. The isolated BALF was centrifuged for 15 mins at 1500 rpm to prepare cell pellet and the supernatant was reserved in refrigerator at −70° C. for cytokine analysis. The cell pellet was suspended in DPBS, and the cell was attached to a slide glass using by cytospin centrifuge (CS03270047, Hanil, Korea). Diff-Quik staining (ZS1003, Sysmex, Japan) was performed and the cell was observed by optical microscopy (DM1000, Leica, German) to count the number of immunocyte in each test sample.

5-5. Cytokine Analysis in BALF

The level of IL-1β, IL-6, and TNF-a (R&D System, USA) in BALF isolated from the rat was determined by enzyme-linked immuno-sorbent assay (ELISA). The analysis of each cytokine was performed according to the manufacturer's manual, and the absorbance was determined at 450 nm by ELISA leader (340PC384, Molecular Devices, USA).

5-6. The Determination of the Expression of Immunocytes (1) Gelatin Zymography

The lung tissue of rat was homogenized with Tissue lysis buffer (C3228, Sigma-Aldrich, USA) treated with a protease inhibitor (11836153001, Roche, Germany) and the homogenized lung tissue was centrifuged at 12000 rpm for 10 mins to isolate the supernatant. The protein assay reagent (500-0006, Bio-Rad, USA) was used to quantification. To determine the activity of MMP-9, sodium dodecyl sulfate-polyacrylamide gel electrophoresis (SDS-PAGE) containing 1% gelatin (G9382, Sigma-Aldrich, USA) was used in the experiment. The protein was performed to electrophoresis with the dose of 60 μg/lane. Zymogram gel was washed with 2.5% Triton X-100 (0694, Amresco, USA), and reacted for 16 hrs at 37° C. using by developing buffer (1M Tris-HCl, pH 7.5 with $CaCl_2$, T1503, Sigma-Aldrich, USA). After finishing the reaction, zymogram gel was stained using by Coomassie brilliant blue (0472, Amresco, USA) and washed with a destaining buffer {500 ml of Methanol (M1447, Samchun, Korea)+1400 ml of D.W+160 ml of acetic acid (9151, J. T. Baker)}. The density of MMP-9 band was determined using by Chemi-doc (170-8070, Bio-Rad, USA) to determine the activity of MMP-9.

(2) Western Blotting

The protein obtained from homogenization was performed to electrophoresis at the dose of 30 μg/lane and transferred using by polyvinylidene difluoride (PVDF) membrane (IPVH00010, Millipore, USA). The membrane (IPVH00010, Millipore, USA) was blocked with 5% skim milk and then reacted with anti-MMP-9 (ab38898, Abcam, UK), anti-p65 (sc-372, Santa Cruz, USA) and anti-p-p65 (sc-33039, Santa Cruz, USA) antibodies. After finishing the reaction, the membrane was washed with TBST (Tris-buffered saline containing 0.05% Tween-20, HT2008, Biosesang, Korea) and reacted with suitable secondary antibody (sc-358914, Santa Cruz, USA) at room temperature for 1 hour. The membrane was washed again with TBST and the band was confirmed by using chemiluminescence kit (34095, Thermo, USA).

5-7. Histopathological Examination

Delivered lung was promptly fixed with 10% formaldehyde solution (F0161, SAMCHUN, Korea), and cut into slices. The slices were washed with running water for 8 hrs, embedded with epoxy, cut into slices with microtome (CUT4050, MicroTec, Germany) and stained with Hematoxylin (MHS-16, Sigma-Aldrich, USA) & Eosin (HT110-1-32, Sigma-Aldrich, USA). To observe the Histopathological change in lung tissue, the cells were observed by 400× optical microscope (DM1000, Leica, Germany).

5-8. Statistics

All the result obtained from various experiments was determined using by one-way ANOVA test and the statistical significance between respective group was verified according to Dunnett's multiple comparison test for post hoc comparison result.

5-9. Test Result (1) Effect on the Number of Total Immunocyte in BALF

Figure 17:
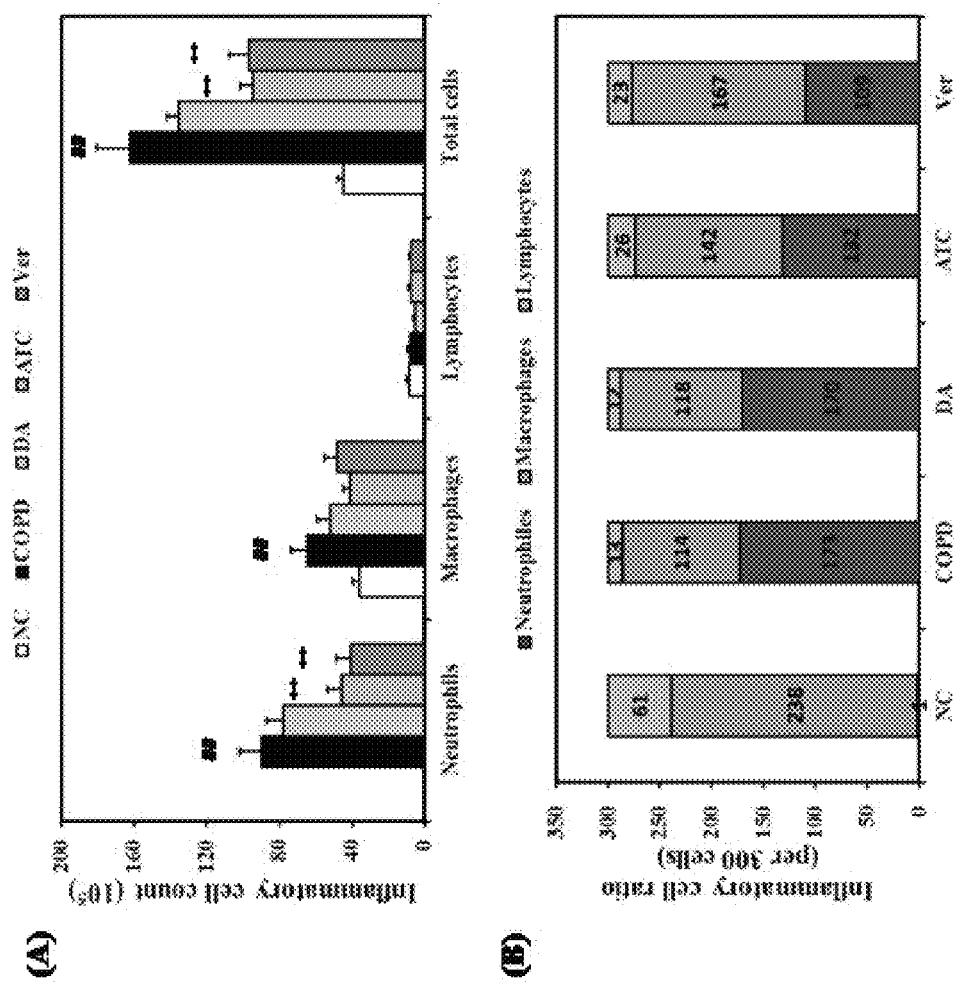
FIG. 17 presents the effect of the inventive purified extract or compounds on the number of inflammatory cells.

The characteristic increased level of neutrophils was observed in COPD induced group. The drug control group treated with Daxas showed reduced level of neutrophils however it is not remarkable compared with COPD induced group. In a while, the groups treated with ATC2 and verproside showed remarkably reduced level of neutrophils and total immunocytes compared with COPD induced group (FIG. 17A). The reduction was observed in the ratio between the level of neutrophils and total immunocytes. The positive control group treated with Daxas showed similar ratio of the number of neutrophils to that of immunocytes in case of counting 300 immnocytes to COPD induced group whereas the groups treated with ATC2 and verproside showed remarkably reduced ratio of the number of neutrophils (FIG. 17B).

(2) Effect on the Cytokine Release in BALF

Figure 18:
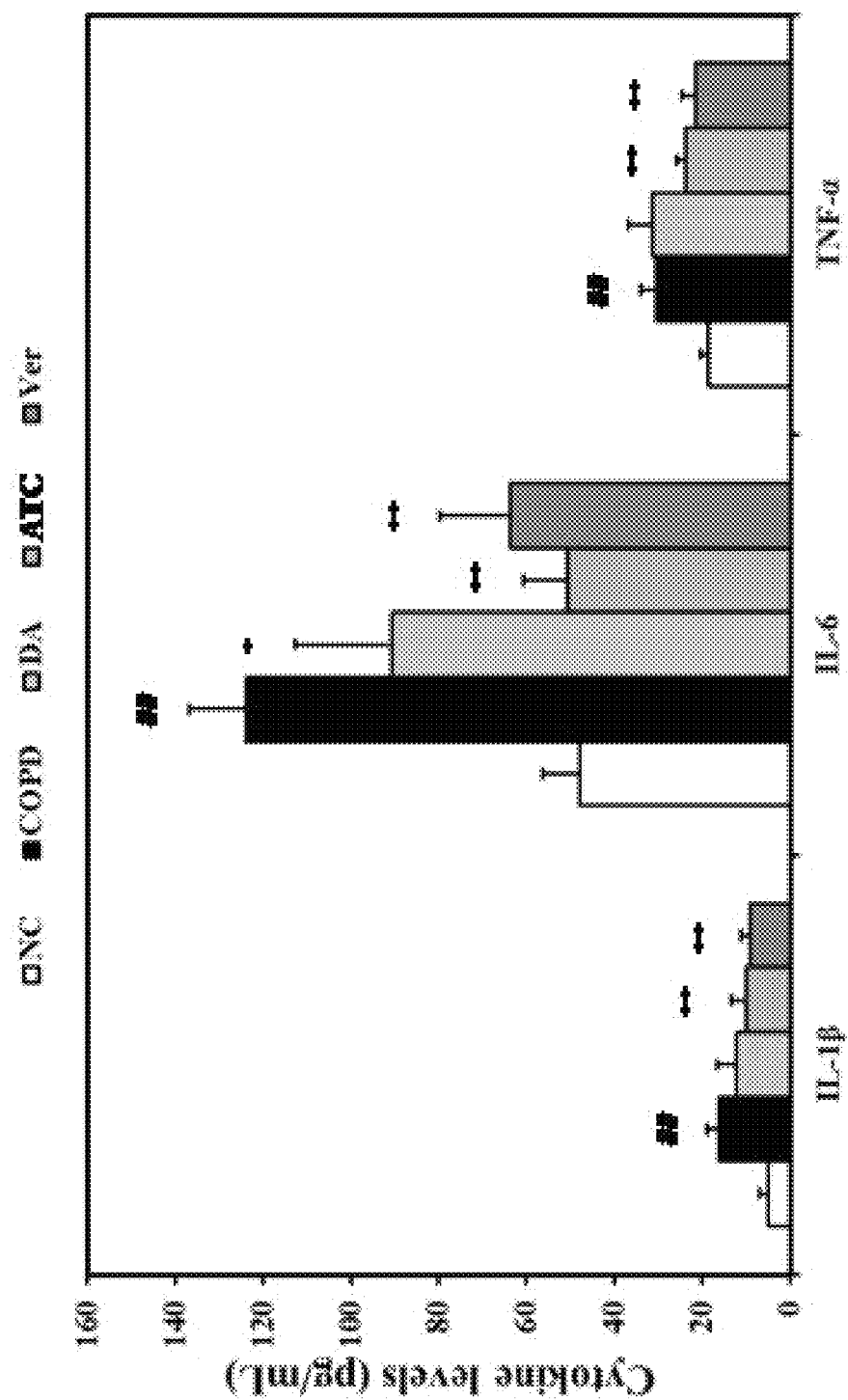
FIG. 18 presents the effect of the inventive purified extract or compounds on the total cell number in BALF.

In COPD induced group, the level of IL-1β, IL-6, and TNF-α were sharply increased in BALF. The drug control group treated with Daxas did not show significant reduction in the level of cytokines compared with COPD induced group. In a while, the groups treated with ATC2 and verproside showed significantly reduced level of cytokines compared with COPD induced group, of which level was sharply reduced compared with drug control group treated with Daxas (FIG. 18).

(3) Effect on the Activity of MMP-9 in Lung Tissue

Figure 19:
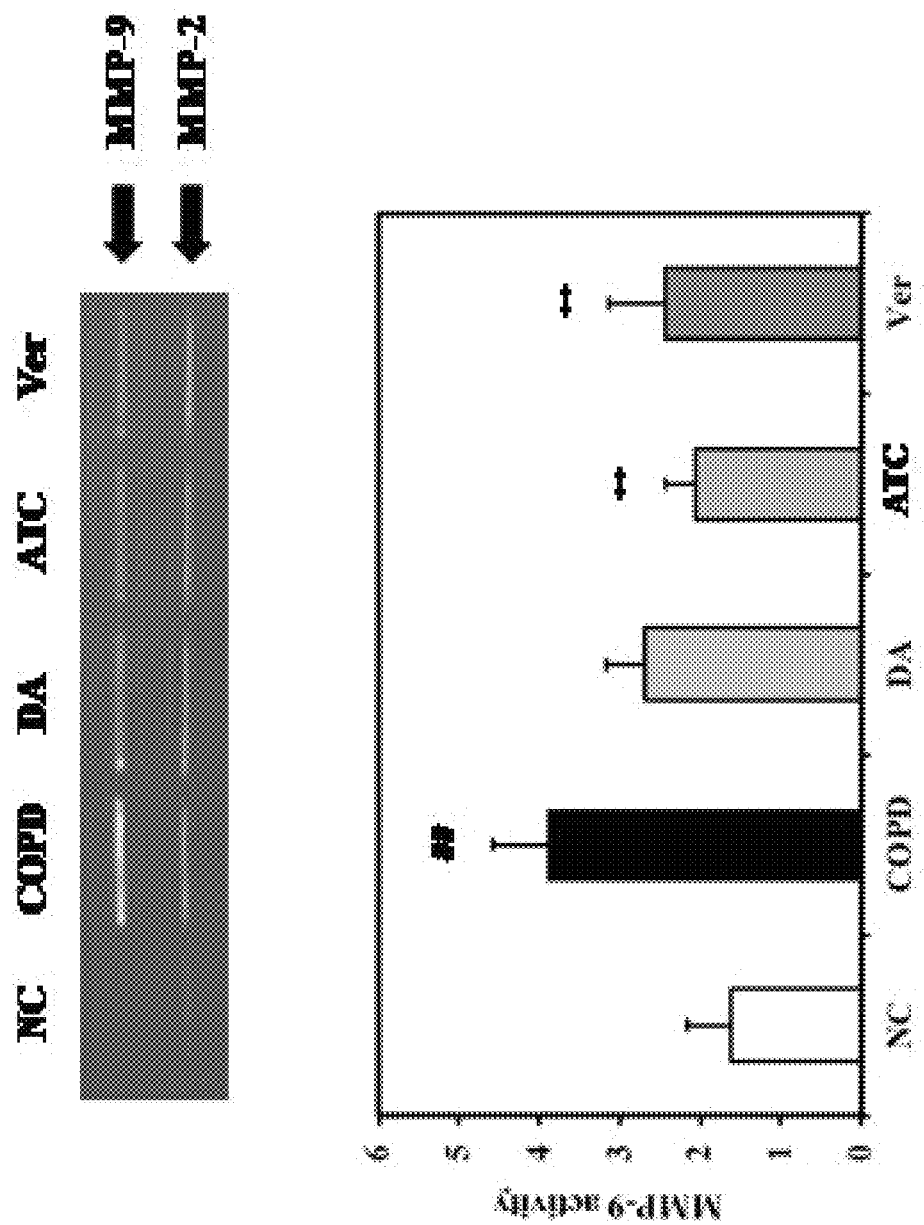
FIG. 19 presents the effect of the inventive purified extract or compounds on the MMP-9 activity in lung tissue.

In COPD induced group, the activity of MMP-9, an important mediator involved in inflammation and the degradation of extracellular matrix, was remarkably increased. In a while, the groups treated with ATC2 and verproside showed remarkably reduced activity of MMP-9, of which level was similar to the drug control group treated with Daxas (FIG. 19).

(4) Effect on the Expression of Proinflammatory Protein in Lung Tissue

Figure 20:
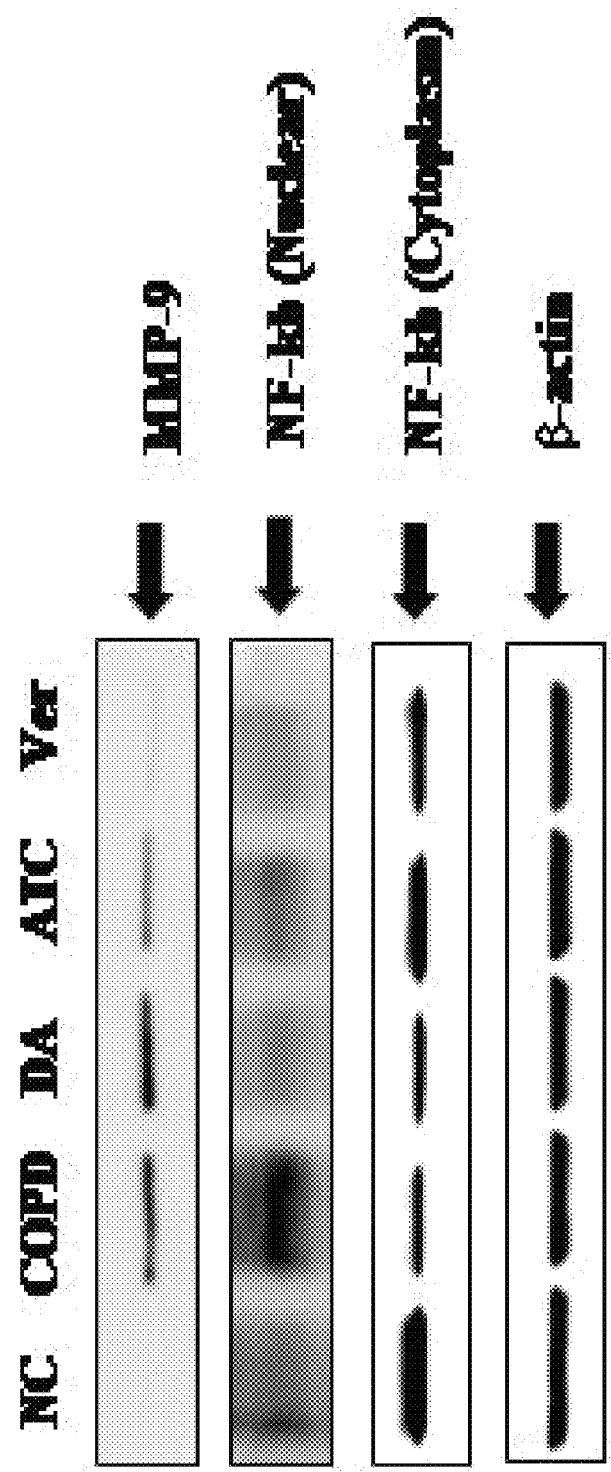
FIG. 20 presents the effect of the inventive purified extract or compounds on the expression of proinflammatory proteins in lung tissue.

In COPD induced group, the activity of proinflammatory proteins such as MMP-9 and NF-κB, was remarkably increased. However, such increased expression of proinflammatory protein in COPD induced group, was significant decreased in the groups treated with ATC2 and verproside, similarly to the drug control group treated with Daxas (FIG. 20).

(5) Effect on the Inflammation in Lung Tissue

Figure 21:
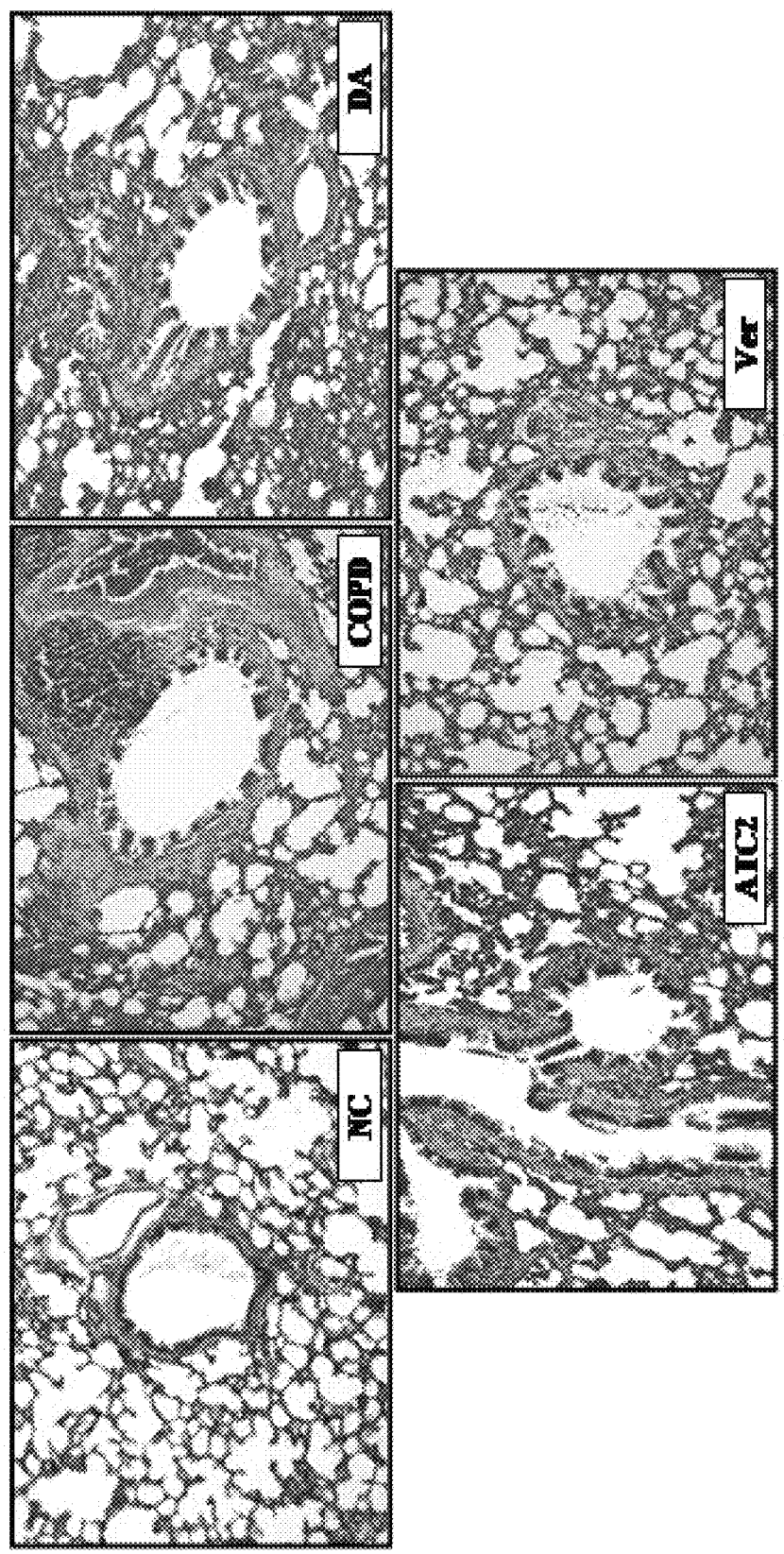
FIG. 21 represents the inhibitory effect of the inventive purified extract on the inflammatory response in lung tissue cell using by the histological examination of bronchoalveolar lavage.

In COPD induced group, there showed the infiltration of many inflammatory cells within bronchus, perivascular tissue and interstitial tissue etc. However, such increased inflammation in COPD induced group, was significant decreased in the groups treated with ATC2 and verproside as well as the drug control group treated with Daxas, the inhibitory effect on inflammation in the groups treated with ATC2 and verproside was more potent than that in the drug control group treated with Daxas (FIG. 21).

At the result, it has been confirmed that ATC2 and the compounds isolated therefrom, verproside etc, have potent treating effect on COPD by way of inhibiting the release of IL-1β, IL-6, or TNF-α, the activation of NF-κB, and the expression of MMP-9, a main cause of COPD. Those treating activity of inventive extract or compounds are confirmed to be similar or more potent than conventionally available COPD treating agent (Daxas).

Experimental Example 6

Acute Toxicity Test of Oral Administration in Rat

The acute toxicity test was performed by administrating inventive extract and compounds to 6-weeks aged SPF Sprague-Dawley rats.

250 mg/kg, 500 mg/kg, 1000 mg/kg, 5000 mg/kg of inventive extract and compounds was orally administrated to each group consisting of 2 rats and the symptoms of rats were observed for 14 days. After administrating the extract or compounds, all the clinical changes i.e., mortality, clinical signs, body weight changes was observed and blood test such as haematological test and hematological biochemistry test was performed. The abnormal changes of abdominal organ and thoracic organ were observed after autopsy.

There did not show any changes in mortality, clinical signs, body weight changes and gross findings in any group or either gender. Furthermore, there showed any toxicity in test group treated with 5000 mg/kg of inventive extract or compounds.

Accordingly, it has been confirmed that the inventive extract and compounds prepared in the present invention was potent and safe substance showing $LD_{50}$ (more than 5000 mg/kg) in oral administration.

MODE FOR INVENTION

Hereinafter, the formulating methods and kinds of excipients will be described, but the present invention is not limited to them. The representative preparation examples were described as follows.

Preparation of Injection

| ATC1 extract | 100 mg |
| Sodium metabisulfite | 3.0 mg |
| Methyl paraben | 0.8 mg |
| Propyl paraben | 0.1 mg |
| Distilled water for injection | optimum amount |

Injection preparation was prepared by dissolving active component, controlling pH to about 7.5 and then filling all the components in 2 ml ample and sterilizing by conventional injection preparation method.

Preparation of Powder

| ATC2 extract | 500 mg |
| Corn Starch | 100 mg |
| Lactose | 100 mg |
| Talc | 10 mg |

Powder preparation was prepared by mixing above components and filling sealed package.

Preparation of Tablet

| verproside | 200 mg |
| Corn Starch | 100 mg |
| Lactose | 100 mg |
| Magnesium stearate | optimum amount |

Tablet preparation was prepared by mixing above components and entabletting.

Preparation of Capsule

| veratric acid | 100 mg |
| Lactose | 50 mg |
| Corn starch | 50 mg |
| Talc | 2 mg |
| Magnesium stearate | optimum amount |

Tablet preparation was prepared by mixing above components and filling gelatin capsule by conventional gelatin preparation method.

Preparation of Liquid

| catalposide | 1000 mg |
| Sugar | 20 g |
| Polysaccharide | 20 g |
| Lemon flavor | 20 g |

Liquid preparation was prepared by dissolving active component, and then filling all the components in 1000 Ml ample and sterilizing by conventional liquid preparation method.

Preparation of Health Food

| ATC2 extract | 1000 mg |
| Vitamin mixture | optimum amount |
| Vitamin A acetate | 70 g |

-continued

| | |
|---|---|
| Vitamin E | 1.0 mg |
| Vitamin B$_{10.}$ | 13 mg |
| Vitamin B$_2$ | 0.15 mg |
| Vitamin B6 | 0.5 mg |
| Vitamin B1 | 20.2 g |
| Vitamin C | 10 mg |
| Biotin | 10 g |
| Amide nicotinic acid | 1.7 mg |
| Folic acid | 50 g |
| Calcium pantothenic acid | 0.5 mg |
| Mineral mixture | optimum amount |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |
| Potassium citrate | 90 mg |
| Calcium carbonate | 100 mg |
| Magnesium chloride | 24.8 mg |

The above mentioned vitamin and mineral mixture may be varied in many ways. Such variations are not to be regarded as a departure from the spirit and scope of the present invention.

Preparation of Health Beverage

| | |
|---|---|
| 6-O-veratroyl catalpol | 1000 mg |
| Citric acid | 1000 mg |
| Oligosaccharide | 100 g |
| Apricot concentration | 2 g |
| Taurine | 1 g |
| Distilled water | 900 ml |

Health beverage preparation was prepared by dissolving active component, mixing, stirred at 85° C. for 1 hour, filtered and then filling all the components in 1000 ml ample and sterilizing by conventional health beverage preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

As described in the present invention, inventive purified extract containing abundant active ingredients such as catalpol derivatives from the extract of *Pseudolysimachion rotundum* var *subintegrum* or at least one compounds selected from the group consisting of veratric acid, verproside, catalposide, picroside II, isovanilloyl catalpol and 6-O-veratroyl catalpol showed potent anti-COPD activity without beta-2-receptor agonistic response through various in vivo tests using by BALB/c male mice, for example, an inhibition test on the proliferation and activity of inflammatory immunocytes and neutrophils recruiting to lung caused by COPD occurrence; an inhibition test on the reproduction of chemokines involved in the destruction of pneumocyte, such as MIP-2/CXCL-2, TNF-alpha, KC/CXCL-1 (Chemokines Gro-alpha) and CXCL-8 etc; the reducing effect on the release of IL-1beta, IL-6, TNF-alpha and MMP-9 expression by decreasing NF-kappaB activation in animal test using by SPF (specific pathogen-free) Sprague-Dawley rat, as well as in vitro test, for example, an inhibition test on the expression of MUC5AC (oligomeric muscus/gel-forming), inducing effect on the IL-4-expression of Th2 cell in molecular expression profiling change test etc. Therefore, it can be used as the therapeutics or functional health food for treating and preventing chronic obstructive pulmonary disease (COPD). preventing chronic obstructive pulmonary disease (COPD).

The invention claimed is:

1. A method of treating chronic obstructive pulmonary disease (COPD) in mammals, wherein the method comprises administering a therapeutically effective amount of the purified extract with the secondary fractionation (ATC2) containing 30-60% (w/w) verproside, 0.5-10% (w/w) veratric acid, 2-20% (w/w) catalposide, 1- 10% (w/w) picroside II, 1-10% (w/w) isovanilloyl catalpol and 2-20% (w/w) 6-O-veratroyl catalpol based on the weight of total extract (100%) of *Pseudolysimachion rotundum* var *subintegrum* into the mammal suffering from chronic obstructive pulmonary disease (COPD).

2. A method of treating chronic obstructive pulmonary disease (COPD) in mammals, wherein the method comprises administering a composition comprising therapeutically effective amount of the purified extract with the secondary fractionation (ATC2) containing 30-60% (w/w) verproside, 0.5-10% (w/w) veratric acid, 2-20% (w/w) catalposide, 1-10% (w/w) picroside II, 1-10% (w/w) isovanilloyl catalpol and 2-20% (w/w) 6-O-veratroyl catalpol based on the weight of total extract (100%) of *Pseudolysimachion rotundum* var *subintegrum* and the pharmaceutically acceptable carriers or excipients, into the mammal suffering from chronic obstructive pulmonary disease (COPD).

3. A method of treating chronic obstructive pulmonary disease (COPD) in mammals, wherein the method comprises administering a therapeutically effective amount of the combined compounds contained in *Pseudolysimachion rotundum* var *subintegrum* with mixed weight ratio of 45%-90% verproside, 1.0%-7.0% veratric acid, 3.0%-15% catalposide, 2.0%-10% picroside II, 2.0%-10% isovanilloyl catalpol and 2.0-15% 6-O-veratroyl catalpol into the mammal suffering from chronic obstructive pulmonary disease (COPD).

4. A method of treating chronic obstructive pulmonary disease (COPD) in mammals, wherein the method comprises administering a composition comprising a therapeutically effective amount of the combined compounds contained in *Pseudolysimachion rotundum* var *subintegrum* with mixed weight ratio of 45%-90% verproside, 1.0%-7.0% veratric acid, 3.0%-15% catalposide, 2.0%-10% picroside II, 2.0%-10% isovanilloyl catalpol and 2.0-15% 6-O-veratroyl catalpol, and the pharmaceutically acceptable carriers or excipients, into the mammal suffering from chronic obstructive pulmonary disease (COPD).

\* \* \* \* \*

SEQUENCE LISTING

<160> NUMBER OF SEQ ID NOS: 5

<210> SEQ ID NO 1
<211> LENGTH: 26
<212> TYPE: DNA
<213> ORGANISM: Artificial Sequence
<220> FEATURE:
<223> OTHER INFORMATION: synthesized cDNA

<400> SEQUENCE: 1
catgttccag tatgactcca ctcacg         26

<210> SEQ ID NO 2
<211> LENGTH: 20
<212> TYPE: DNA
<213> ORGANISM: Mus sp.
<220> FEATURE:
<223> OTHER INFORMATION: Primer TGF-beta-1 Forward

<400> SEQUENCE: 2
tggagcaaca tgtggaactc         20

<210> SEQ ID NO 3
<211> LENGTH: 20
<212> TYPE: DNA
<213> ORGANISM: Mus sp.
<220> FEATURE:

```
<223> OTHER INFORMATION: Primer TGF-beta-1 Reverse

<400> SEQUENCE: 3
ctgccgtaca actccagtga                                                    20

<210> SEQ ID NO 4
<211> LENGTH: 24
<212> TYPE: DNA
<213> ORGANISM: Mus sp.
<220> FEATURE:
<223> OTHER INFORMATION: Primer MUC5AC Forward

<400> SEQUENCE: 4
agaatatctt tcaggacccc tgct                                               24

<210> SEQ ID NO 5
<211> LENGTH: 23
<212> TYPE: DNA
<213> ORGANISM: Mus sp.
<220> FEATURE:
<223> OTHER INFORMATION: Primer MUC5AC Reverse

<400> SEQUENCE: 5
acaccagtgc tgagcatact ttt                                                23
```